(12) United States Patent
Hunziker

(10) Patent No.: US 8,568,457 B2
(45) Date of Patent: Oct. 29, 2013

(54) NON-FUSION SCOLIOSIS EXPANDABLE SPINAL ROD

(75) Inventor: Markus Hunziker, Aarau (CH)

(73) Assignee: DePuy Synthes Products, LLC, Raynham, MA (US)

( * ) Notice: Subject to any disclaimer, the term of this patent is extended or adjusted under 35 U.S.C. 154(b) by 69 days.

(21) Appl. No.: 12/957,447

(22) Filed: Dec. 1, 2010

(65) Prior Publication Data

US 2011/0137347 A1    Jun. 9, 2011

Related U.S. Application Data

(60) Provisional application No. 61/265,568, filed on Dec. 1, 2009.

(51) Int. Cl.
*A61B 17/70* (2006.01)

(52) U.S. Cl.
USPC ............................ 606/258; 606/259; 606/246

(58) Field of Classification Search
USPC .................... 606/250–278, 53–60, 62–63
See application file for complete search history.

(56) References Cited

U.S. PATENT DOCUMENTS

| | | | |
|---|---|---|---|
| 3,270,792 A * | 9/1966 | Nenschotz et al. ............ 411/110 |
| 3,976,060 A | 8/1976 | Hildebrandt et al. |
| 4,312,336 A | 1/1982 | Danieletto et al. |
| 4,453,539 A | 6/1984 | Raftopoulos et al. |
| 4,921,499 A | 5/1990 | Hoffman et al. |
| 4,946,459 A | 8/1990 | Bradshaw et al. |
| 4,979,672 A | 12/1990 | AbuJudom, II et al. |
| 5,035,712 A | 7/1991 | Hoffman |
| 5,074,882 A | 12/1991 | Grammont et al. |
| 5,150,770 A | 9/1992 | Secci |
| 5,263,955 A | 11/1993 | Baumgart et al. |
| 5,356,411 A | 10/1994 | Spievack |
| 5,364,396 A | 11/1994 | Robinson et al. |
| 5,415,660 A | 5/1995 | Campbell et al. |
| 5,505,733 A | 4/1996 | Justin et al. |

(Continued)

FOREIGN PATENT DOCUMENTS

| | | |
|---|---|---|
| FR | 2906453 A1 * | 4/2008 |
| WO | 9951160 | 10/1999 |

(Continued)

OTHER PUBLICATIONS

Notification of Transmittal of the International Search Report and Written Opinion of the European Patent Office Searching Authority, dated Feb. 17, 2011.

*Primary Examiner* — Ellen C Hammond
*Assistant Examiner* — Jacqueline Johanas
(74) *Attorney, Agent, or Firm* — Meunier Carlin & Curfman, LLC

(57) ABSTRACT

A growing rod for mounting between attachment mechanisms that are secured to anatomical structures of a patient having scoliosis. The growing rod includes a base rod having an attachment end, an extendable rod that is translatable relative to the base rod along a longitudinal axis and a housing enclosing at least a portion of the extendable rod therein. A magnet is rotatably mounted within the housing and is enclosed by a top magnet cover and a bottom magnet cover. The magnet includes a first pole and a second pole. A gear reduction mechanism is associated with the magnet and the extendable rod. The gear reduction mechanism reduces an output rotation to the extendable rod relative to an input rotation from the magnet.

19 Claims, 49 Drawing Sheets

(56) References Cited

U.S. PATENT DOCUMENTS

| | | |
|---|---|---|
| 5,536,269 A | 7/1996 | Spievack |
| 5,551,871 A | 9/1996 | Besselink et al. |
| 5,575,790 A | 11/1996 | Chen et al. |
| 5,626,579 A | 5/1997 | Muschler et al. |
| 5,626,581 A | 5/1997 | Staehlin et al. |
| 5,672,177 A | 9/1997 | Seldin |
| 5,700,263 A | 12/1997 | Schendel |
| 5,704,939 A | 1/1998 | Justin |
| 5,720,746 A | 2/1998 | Soubeiran |
| 5,762,599 A | 6/1998 | Sohn |
| 5,766,004 A | 6/1998 | Besselink et al. |
| 5,827,286 A | 10/1998 | Incavo et al. |
| 5,961,553 A | 10/1999 | Coty et al. |
| 6,033,412 A | 3/2000 | Losken et al. |
| 6,036,690 A | 3/2000 | De La Plaza Fernandez |
| 6,187,004 B1 | 2/2001 | Fearon |
| 6,277,124 B1 | 8/2001 | Haag |
| 6,326,707 B1 | 12/2001 | Gummin et al. |
| 6,336,929 B1 | 1/2002 | Justin |
| 6,358,255 B1 | 3/2002 | Testa |
| 6,375,638 B2 | 4/2002 | Nason et al. |
| 6,383,185 B1 | 5/2002 | Baumgart |
| 6,417,750 B1 | 7/2002 | Sohn |
| 6,565,576 B1 | 5/2003 | Stauch et al. |
| 6,616,672 B1 | 9/2003 | Essiger |
| 6,673,079 B1 | 1/2004 | Kane |
| 6,684,724 B2 | 2/2004 | Narasimhiah et al. |
| 6,684,904 B2 | 2/2004 | Ito |
| 6,706,042 B2 | 3/2004 | Taylor |
| 6,716,218 B2 | 4/2004 | Holmes et al. |
| 6,730,087 B1 | 5/2004 | Butsch |
| 6,769,830 B1 | 8/2004 | Nygren |
| 6,796,984 B2 | 9/2004 | Soubeiran |
| 6,832,477 B2 | 12/2004 | Gummin et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,860,691 B2 | 3/2005 | Unsworth et al. |
| 6,918,910 B2 | 7/2005 | Smith et al. |
| 6,918,980 B2 | 7/2005 | Grabarz |
| 7,021,055 B2 | 4/2006 | Gummin et al. |
| 7,063,706 B2 | 6/2006 | Wittenstein |
| 7,135,022 B2 | 11/2006 | Kosahvili et al. |
| 7,240,677 B2 | 7/2007 | Fox |
| 7,282,052 B2 * | 10/2007 | Mullaney ................ 606/59 |
| 7,297,146 B2 | 11/2007 | Braun et al. |
| 8,043,299 B2 * | 10/2011 | Conway ................ 606/105 |
| 8,057,472 B2 * | 11/2011 | Walker et al. ................ 606/57 |
| 8,137,349 B2 * | 3/2012 | Soubeiran ................ 606/63 |
| 2003/0032958 A1 * | 2/2003 | Soubeiran ................ 606/61 |
| 2004/0030395 A1 | 2/2004 | Blunn et al. |
| 2004/0059331 A1 * | 3/2004 | Mullaney ................ 606/59 |
| 2004/0193266 A1 | 9/2004 | Meyer |
| 2005/0234448 A1 | 10/2005 | McCarthy |
| 2006/0009767 A1 | 1/2006 | Kiester |
| 2006/0047282 A1 | 3/2006 | Gordon |
| 2006/0074448 A1 | 4/2006 | Harrison et al. |
| 2006/0079897 A1 | 4/2006 | Harrison et al. |
| 2006/0271107 A1 | 11/2006 | Harrison et al. |
| 2007/0073098 A1 | 3/2007 | Lenker et al. |
| 2007/0185374 A1 | 8/2007 | Kick et al. |
| 2007/0265646 A1 | 11/2007 | McCoy et al. |
| 2007/0270803 A1 | 11/2007 | Giger et al. |
| 2007/0276378 A1 | 11/2007 | Harrison et al. |
| 2007/0282338 A1 * | 12/2007 | Mullaney ................ 606/59 |
| 2008/0097188 A1 | 4/2008 | Pool et al. |
| 2008/0097249 A1 | 4/2008 | Pool et al. |
| 2008/0108995 A1 * | 5/2008 | Conway et al. ................ 606/63 |
| 2008/0172072 A1 | 7/2008 | Pool et al. |
| 2009/0112262 A1 | 4/2009 | Pool et al. |
| 2009/0112263 A1 | 4/2009 | Pool et al. |
| 2009/0204154 A1 | 8/2009 | Kiester |
| 2009/0254088 A1 * | 10/2009 | Soubeiran ................ 606/63 |
| 2010/0217271 A1 * | 8/2010 | Pool et al. ................ 606/90 |

FOREIGN PATENT DOCUMENTS

| | | |
|---|---|---|
| WO | 0033752 | 6/2000 |
| WO | 2008109300 | 9/2008 |
| WO | 2009058546 | 5/2009 |

* cited by examiner

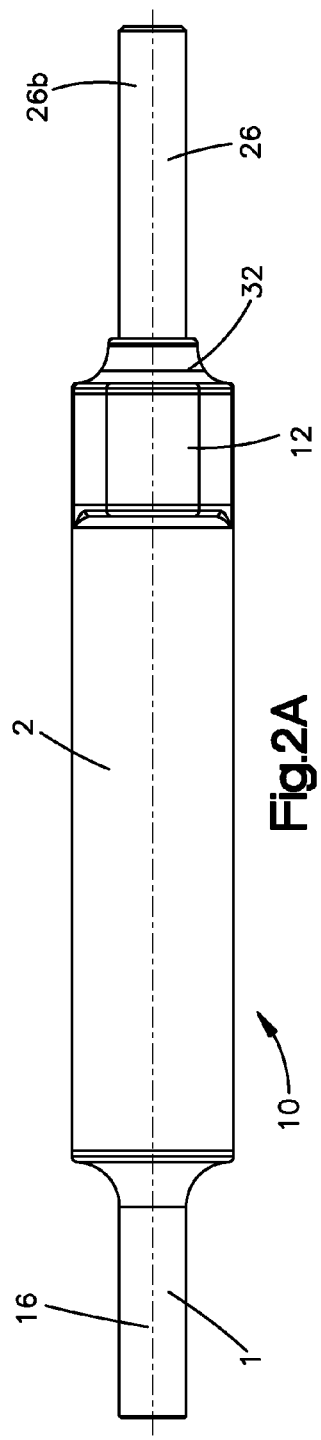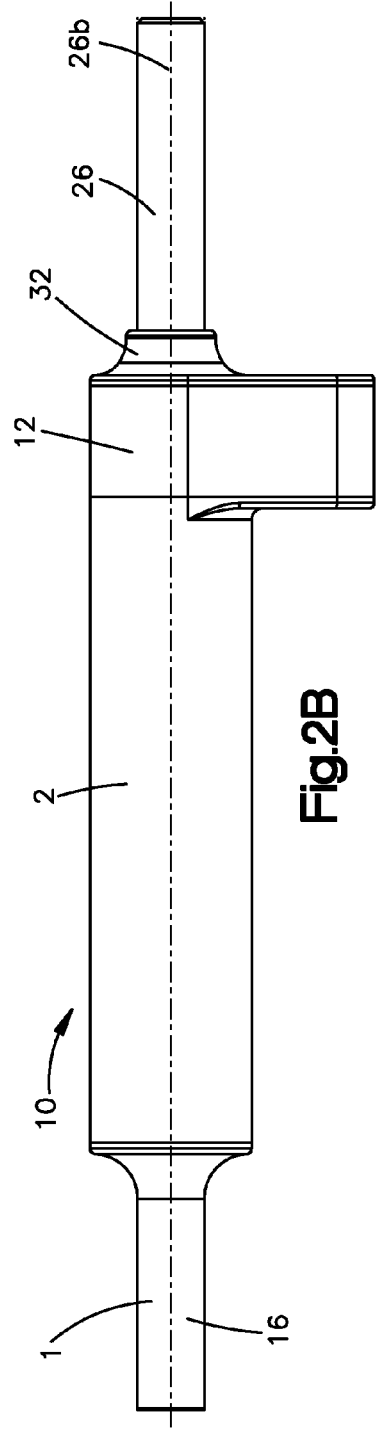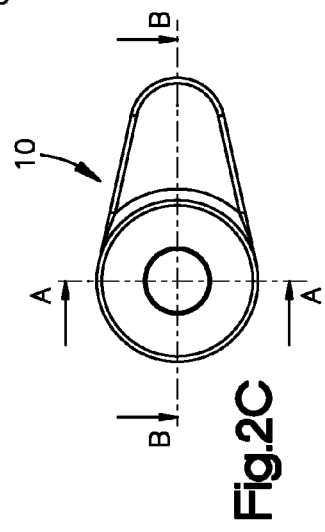

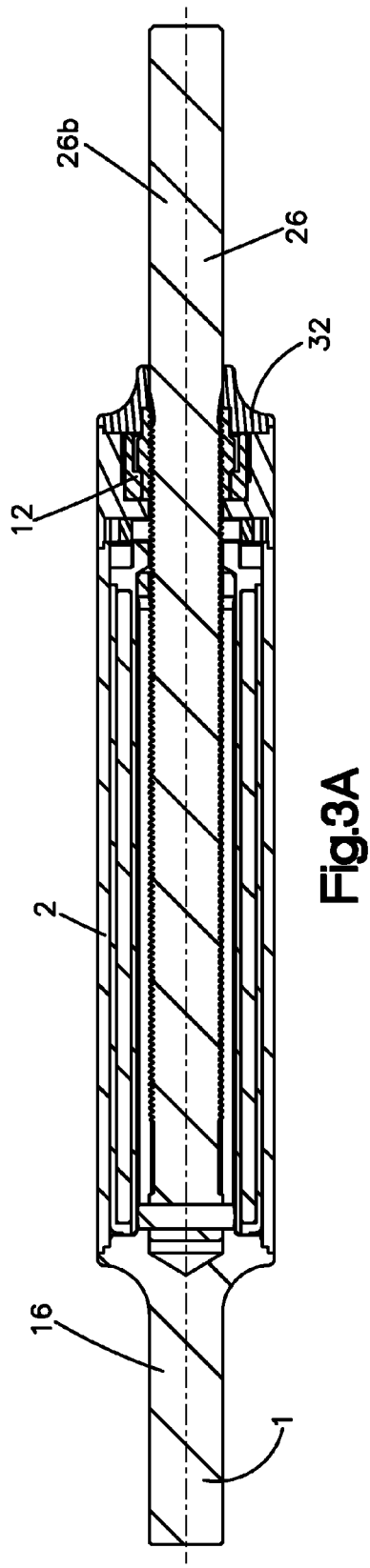
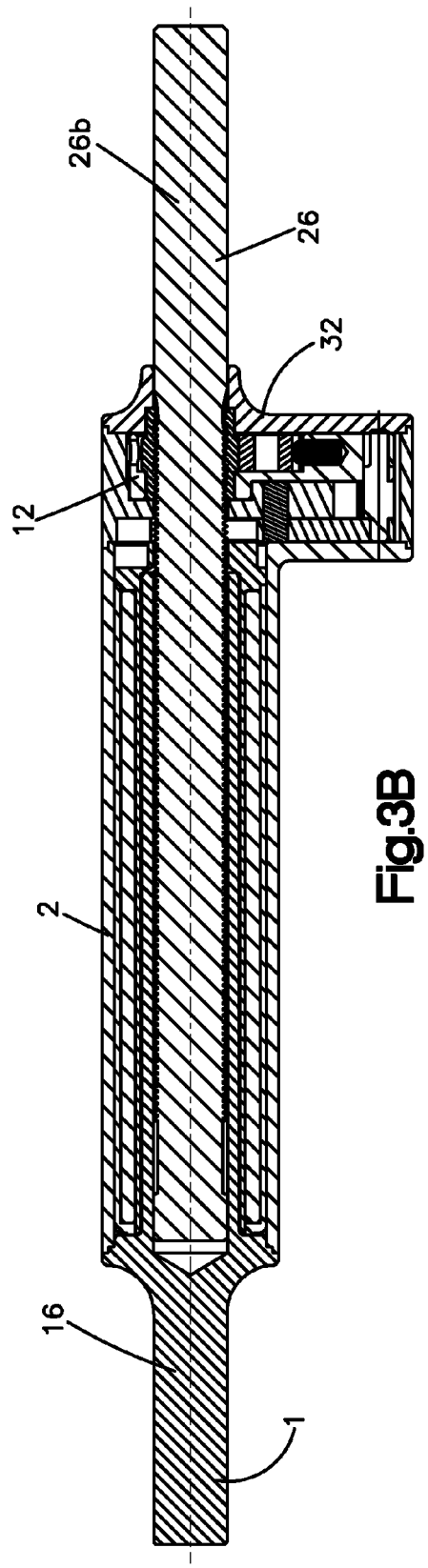
Fig.3A
Fig.3B

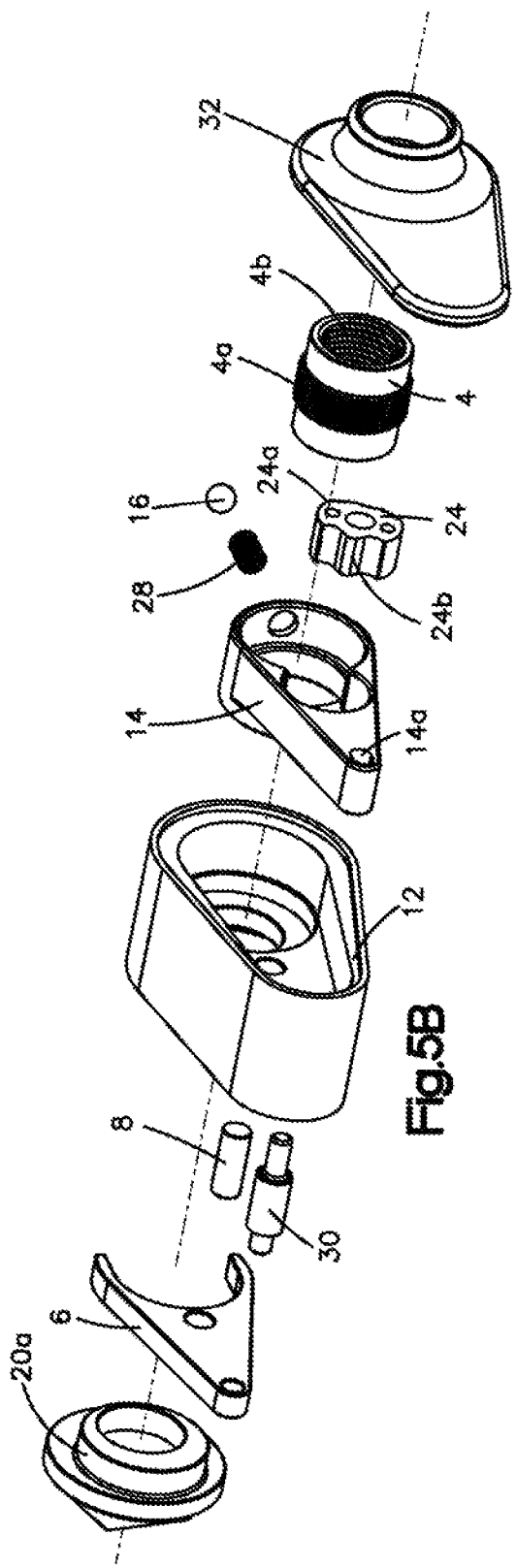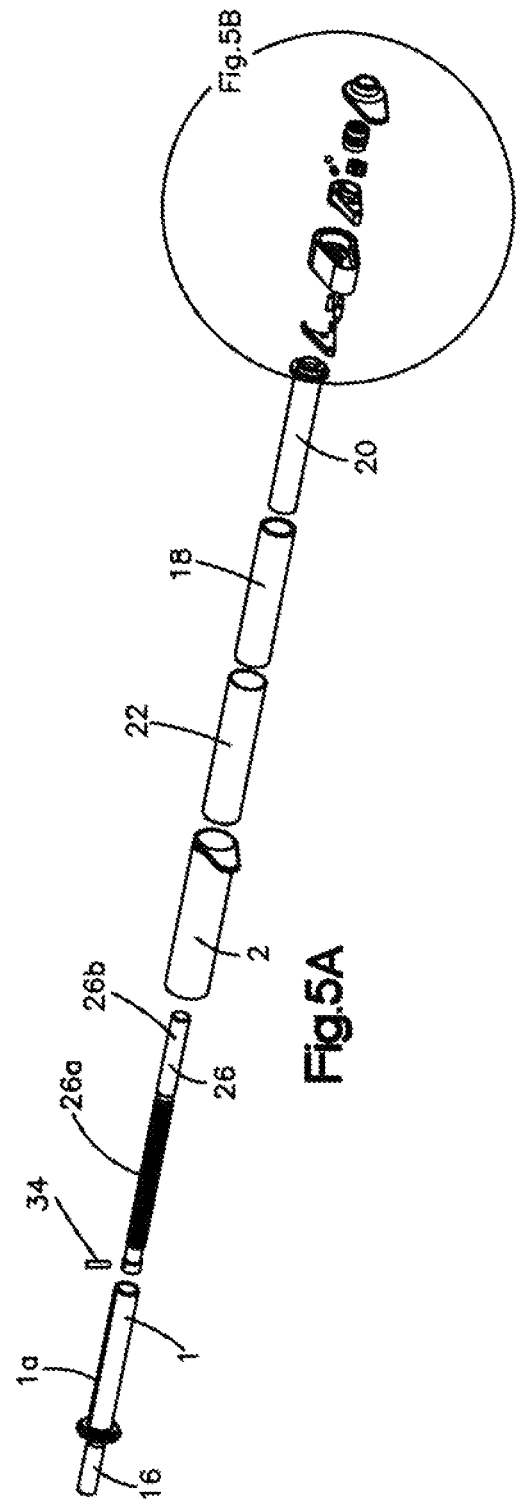

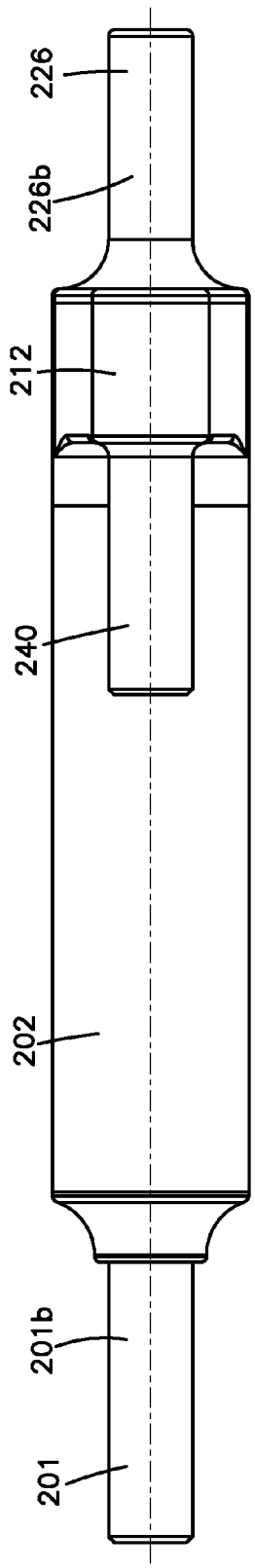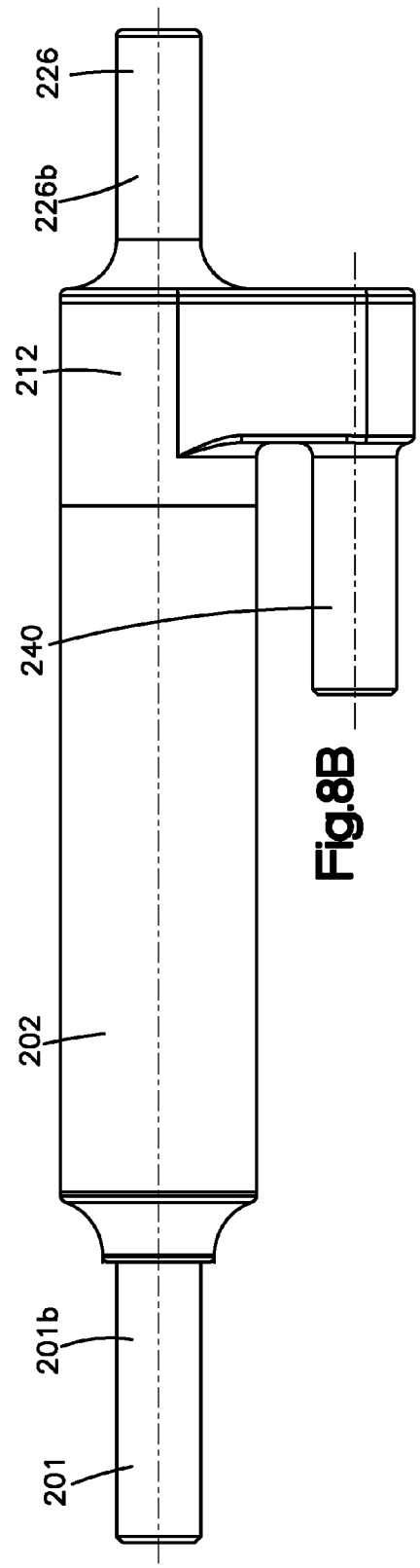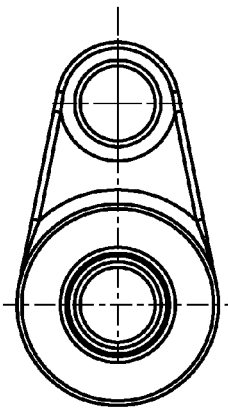

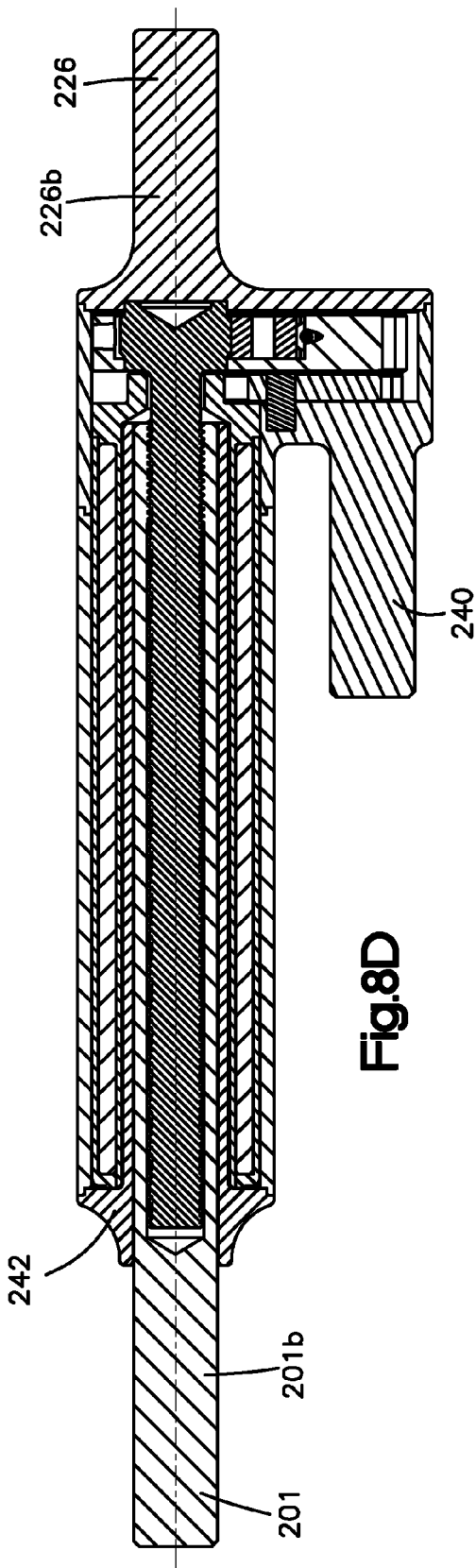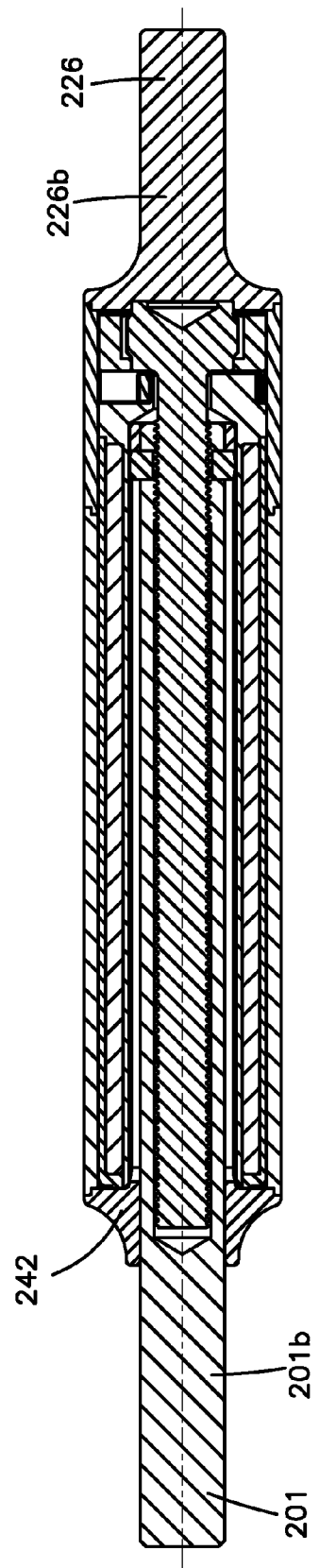
Fig.8D
Fig.8E

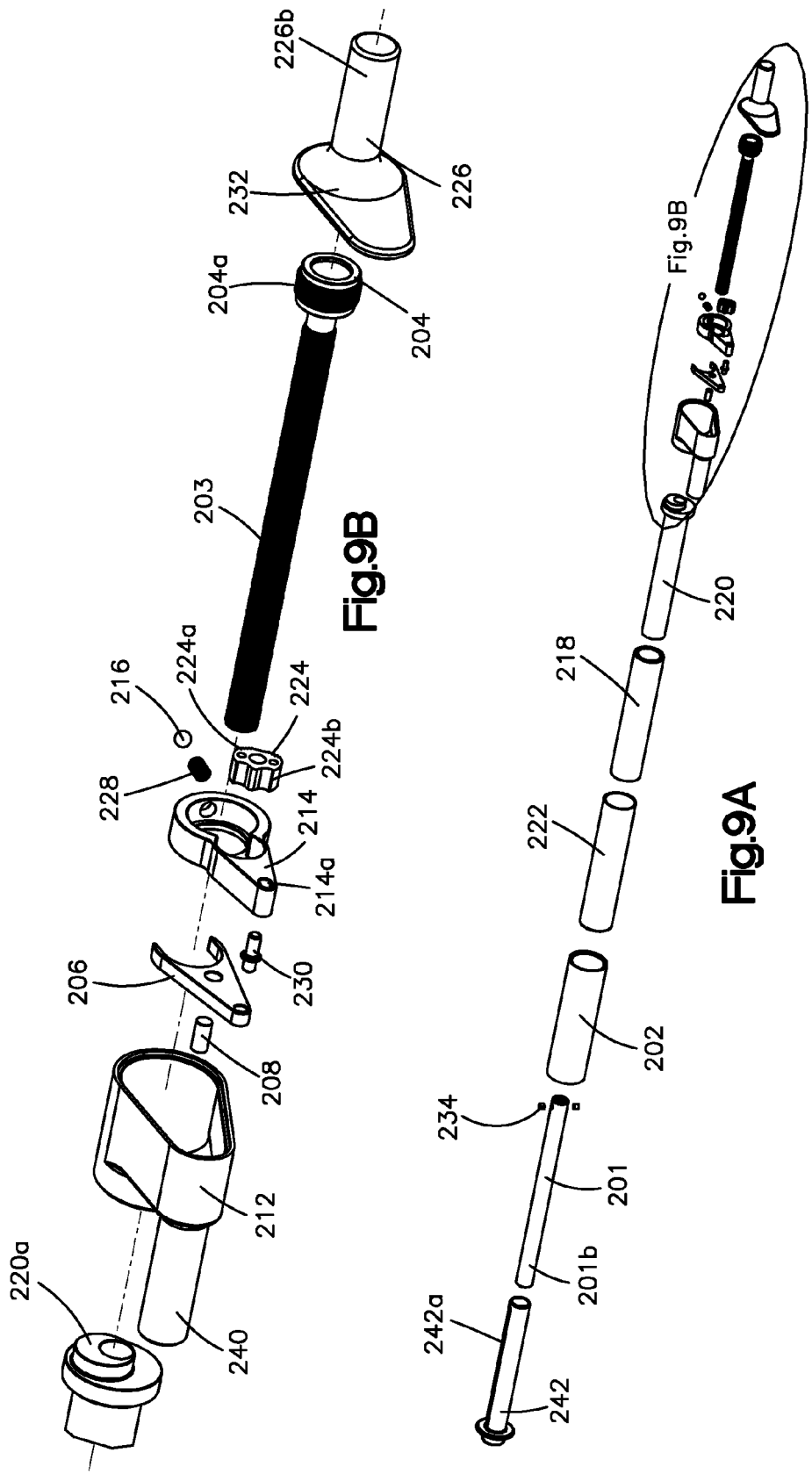

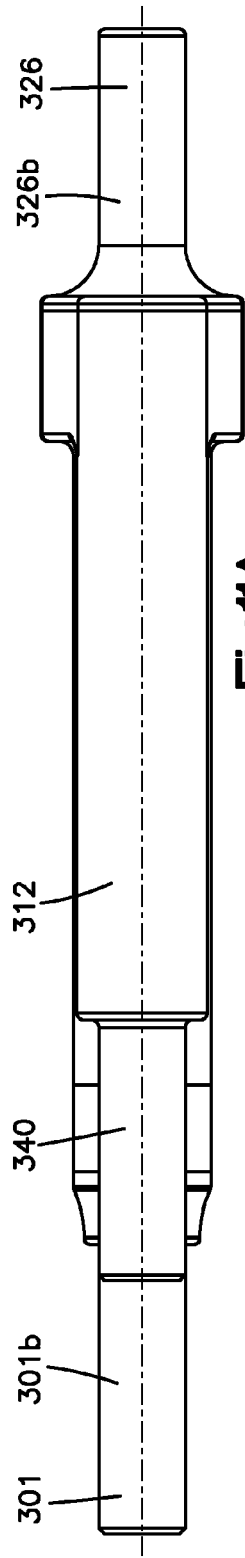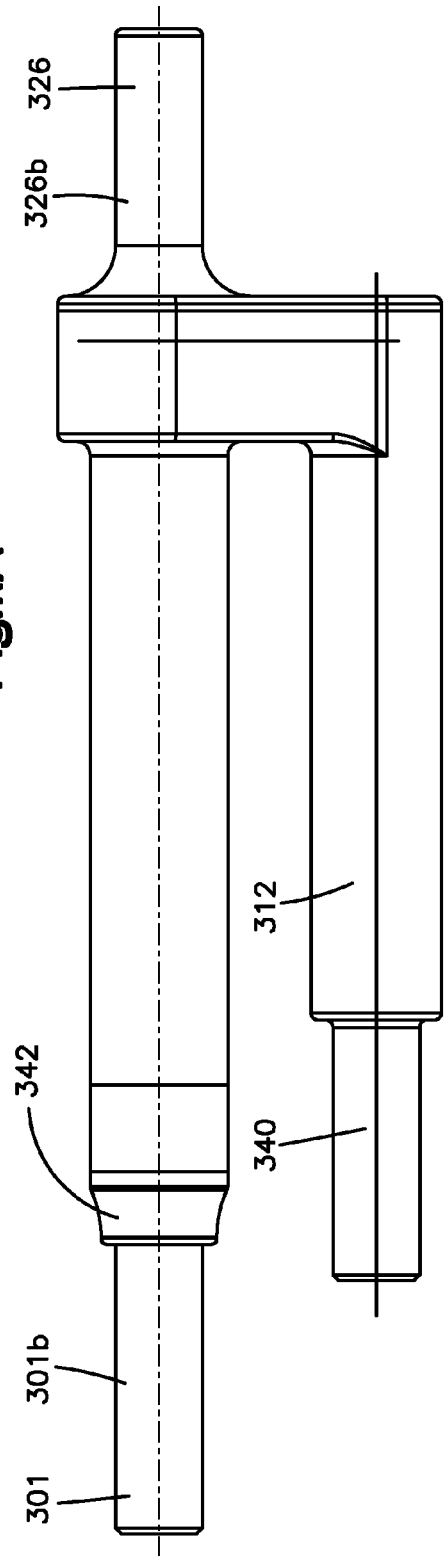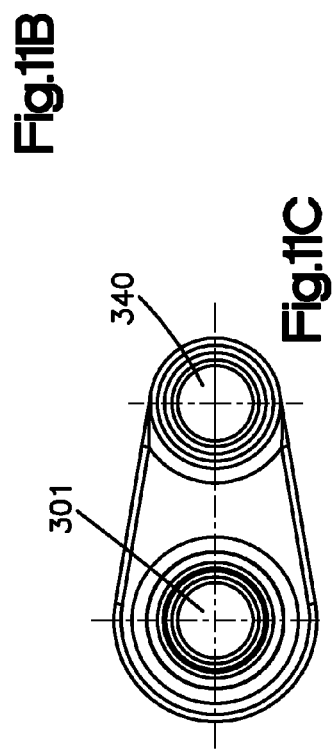

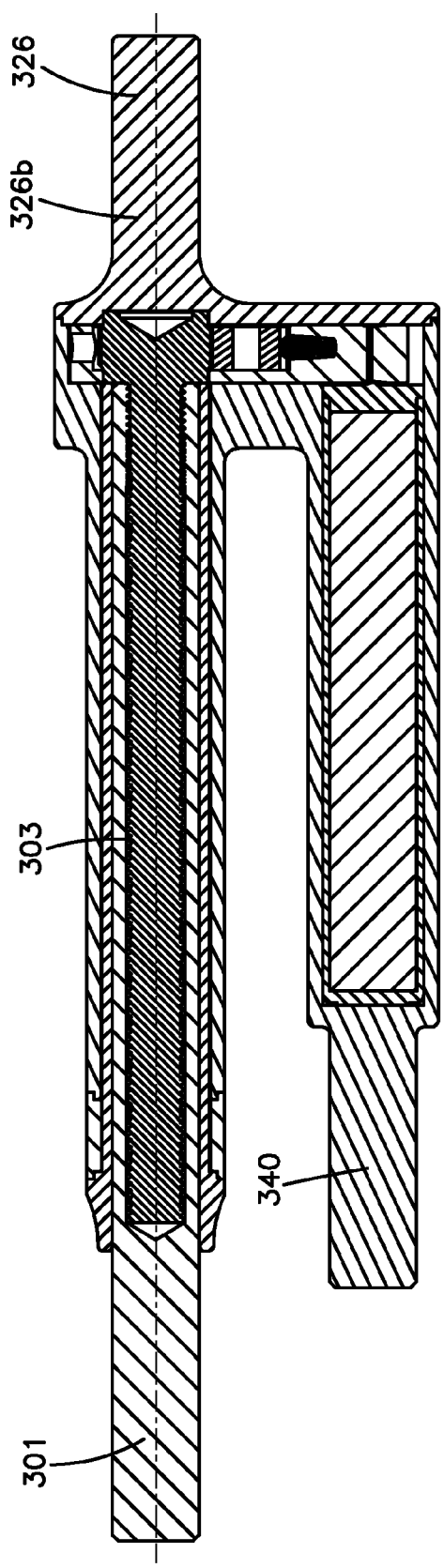
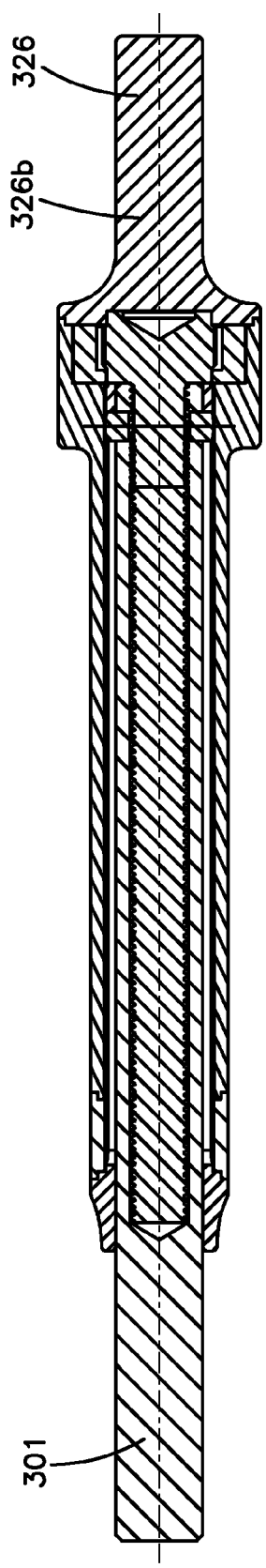
Fig.11D
Fig.11E

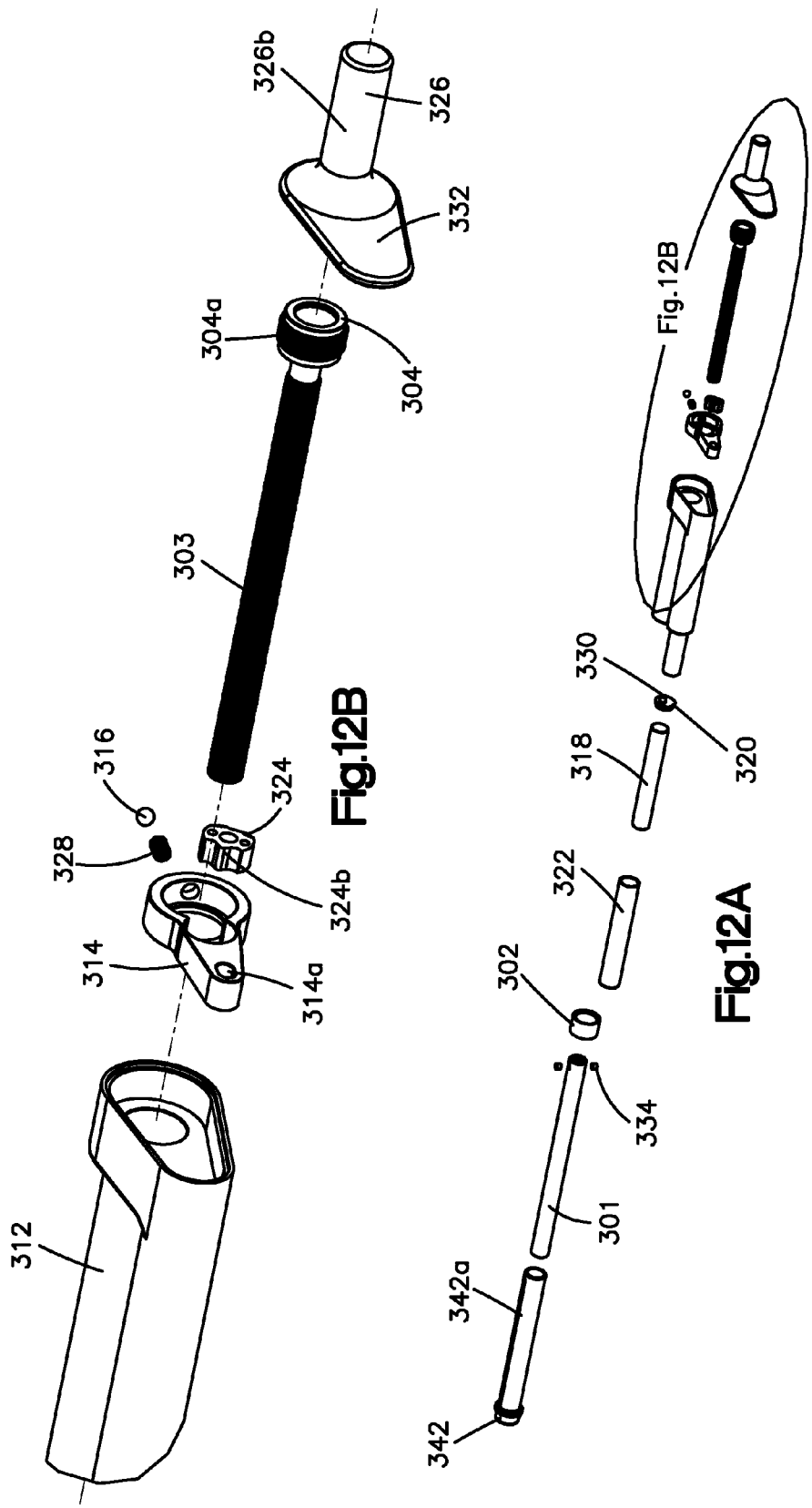

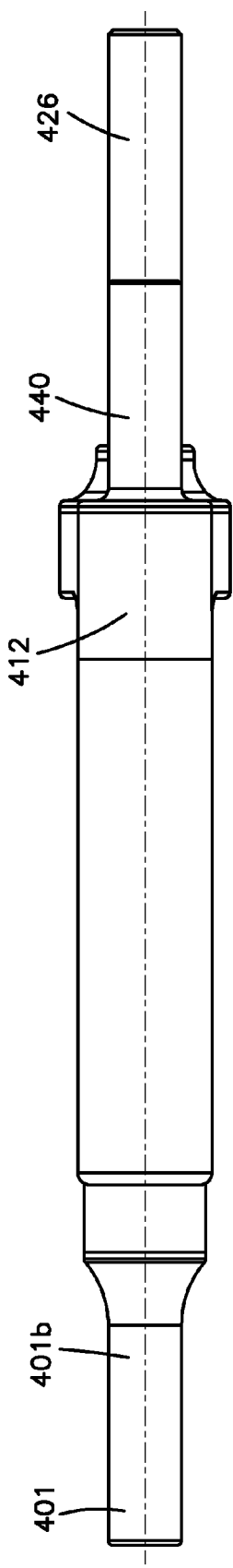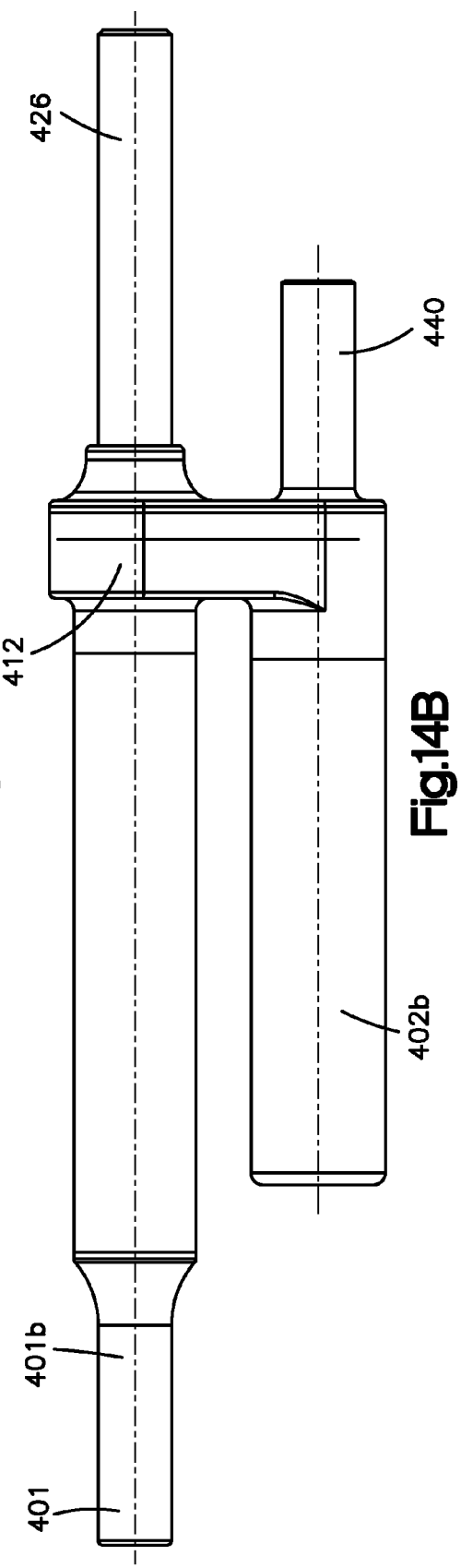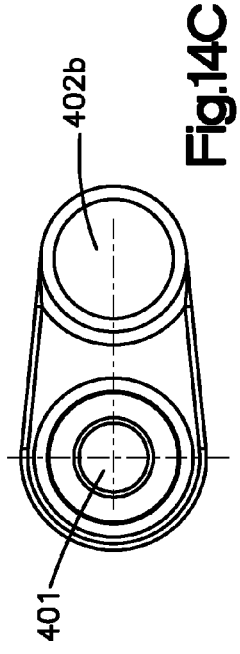

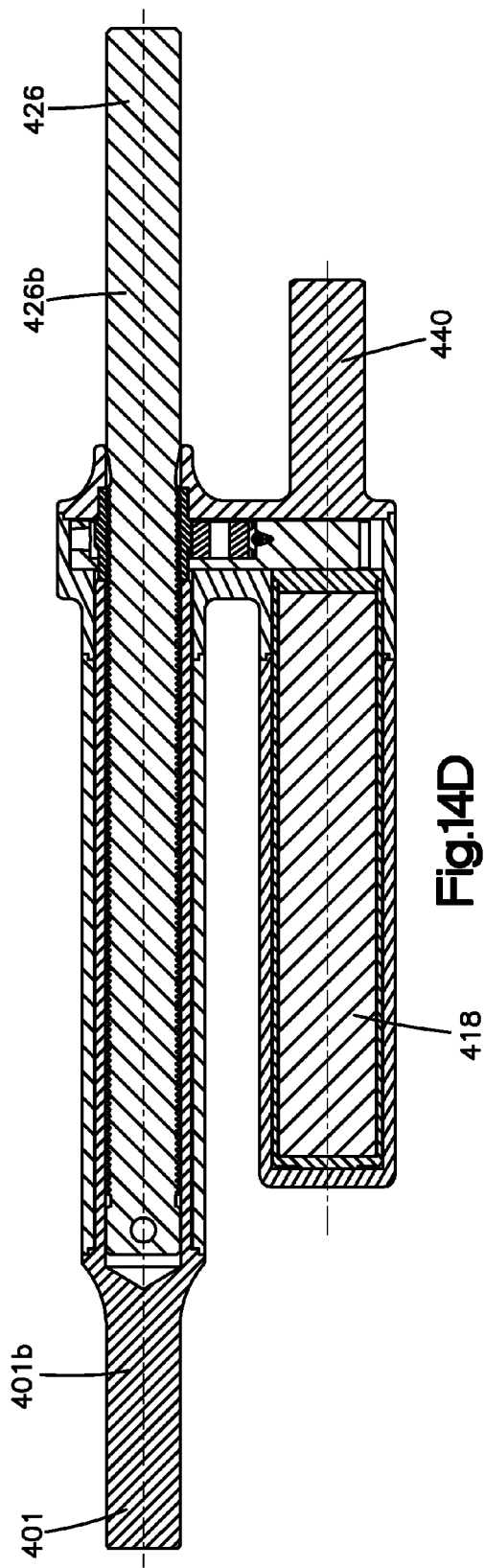
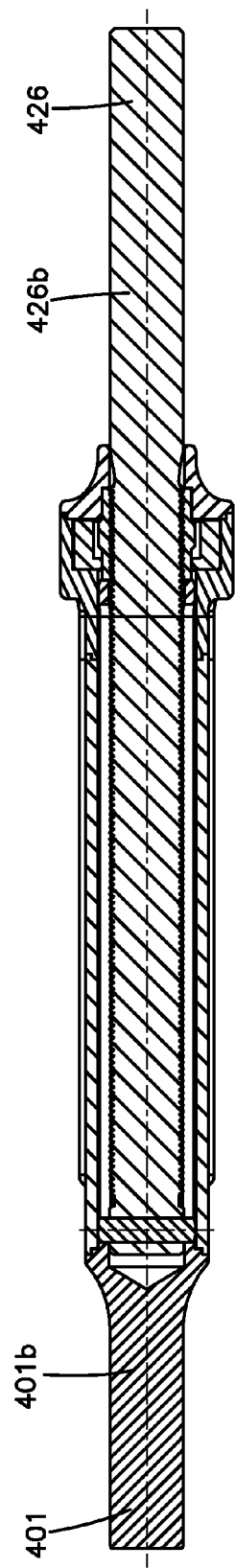
Fig.14D
Fig.14E

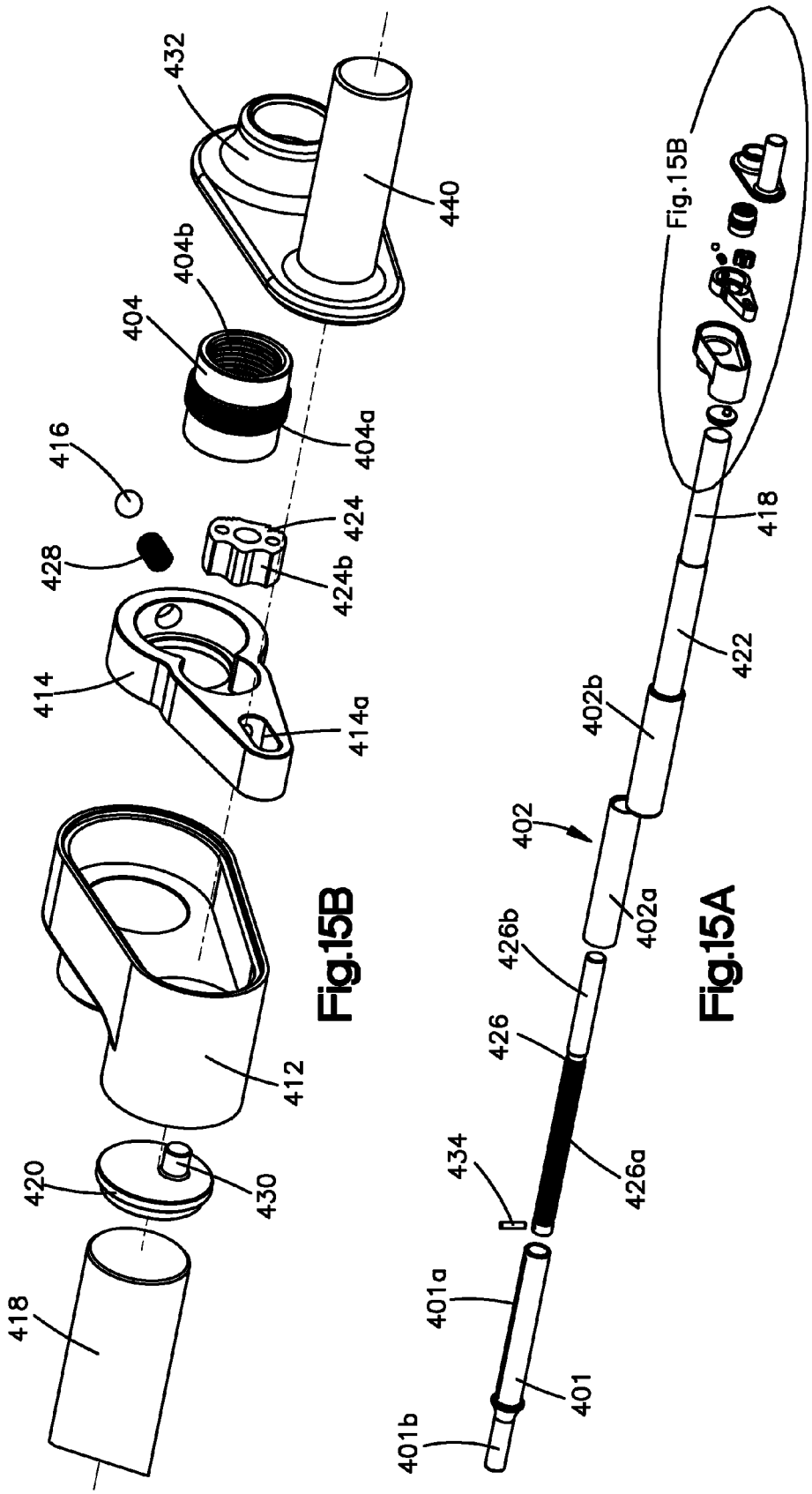

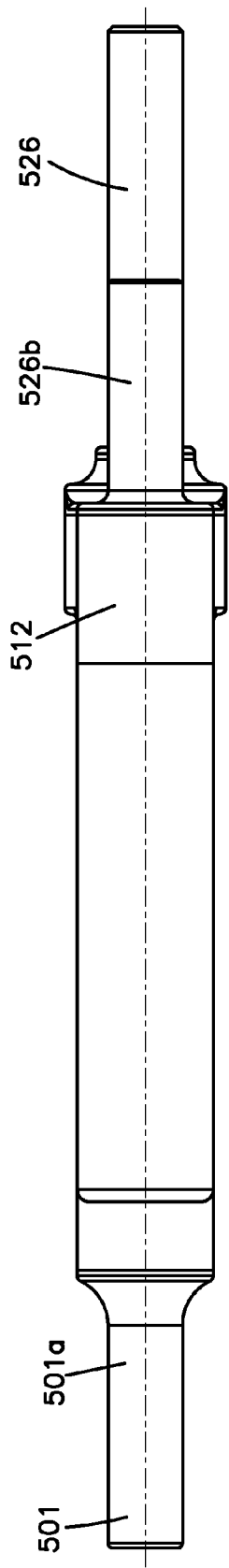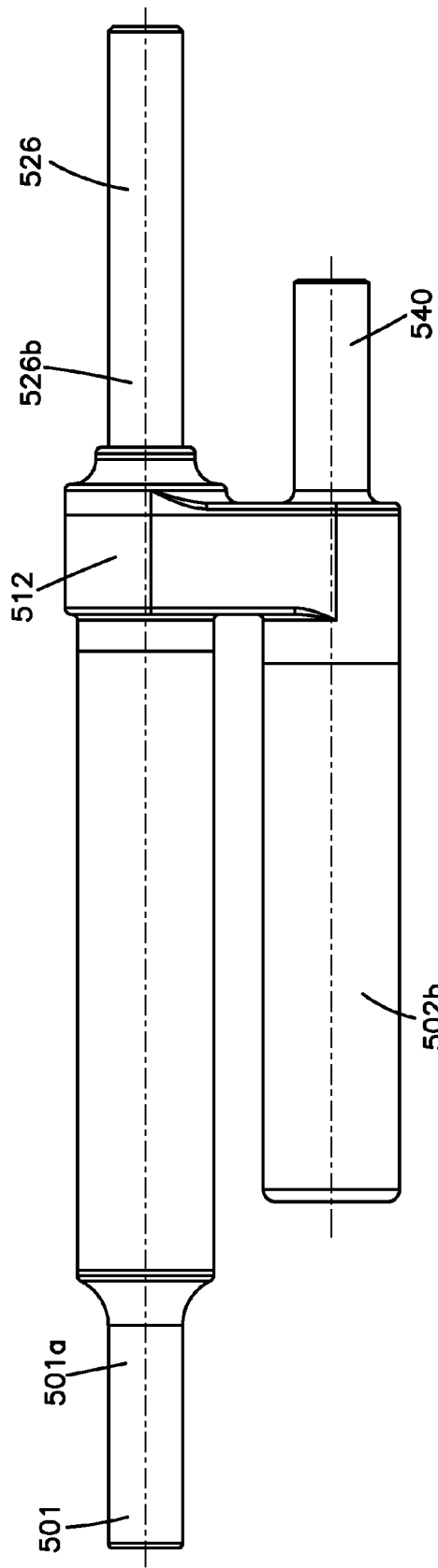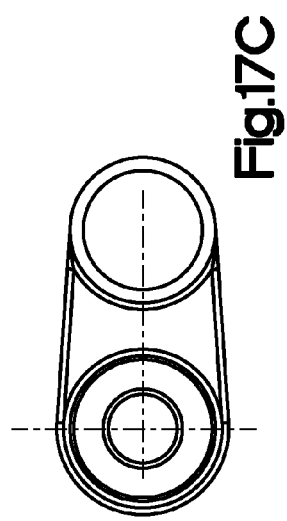

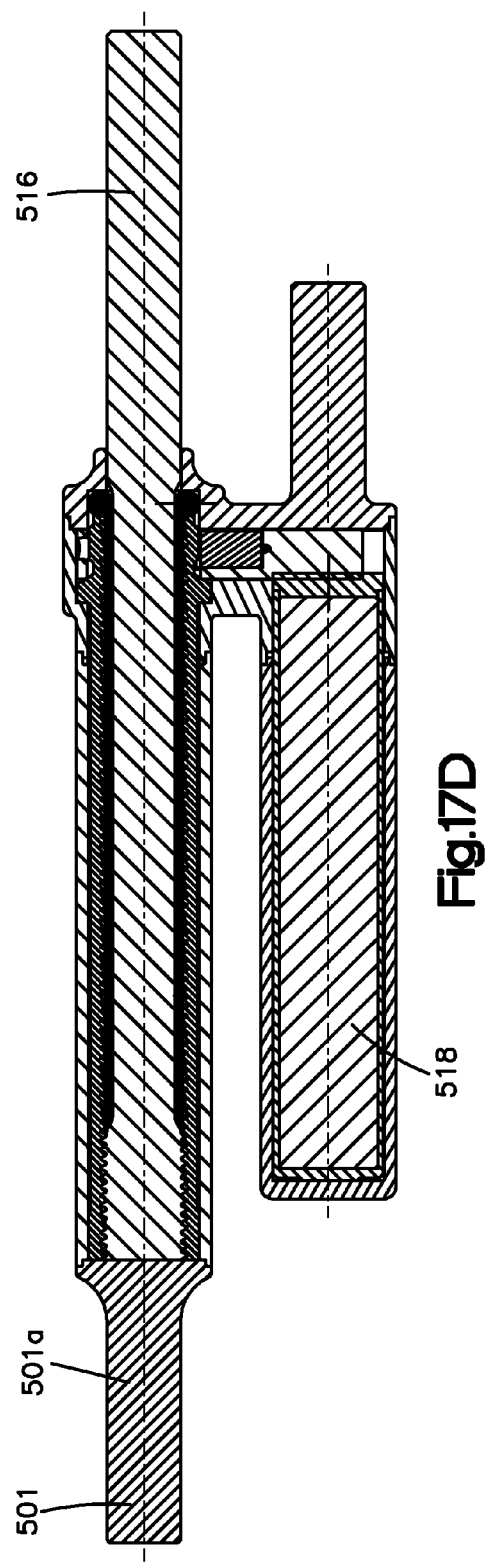
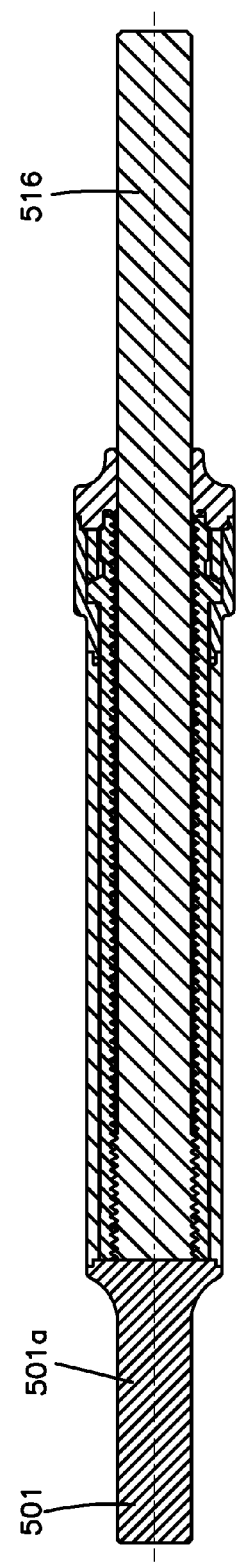

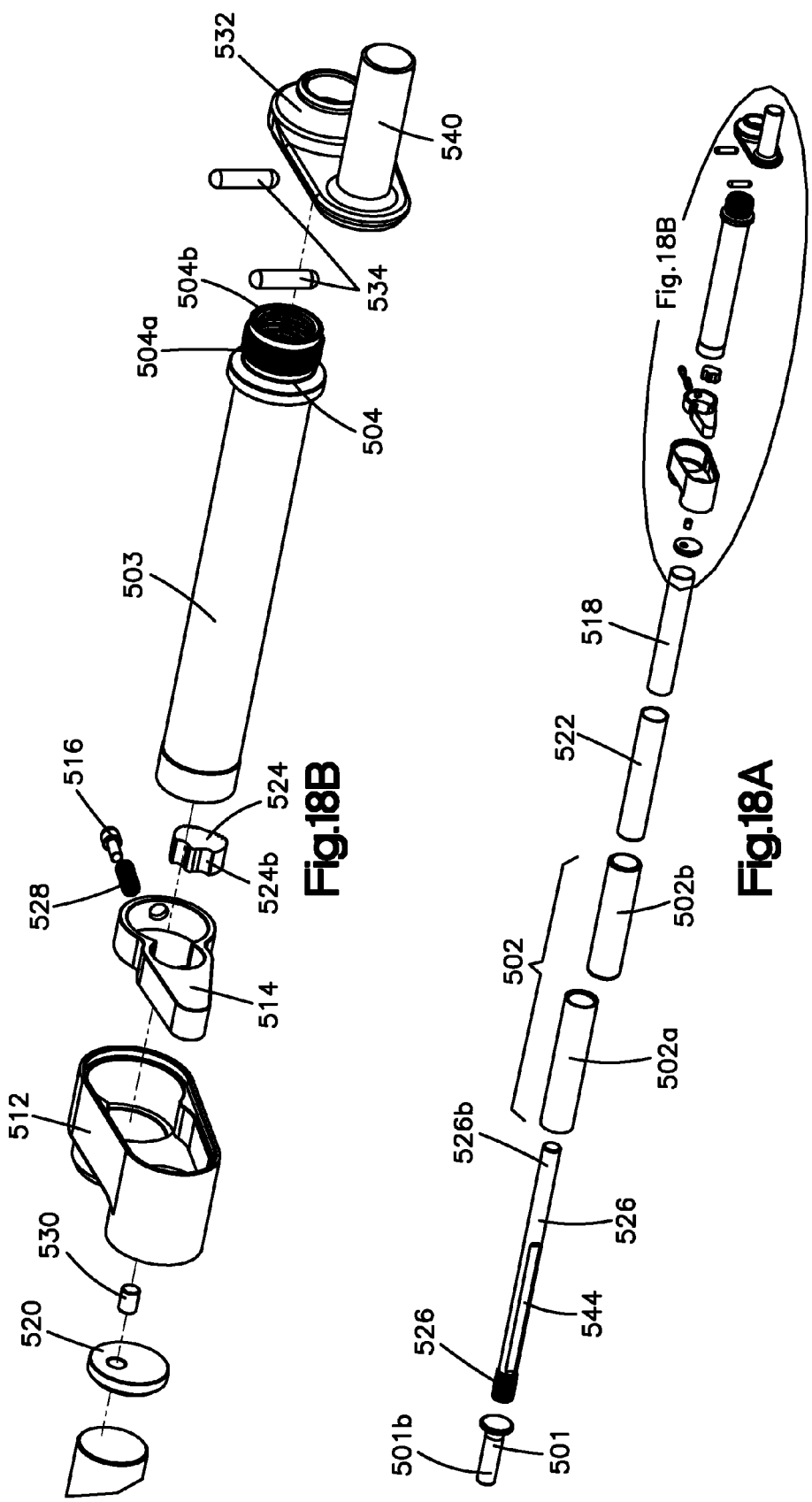

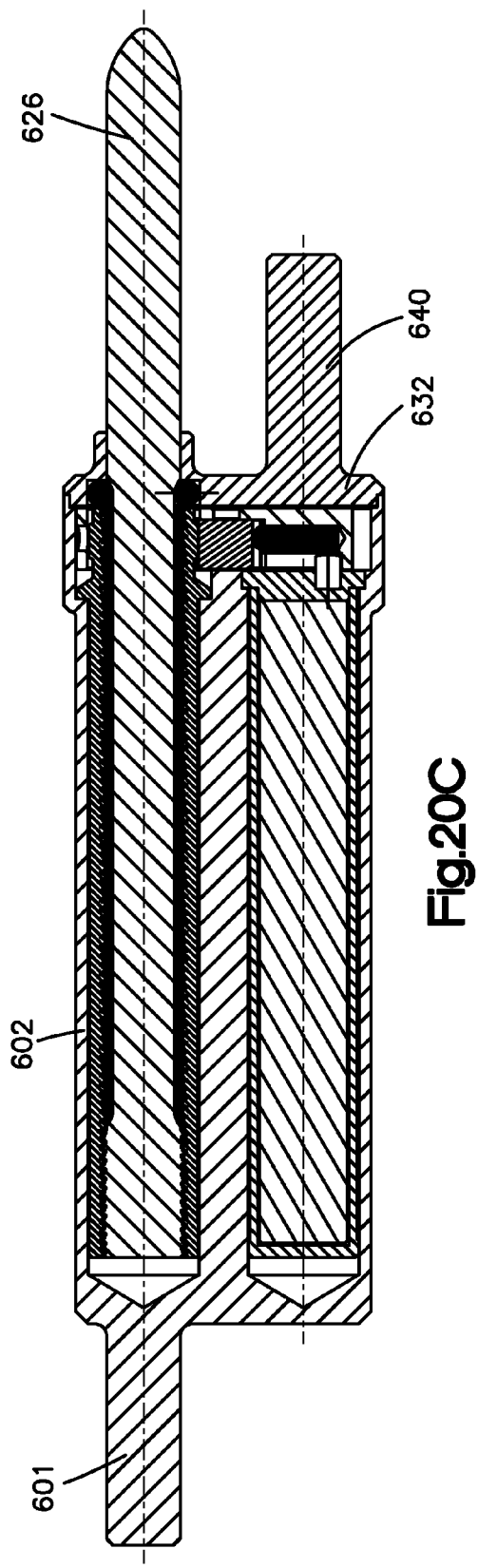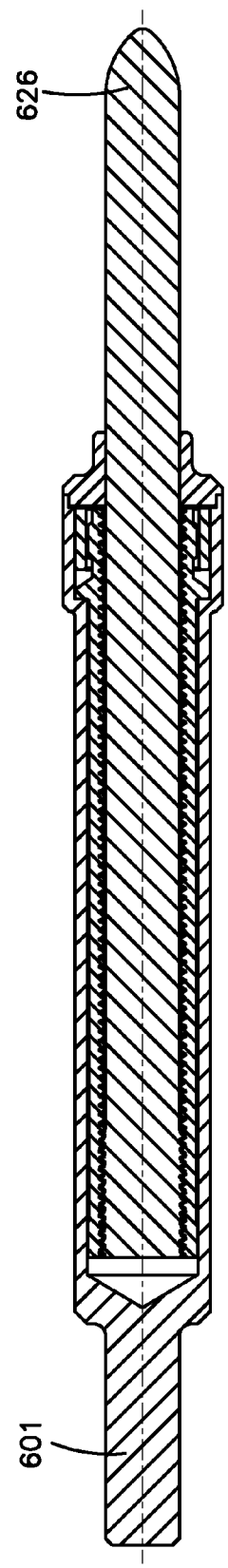

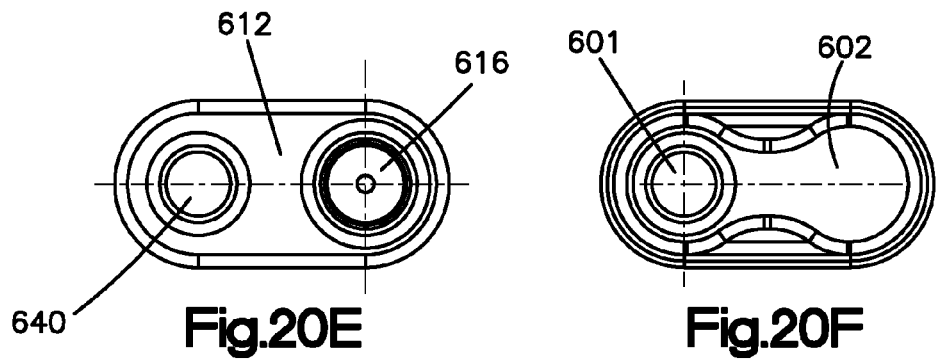
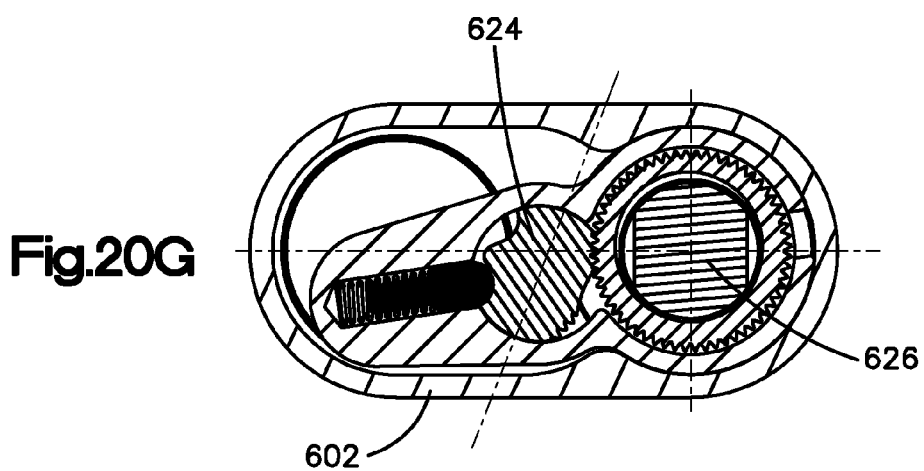
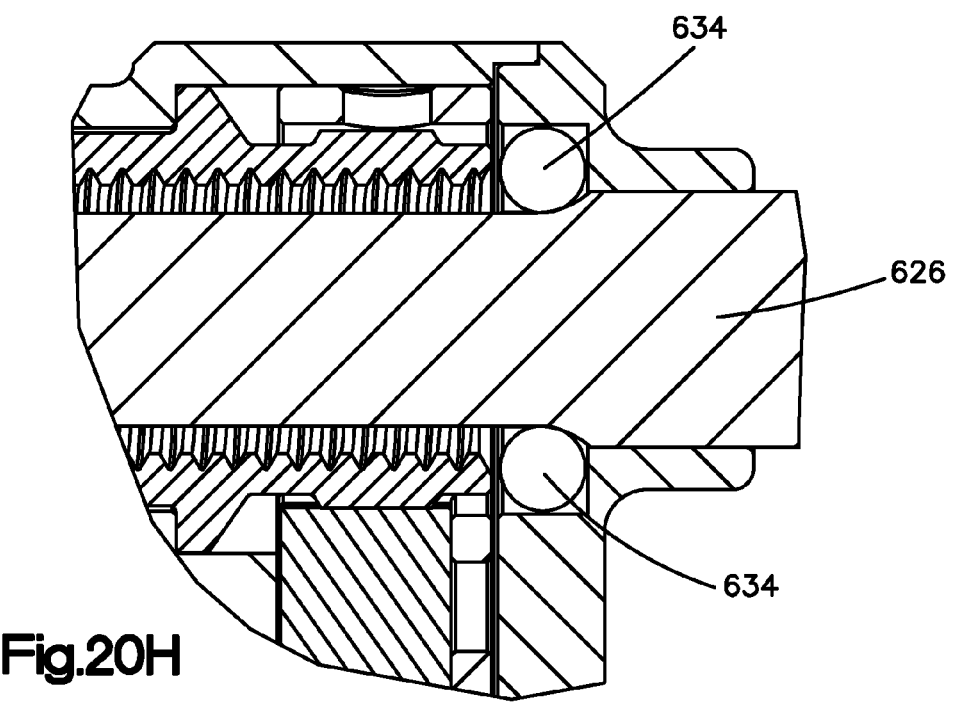

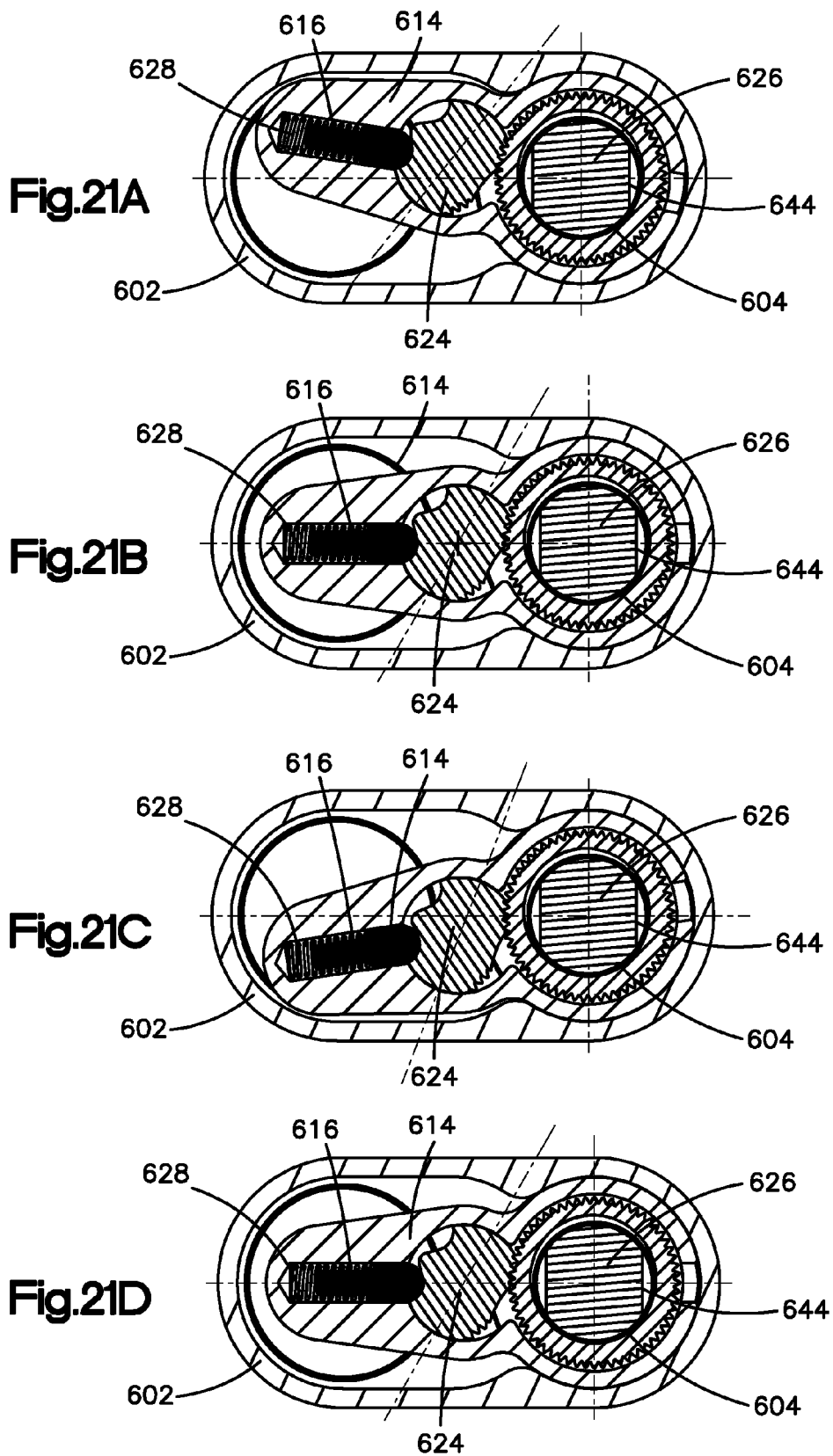

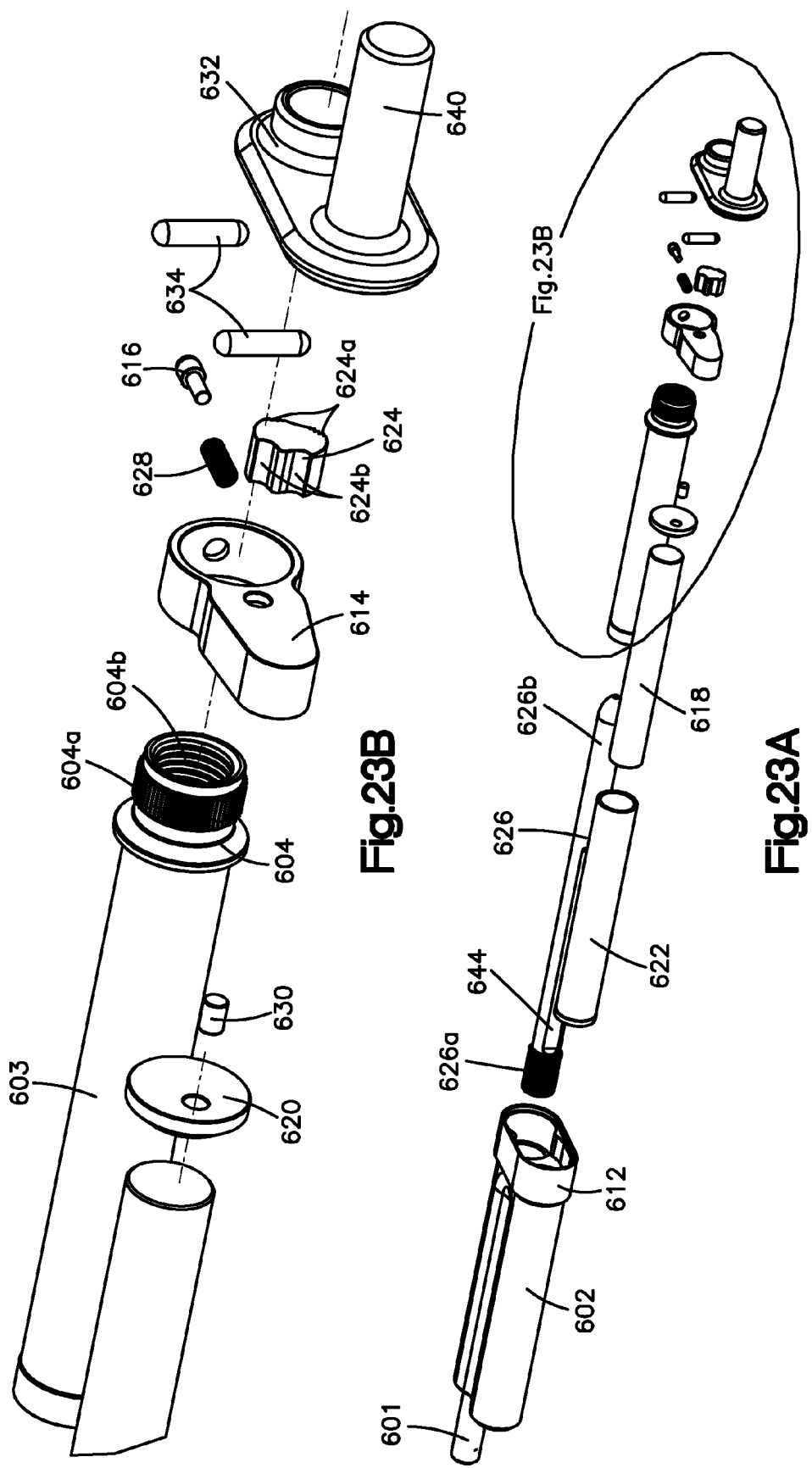

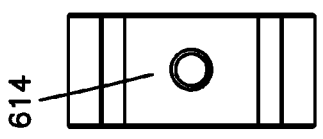
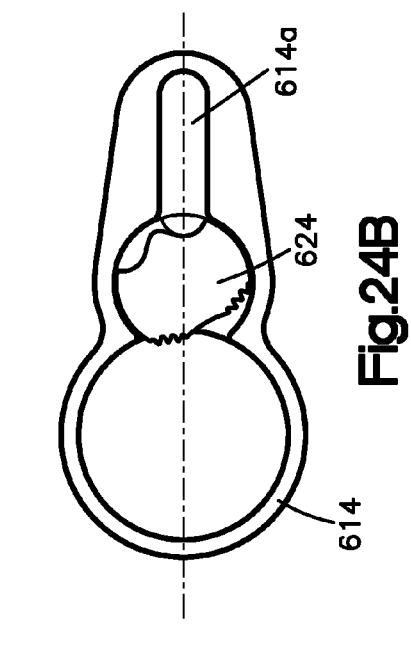
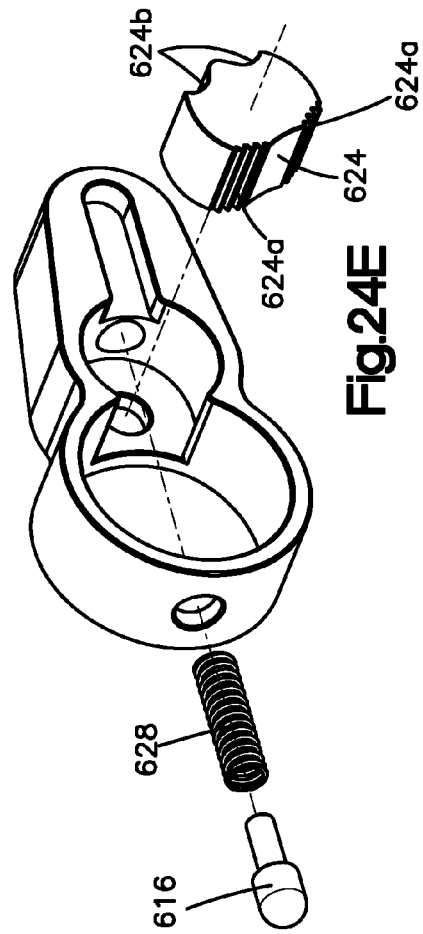
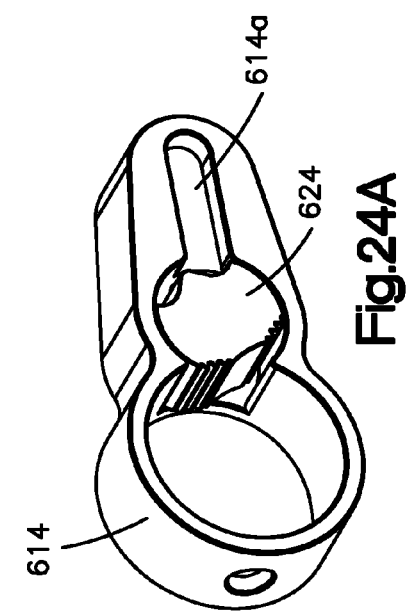
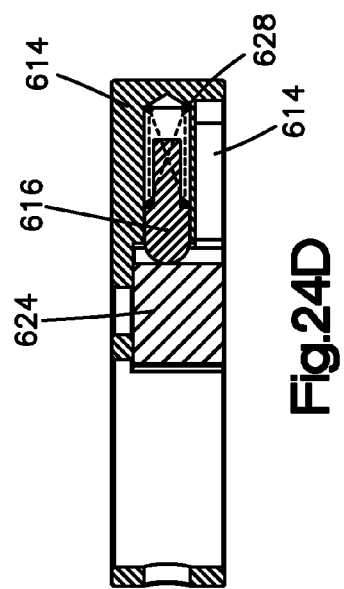

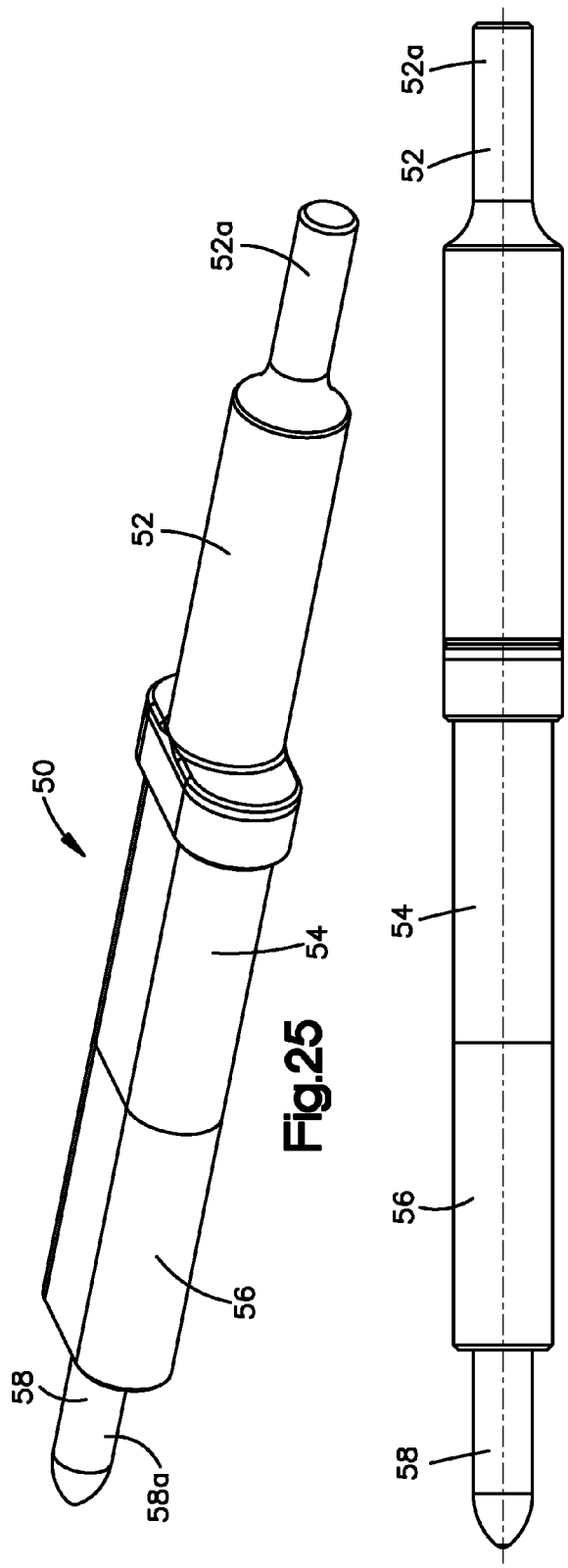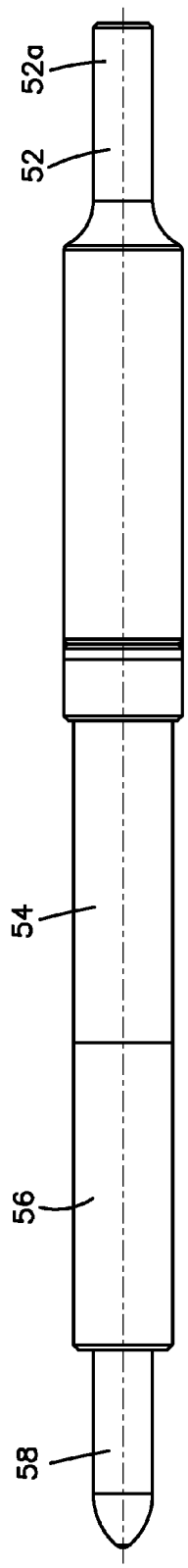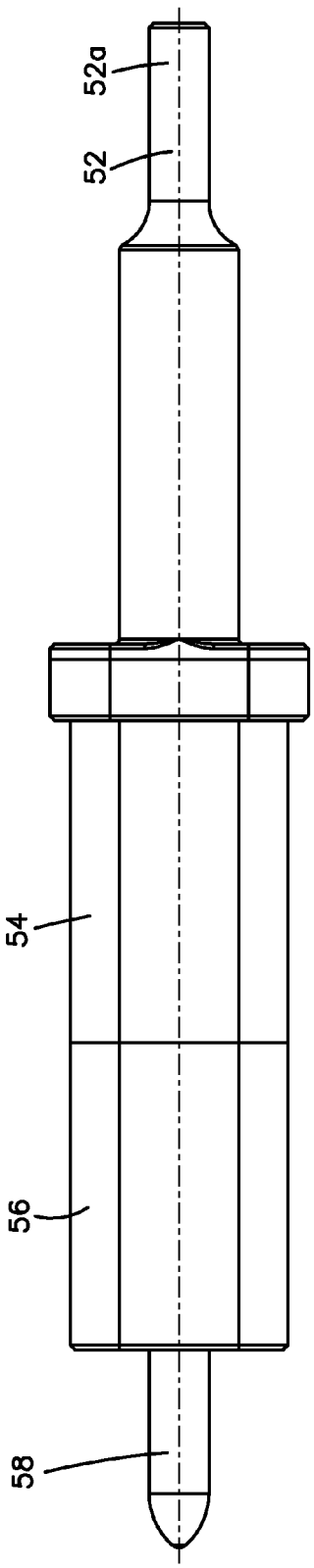

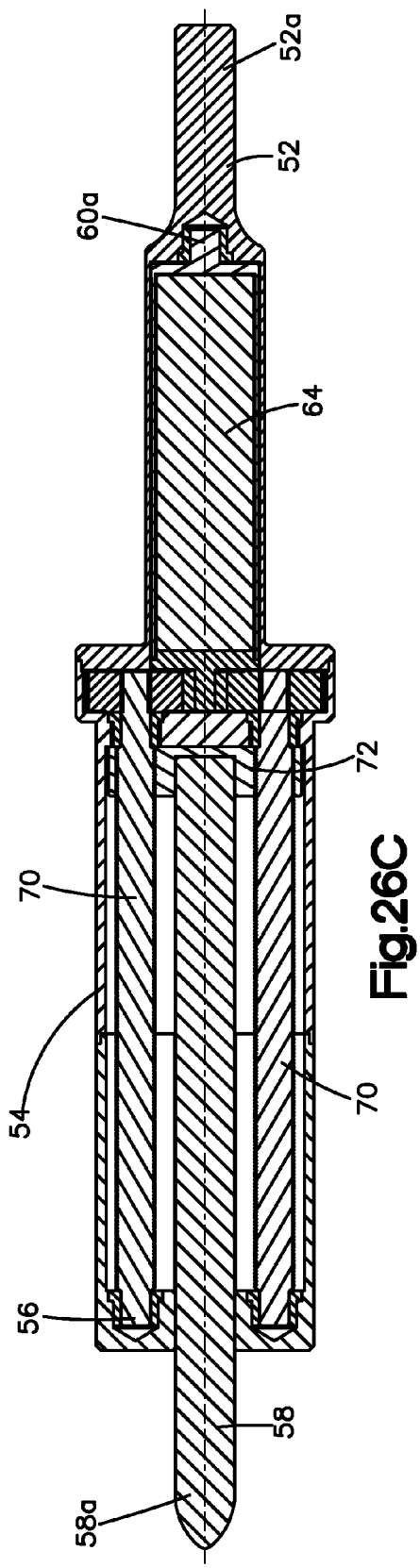
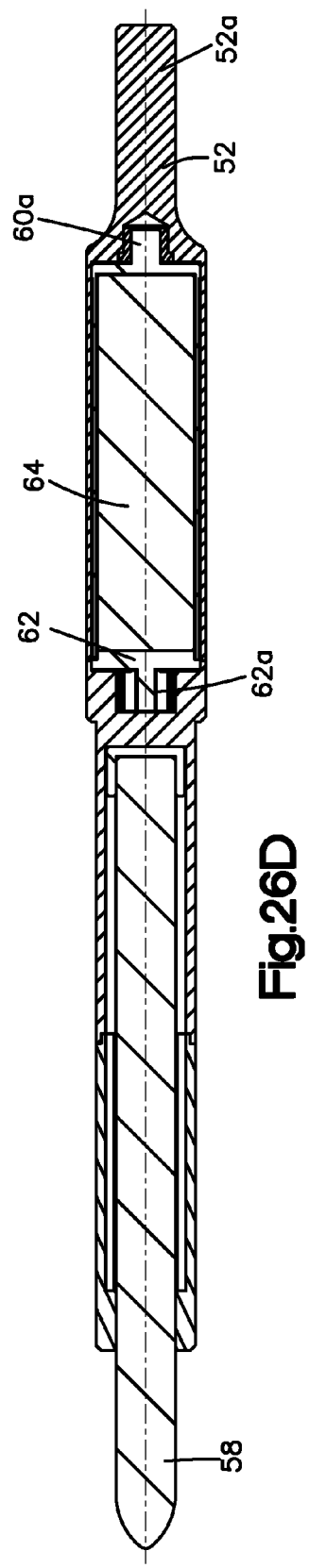
Fig.26C
Fig.26D

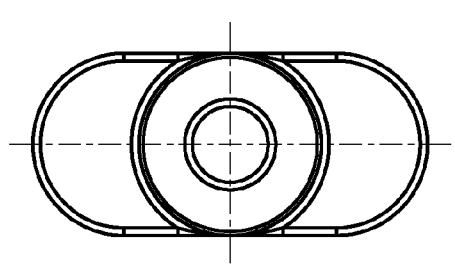
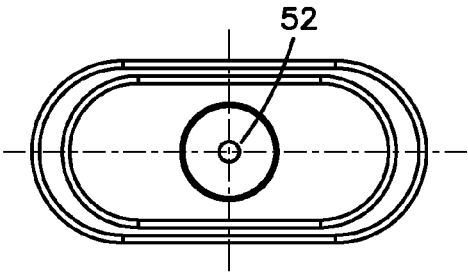
Fig.26E     Fig.26F
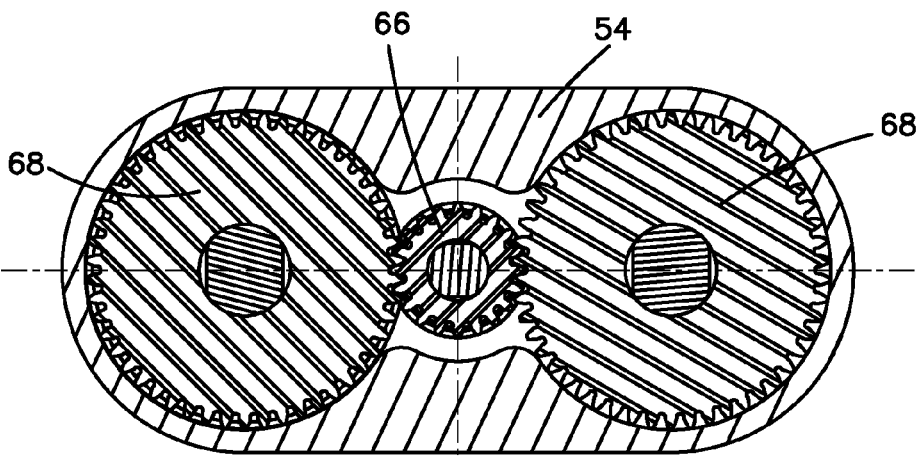
Fig.26G
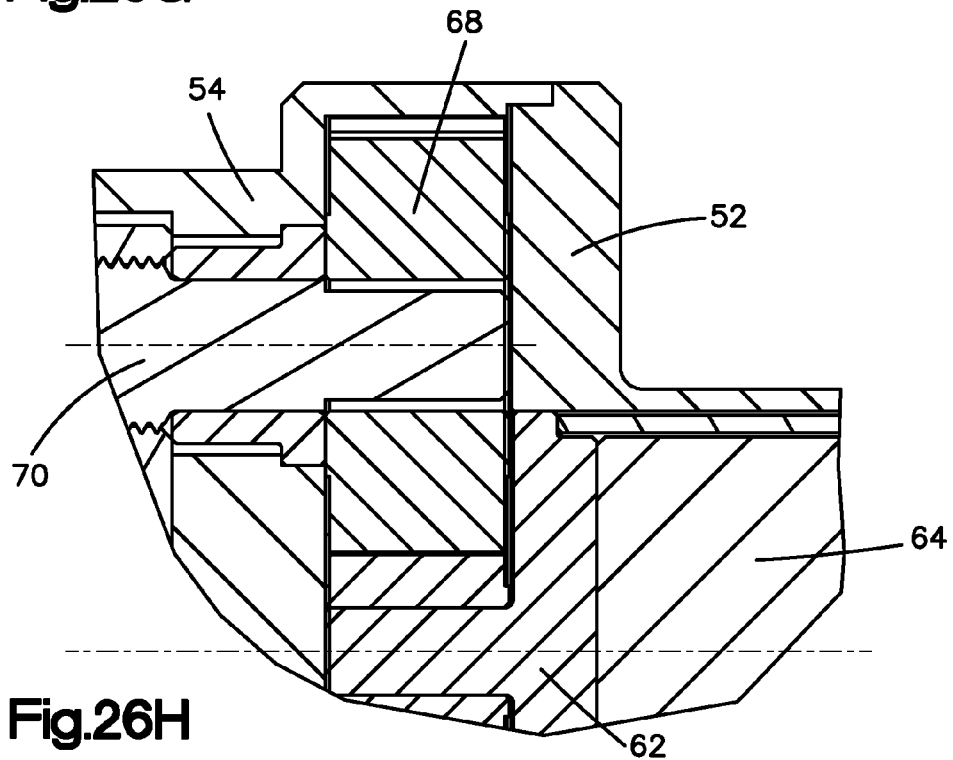
Fig.26H

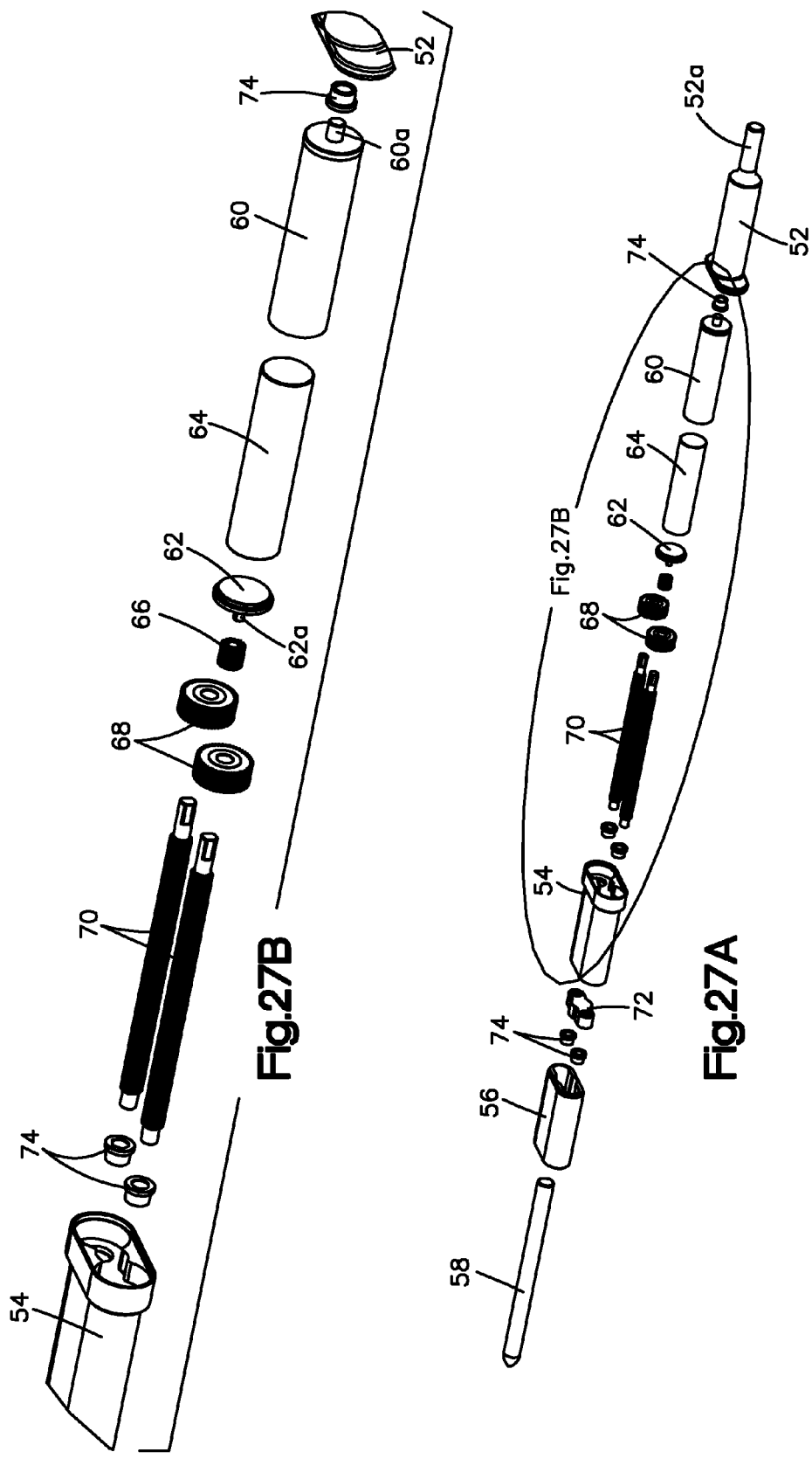

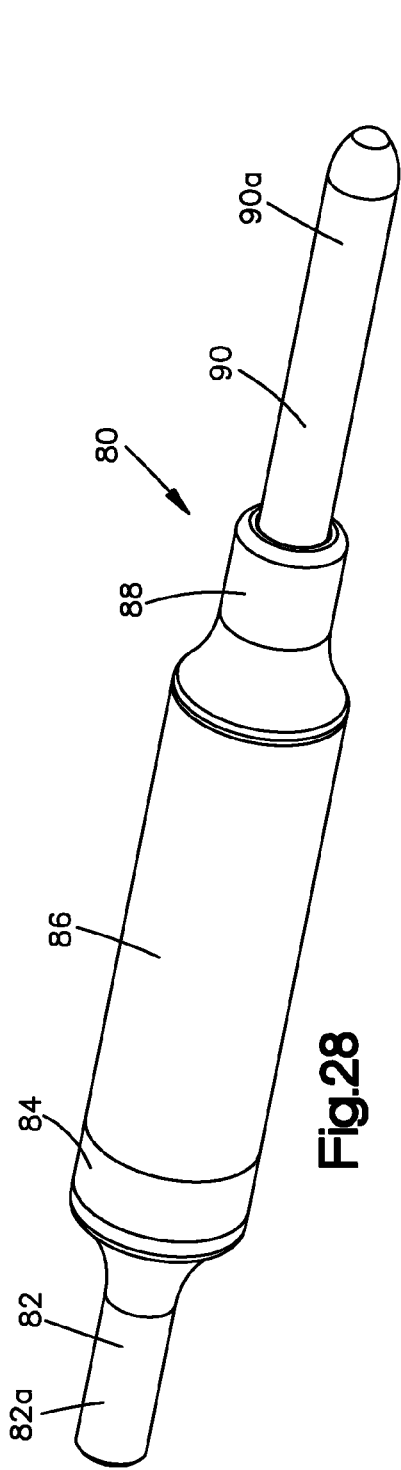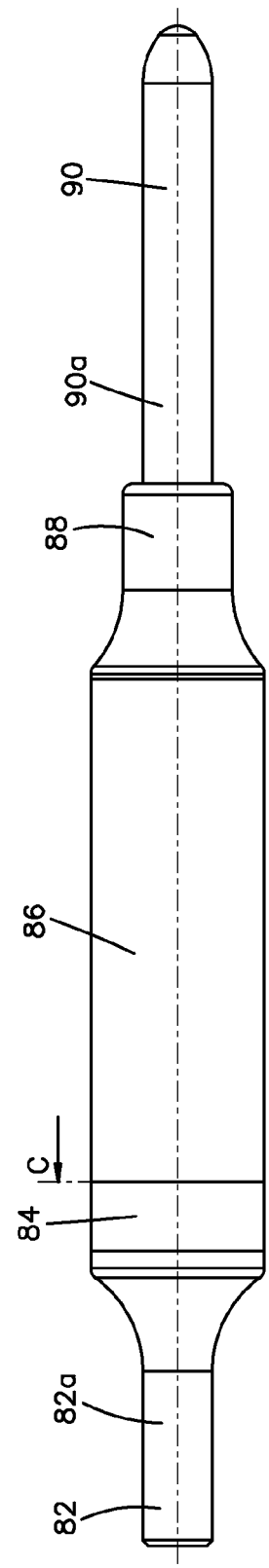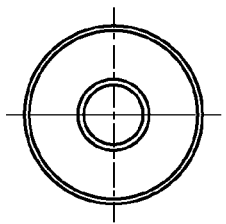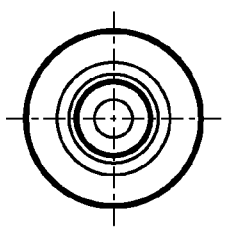

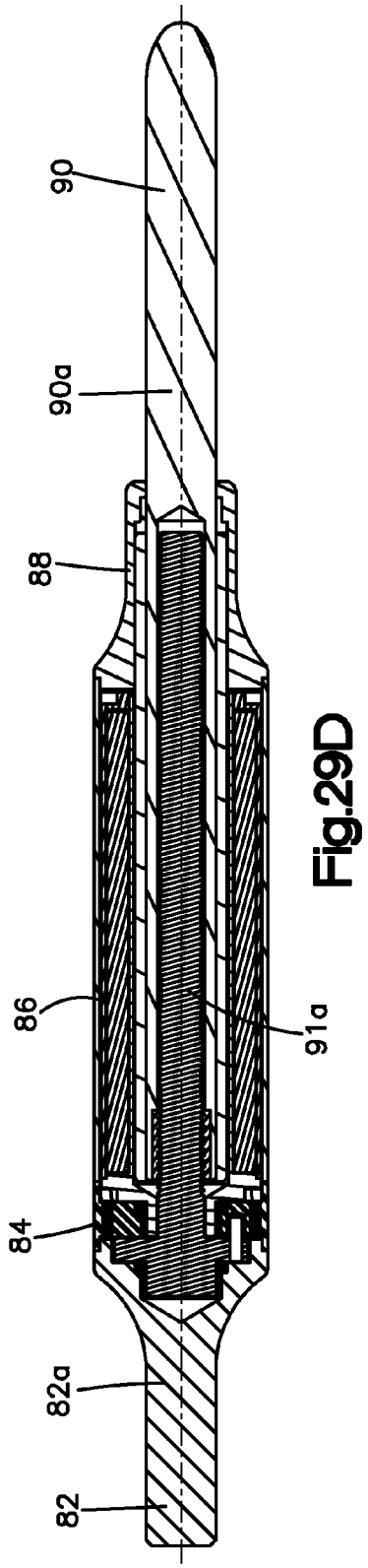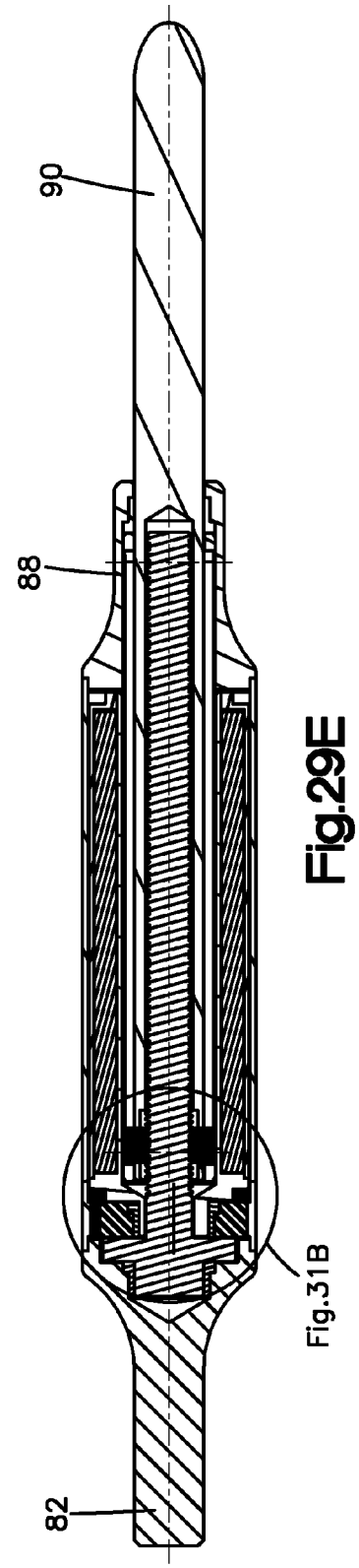

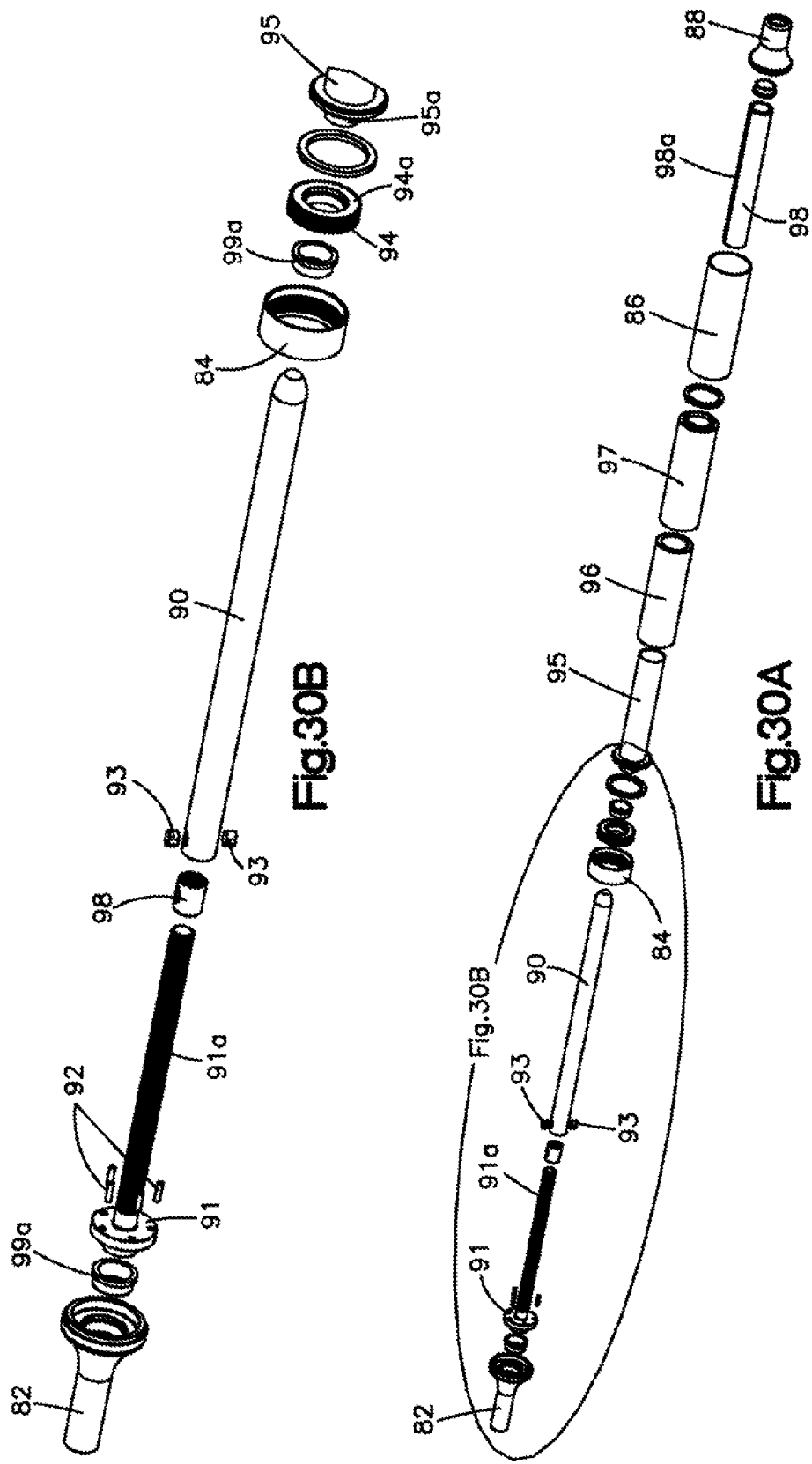

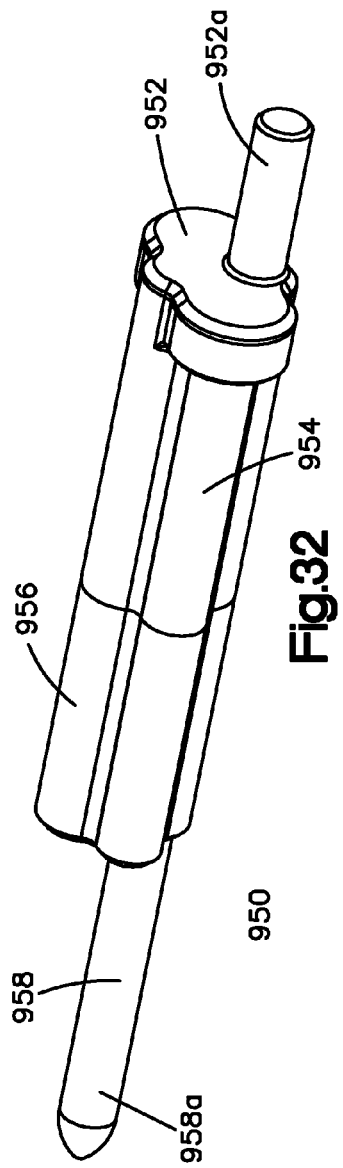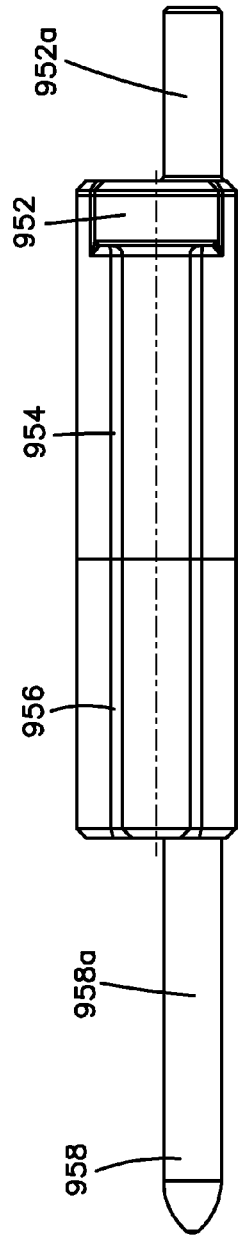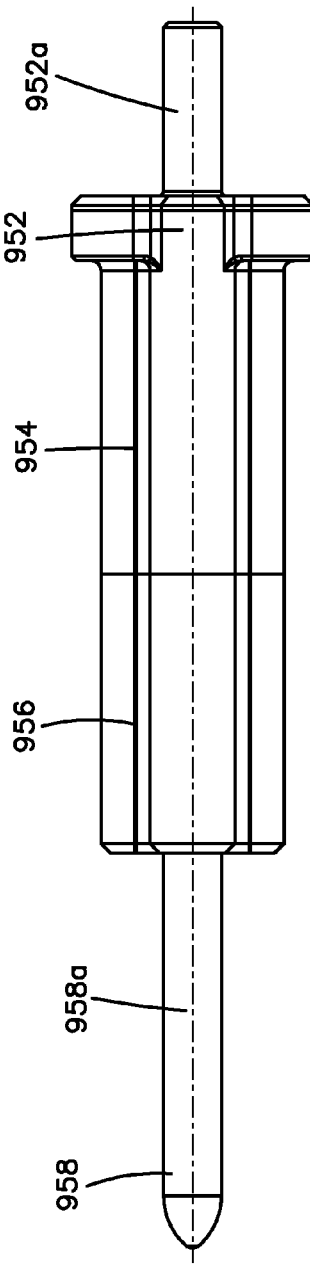

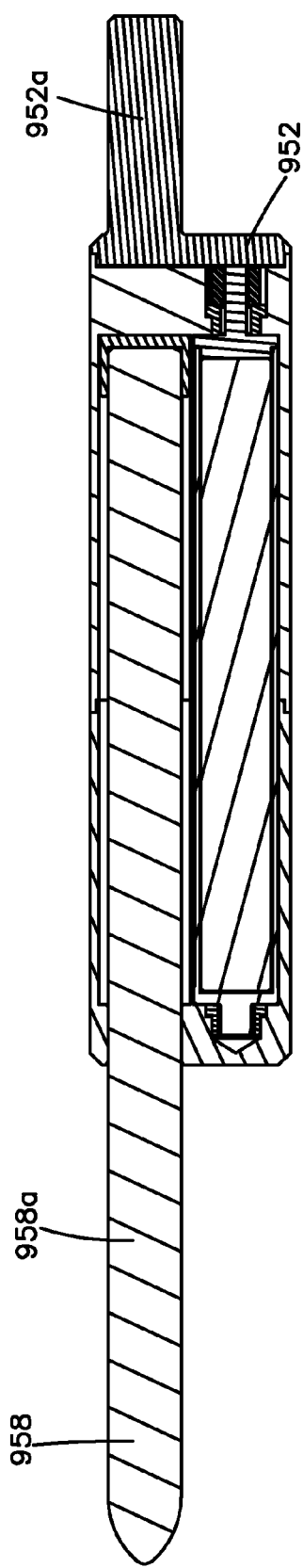
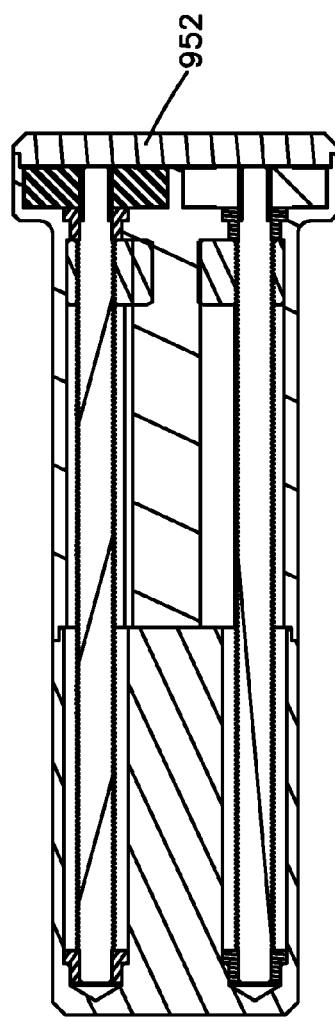
Fig.33C
Fig.33D

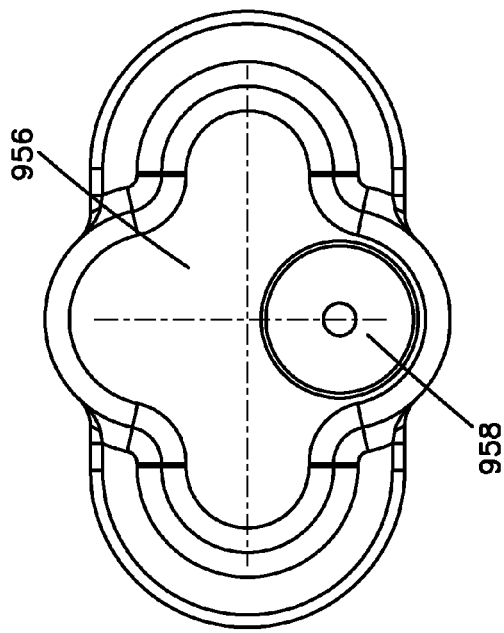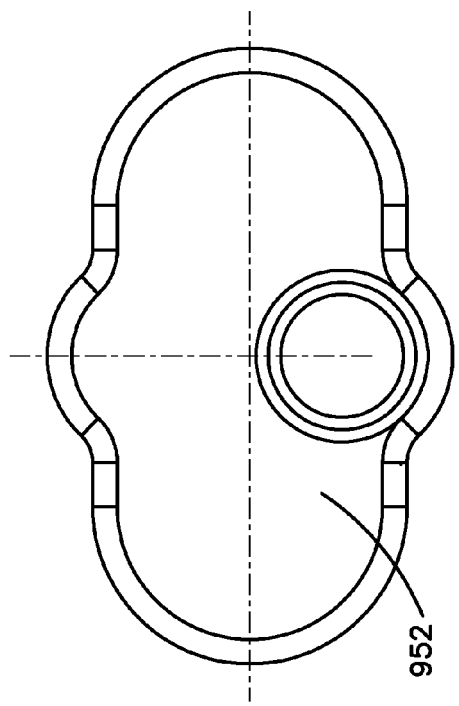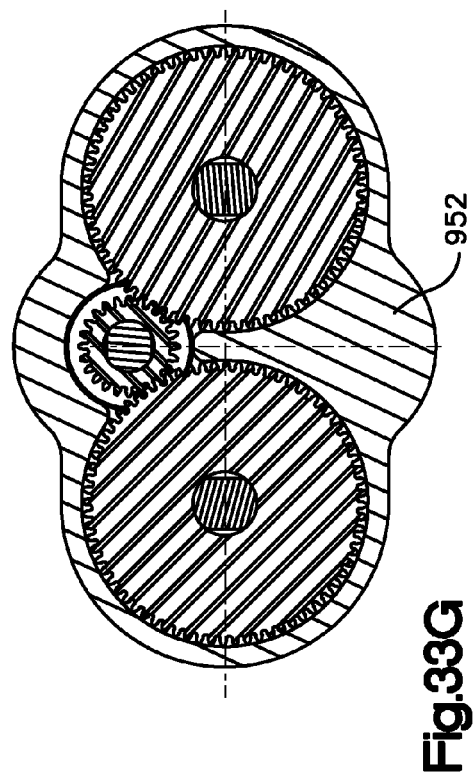

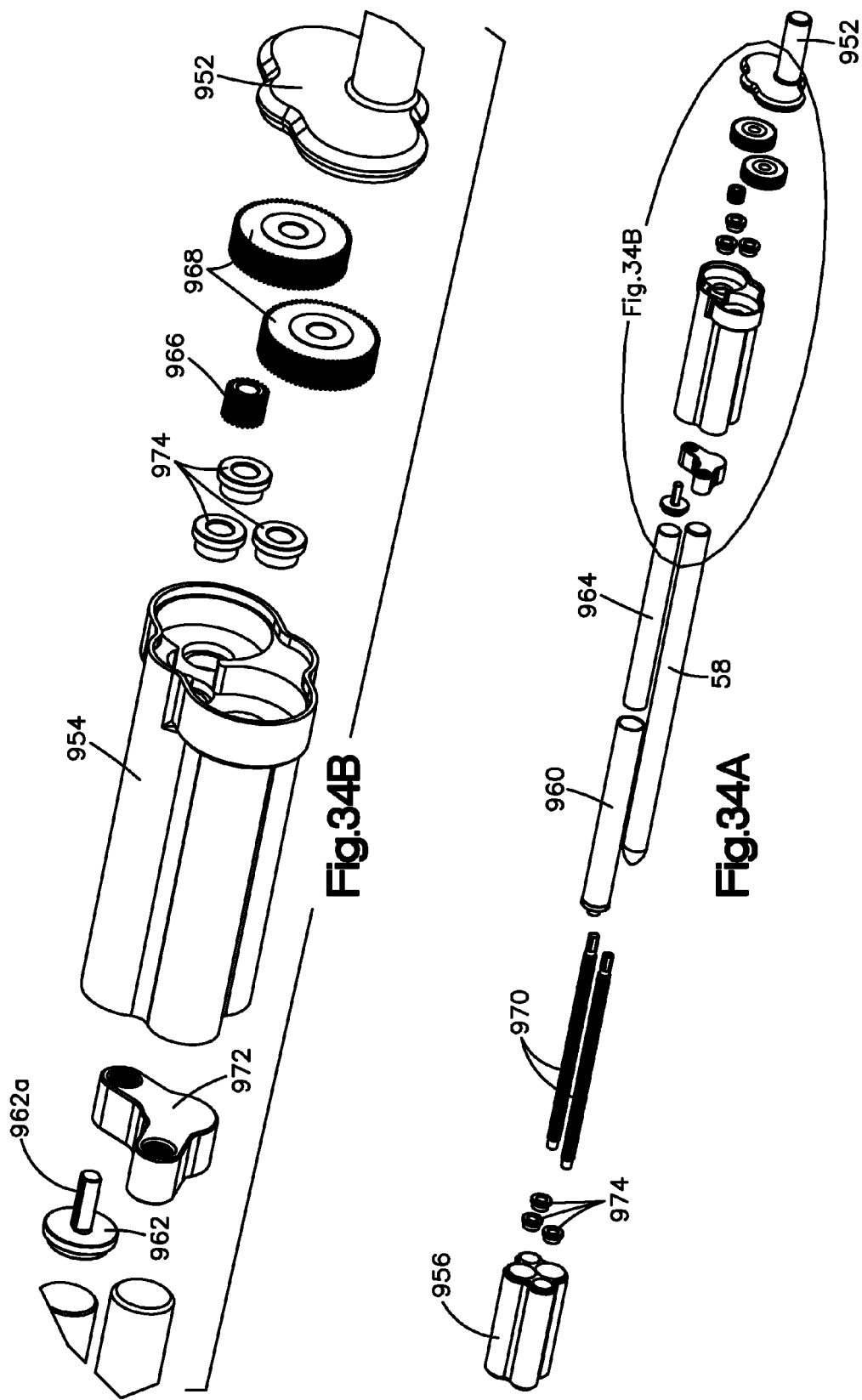

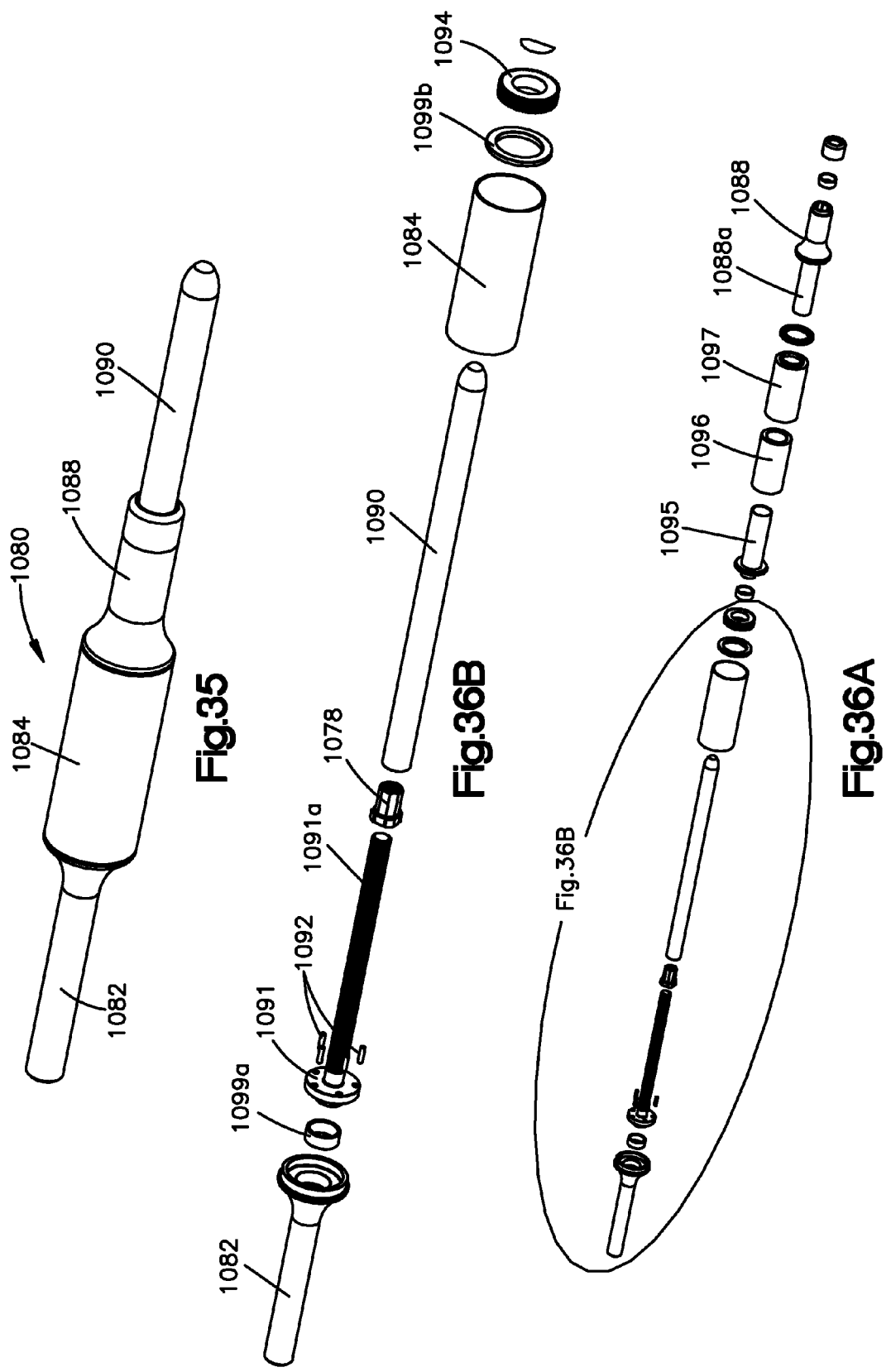

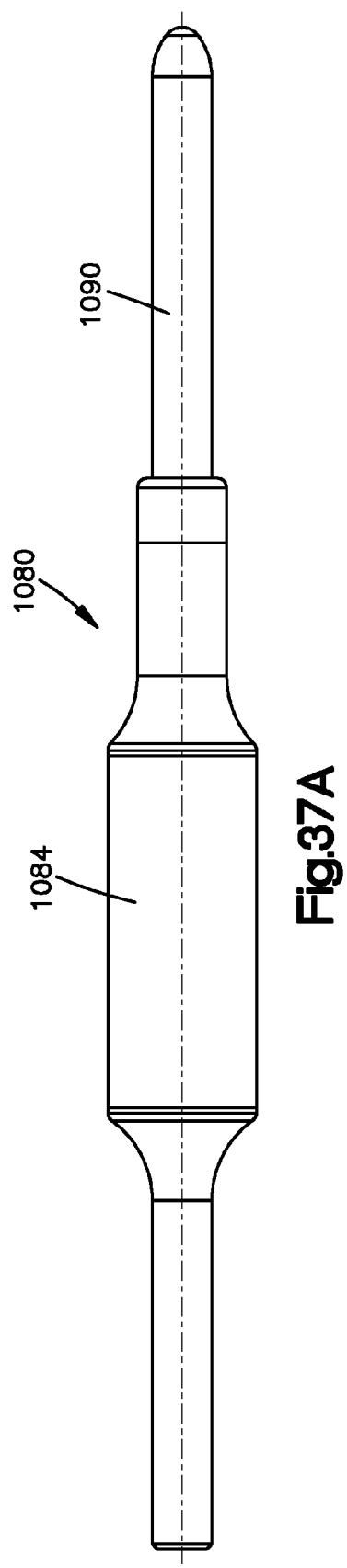
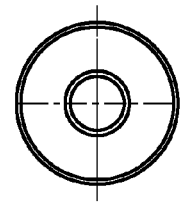
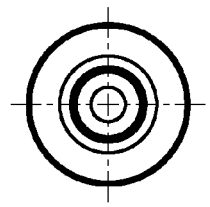
Fig.37A
Fig.37B
Fig.37C

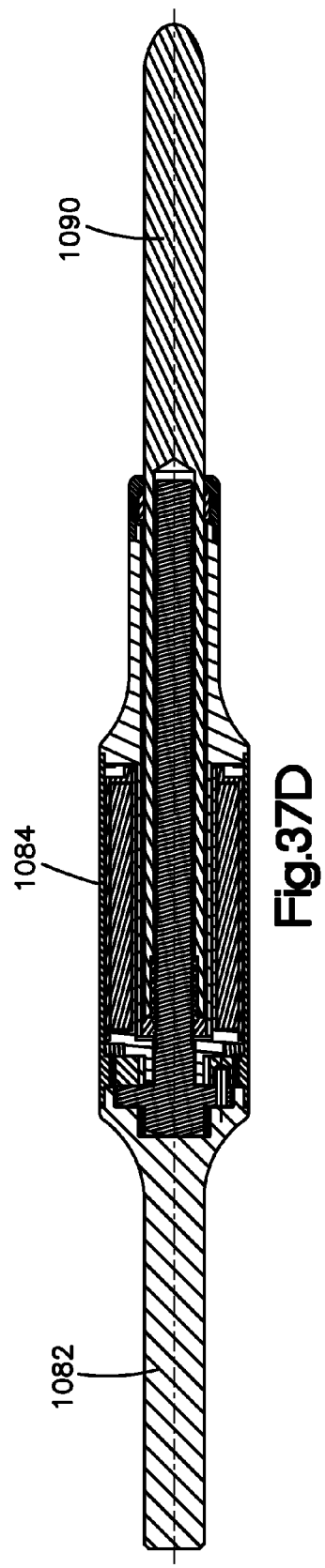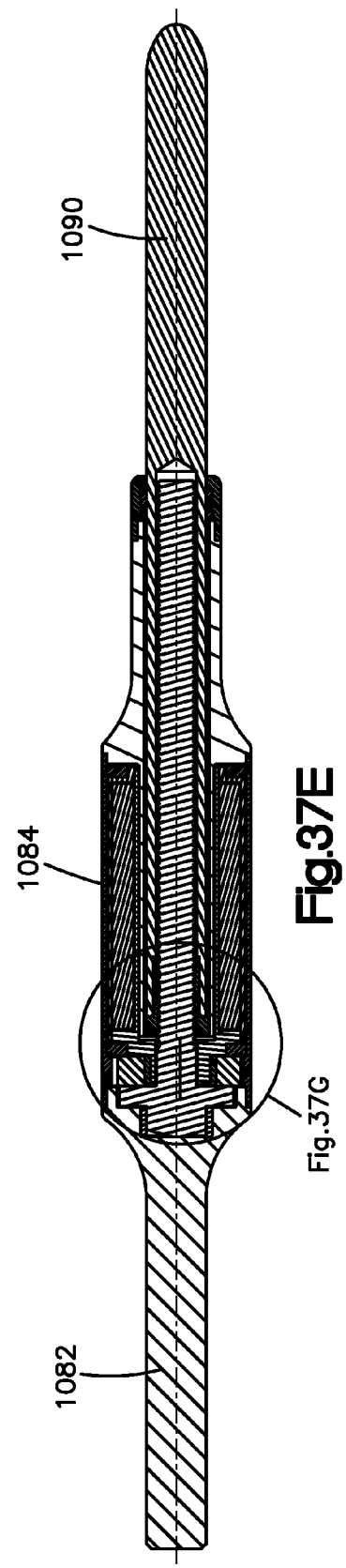

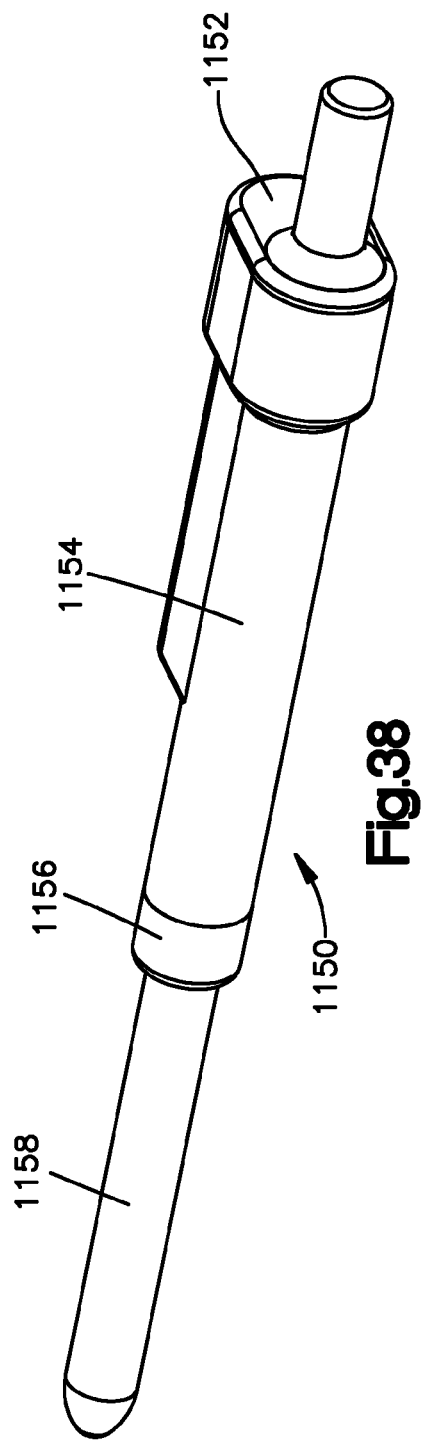
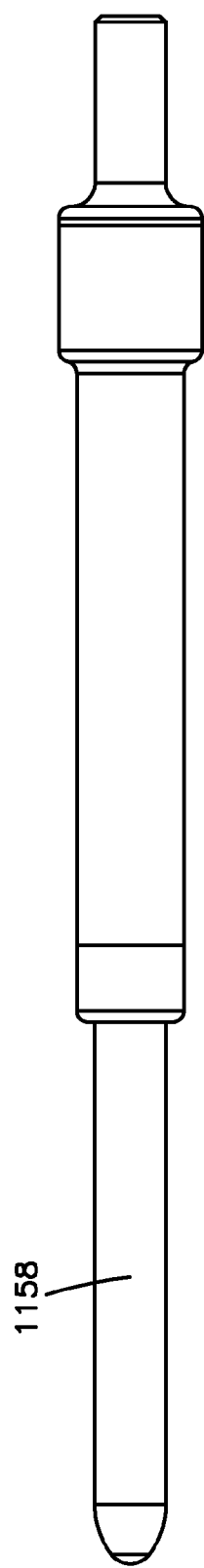
Fig.38
Fig.39A

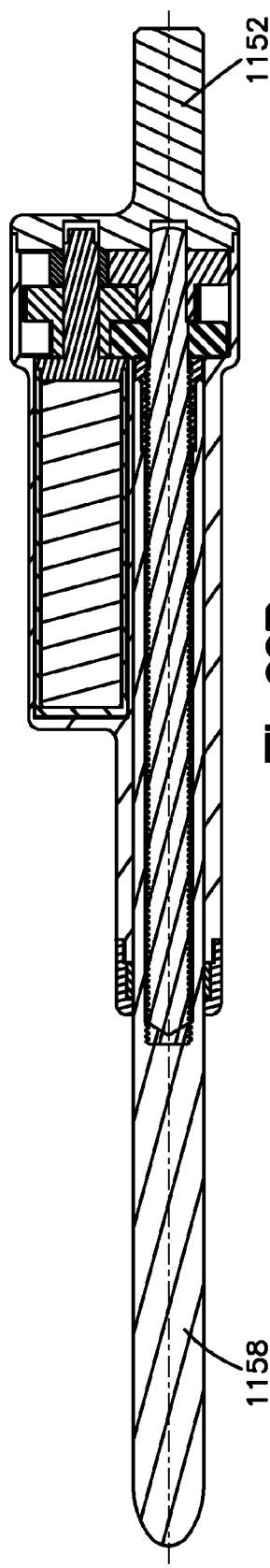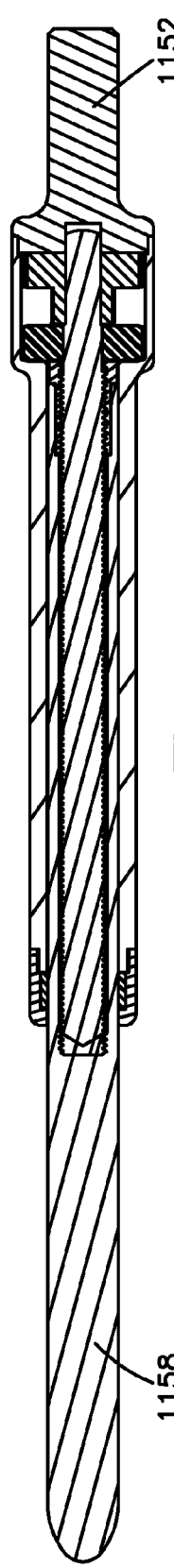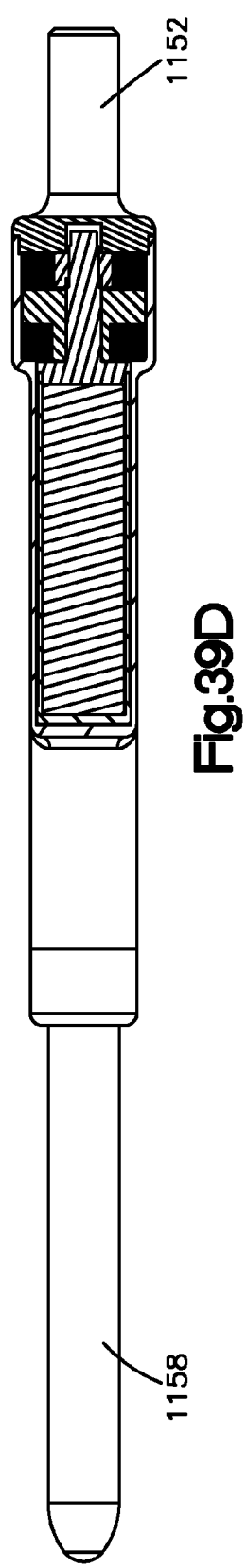

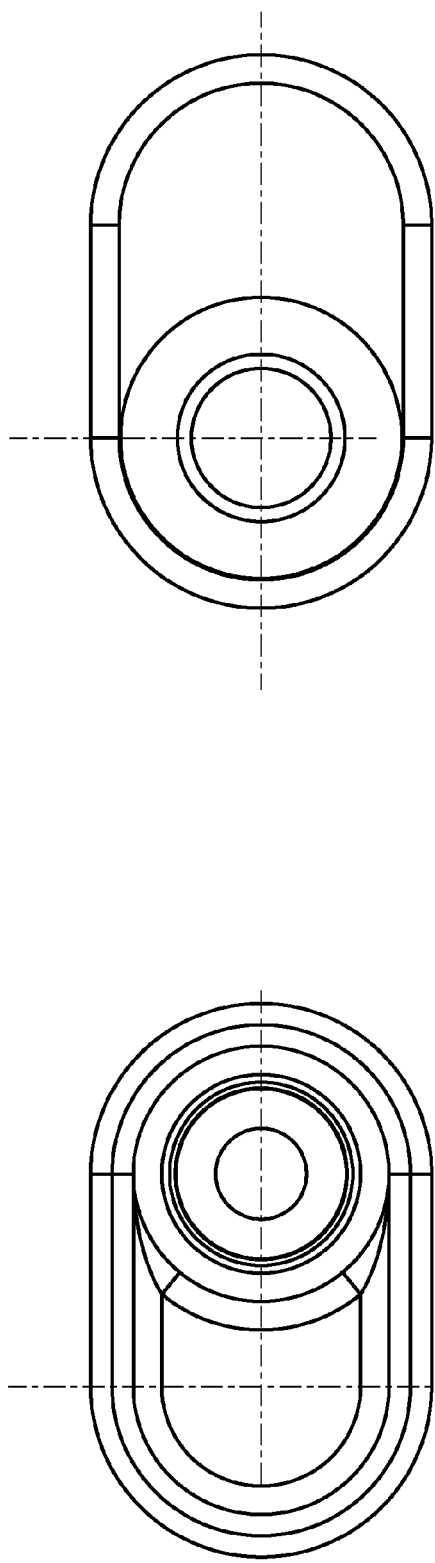

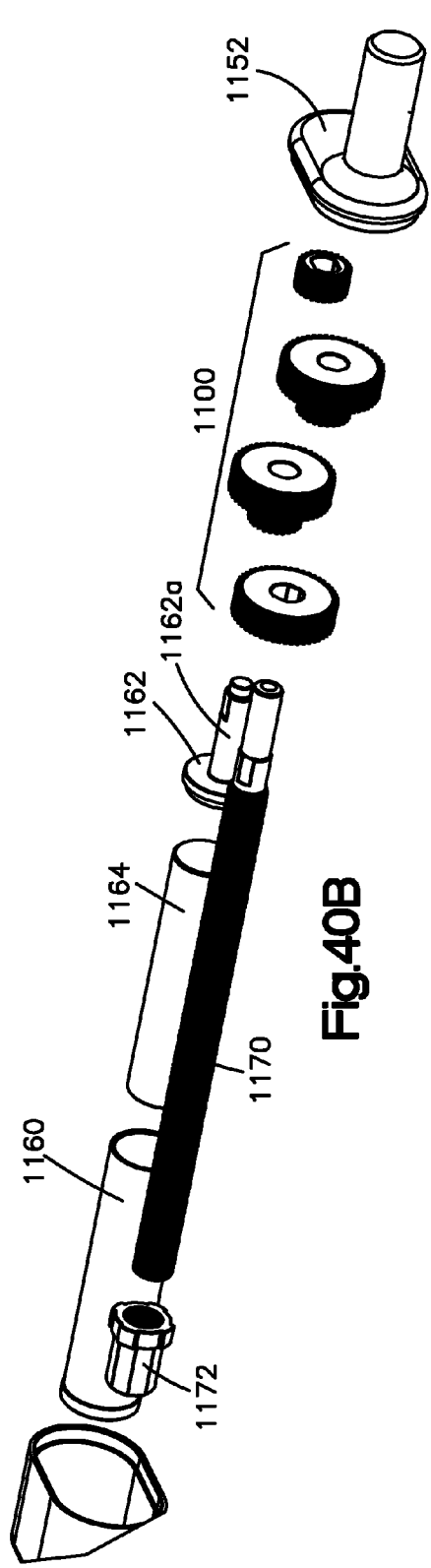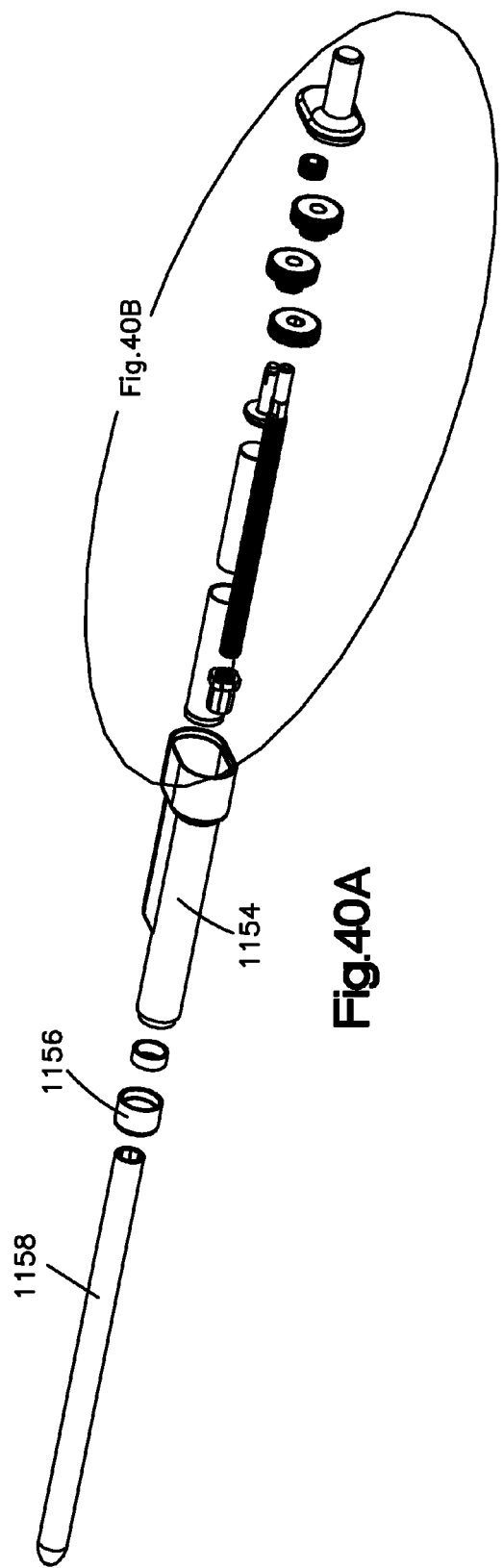

NON-FUSION SCOLIOSIS EXPANDABLE SPINAL ROD

CROSS-REFERENCE TO RELATED APPLICATION

The present disclosure is claims priority to U.S. Patent Application No. 61/265,568, filed Dec. 1, 2009, entitled "Non-Fusion Scoliosis Expandable Spinal Rod," which is incorporated herein by reference in its entirety.

BACKGROUND OF THE DISCLOSURE

Scoliosis is a medical condition where an individual's spine curves off of its anatomical shape, typically in an "S" or "C" shape, and may also be rotated about a vertical axis or a longitudinal axis of the spine. Scoliosis can be a particularly painful and dangerous condition for young persons including infants, juveniles and adolescents, who are not fully grown. Young persons with scoliosis may be treated in various manners depending upon age, severity of the curve and the likelihood of progression of the condition. Conventional options for scoliosis include observation, bracing and surgery.

Surgery is typically indicated for juvenile scoliosis when there is a high likelihood of progression, the curve is causing significant pain and/or the curve is impacting physiological functions, such as breathing. Surgical intervention typically results in fusion of the impacted portion of the spine, which is ideally delayed until the patient is skeletally mature. However, certain severe cases of juvenile scoliosis require surgical intervention prior to skeletal maturity to prevent progression of the curve and/or to stabilize the spine. Multiple surgeries in such cases are common to gradually correct the curvature and/or modify the surgical construct to permit growth or to gradually move the curved or twisted spine.

SUMMARY

The present disclosure relates generally to orthopedics. More specifically, the disclosure relates to a non-fusion scoliosis construct including a magnetically actuated growing rod that permits extension of the rod, growth of the construct and extension or correction of a patient's spine without significantly invasive surgical intervention. The device includes an actively expandable rod that is mounted to a patient's spine or ribs using hooks, screws and/or other fastening mechanisms to be fixed to the posterior of the patient's spine or to nearly any other portion of the patient's spine that permits correction of an undesirable spinal curvature. The system is preferably magnetically activated from outside of the patient's body utilizing a magnetic field without further surgery for expansion. The system is typically indicated for adolescent idiopathic scoliosis, early onset scoliosis and/or thoracic insufficiency syndrome, but is not so limited and may be utilized to treat nearly any type of scoliosis or may be employed in nearly any treatment where extension of a rod mounted within a patient is desirable, without the necessity for invasive surgical intervention.

In accordance with some implementations, there is provided a growing rod for mounting between attachment mechanisms that are secured to anatomical structures of a patient having scoliosis. The growing rod may include a base rod having an attachment end and an extendable rod being translatable relative to the base rod along a longitudinal axis. A housing may enclose at least a portion of the extendable rod and a magnet that is rotatably mounted within the housing. A gear reduction mechanism associated with the magnet and the extendable rod may be provided that reduces an output rotation to the extendable rod in comparison to an input rotation from the magnet.

In accordance with some implementations, there is provided a growing rod that may include a housing, a fixed rod that is attached to the housing at a first end of the housing, and an extendable rod that moves along a longitudinal axis of the growing rod and extending from a second end of the housing. A magnet mounted within the housing may be provided such that movement of the magnet caused by an external magnetic field is input to a gear reduction mechanism. The gear reduction mechanism may reduce the input movement to produce an output that is translated into longitudinal movement of the extendable rod.

In accordance with some implementations, there is provided an expandable spinal growing rod that may include a first rod that is fixedly attached to a housing at a first end of the housing and a second rod that extends from a second end of the housing and that moves along a longitudinal axis. A magnet may be provided within the housing that engages a gear mechanism. Input rotational movement of magnet may drive the gear mechanism, which is translated into longitudinal movement of the second rod relative to the housing.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE SEVERAL VIEWS OF THE DRAWINGS

The foregoing summary, as well as the following detailed description of several implementations of the device and methods of the present application, will be better understood when read in conjunction with the appended drawings. For the purposes of illustrating the growing rod or non-fusion scoliosis expandable spinal rod of the present application, there are shown in the drawings several implementations. It should be understood, however, that the application is not limited to the precise arrangements and instrumentalities shown. In the drawings:

FIGS. 2A-2C illustrate side elevational, front and rear elevational and top plan views of the growing rod of FIG. 1;

FIGS. 3A-3B illustrate cross-sectional views of the growing rod of FIG. 1, taken along lines A-A and B-B of FIGS. 2A and 2B, respectively;

FIGS. 5A-5B illustrate illustrates an exploded view and a magnified exploded view of components taken from within the circle Y of the growing rod of FIG. 4C, respectively;

FIGS. 8A-8E illustrate several plan, elevational and cross-sectional views of the growing rod of FIGS. 7A-7D;

FIGS. 9A-9B illustrate an exploded view and a magnified exploded view of components of the growing rod of FIGS. 7A-7D, respectively;

FIGS. 11A-11E illustrate several plan, elevational and cross-sectional views of the growing rod of FIGS. 10A-10-C;

FIGS. 12A-12B illustrate an exploded and a magnified exploded view of several components of the growing rod of FIGS. 10A-10C;

FIGS. 14A-14E illustrate several plan, elevational and cross-sectional views of the growing rod of FIGS. 13A-13C;

FIGS. 15A-15B illustrate an exploded view and a magnified exploded view of components of the growing rod of FIGS. 13A-13C, respectively;

FIGS. 17A-17E illustrate several plan, elevational and cross-sectional views of the growing rod of FIGS. 16A-16C;

FIGS. 18A-18B illustrate an exploded view and a magnified exploded view of several components taken from the growing rod of FIGS. 16A-16C, respectively;

FIGS. 20A-20H illustrate several plan, elevational and cross-sectional views of the growing rod of FIG. 19;

FIGS. 21A-21D illustrate several operational steps of a mechanism of the growing rod of FIG. 19, shown in a forward bias position;

FIGS. 23A-23B illustrate an exploded view and a magnified exploded view of several components of the growing rod of FIGS. 19 and 20A-20H, respectively;

FIGS. 24A-24E illustrate several views of a ratchet arm of the growing rod of FIGS. 19 and 20A-20H and related components;

FIG. 25 illustrates a top perspective view of a growing rod in accordance with a seventh implementation of the present disclosure;

FIGS. 26A-H illustrate several plan, elevational and cross-sectional views of the growing rod of FIG. 25;

FIGS. 27A-27B illustrate an exploded view and a magnified exploded view of components taken from the growing rod of FIG. 25, respectively;

FIG. 28 illustrates a top perspective view of a growing rod in accordance with an eighth implementation of the present disclosure;

FIGS. 29A-29E illustrate elevational and cross-sectional views of the growing rod of FIG. 28;

FIGS. 30A-30B illustrate an exploded view and a magnified exploded view of components of the growing rod of FIG. 28, respectively;

FIG. 32 illustrates a top perspective view of a growing rod in accordance with a ninth implementation of the present disclosure;

FIGS. 33A-33G illustrate top plan, elevational and cross-sectional views of the growing rod of FIG. 32;

FIGS. 34A-34B illustrate an exploded view and a magnified exploded view of components of the growing rod of FIG. 32;

FIG. 35 illustrates a top perspective view of a growing rod in accordance with a tenth implementation of the present application;

FIGS. 36A-36B illustrate an exploded view and a magnified exploded view of components of the growing rod of FIG. 35, respectively;

FIGS. 37A-37G illustrate elevational, cross-sectional and magnified cross-sectional views of the growing rod of FIG. 35;

FIG. 38 illustrates a top perspective view of a growing rod in accordance with an eleventh implementation of the present disclosure;

FIGS. 39A-39G illustrate elevational and cross-sectional views of the growing rod of FIG. 38; and FIGS. 40A-40B illustrate an exploded view and a magnified exploded view of components taken of the growing rod of FIG. 38.

DETAILED DESCRIPTION

Figure 1:
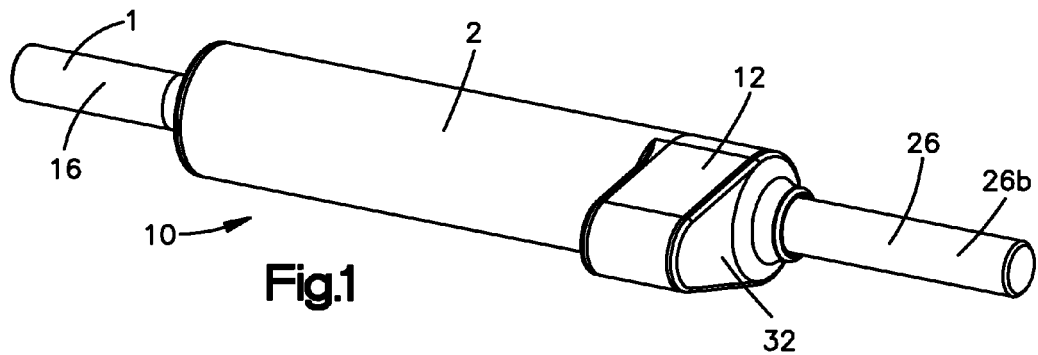
FIG. 1 illustrates a top perspective view of a growing rod or non-fusion scoliosis expandable spinal rod in accordance with a first implementation of the present application.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the several implementations of the non-fusion scoliosis expandable spinal rod and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

Referring to FIGS. 1-6, a growing rod 10 in accordance with a first implementation of the present disclosure includes a base rod 1, a bottom housing 2 sealed and preferably laser welded to the base rod 1, a gear housing 12 preferably laser welded and sealed to the bottom housing 2, a top housing 32 sealed and preferably laser welded to the gear housing 12 and a rod 26 that extends out of the top housing 32 and is slidable relative thereto. The base rod 1 preferably includes a longitudinal slot 1a therein that receives a torque pin 34 mounted to the rod 26 to limit rotational or pivotal movement of the rod 26 relative to the base rod 1. Accordingly, when the base rod 1 is actuated, as will be described in greater detail below, the rod 26 generally translates relative to a longitudinal axis of the growing rod 10 and generally does not pivot or rotate except for the play within the tolerances of the constructs. For de-rotation of the scoliosis, it is also possible to make the longitudinal slot rotating along the axis of the construct to twist the two rods 16/26 against each other.

A magnet 18 is rotatably mounted along the longitudinal axis generally inside the bottom housing 2 and is preferably enclosed by a bottom magnet cover 20 and a top magnet cover 22. The top and bottom magnet covers 20, 22 are preferably laser welded together to seal the magnet 18 therein and are secured to the magnet 18 for rotation therewith along the longitudinal axis. The magnet 18 is preferably diametrically magnetized including at least two polls 18a, 18b and may include multiple pairs of polls (FIG. 6). The bottom magnet cover 20 includes an eccentric end 20a spaced from an attachment end 1b of the base rod 1.

Figure 1A:
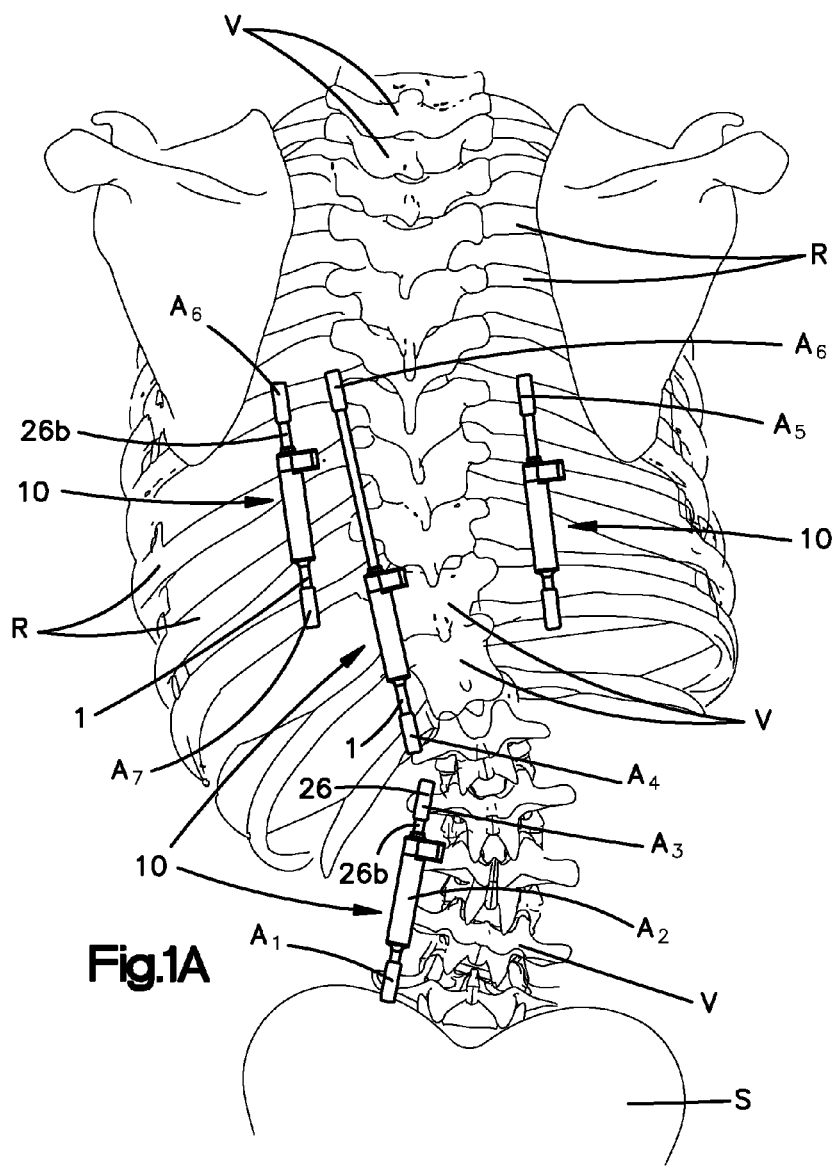
FIG. 1A illustrates a posterior view of a spine with several of the growing rods of FIG. 1 mounted thereto.
Figure 4A:
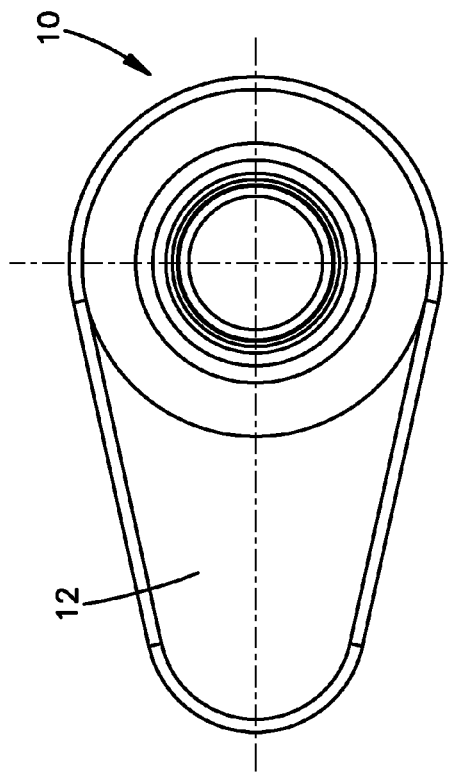
FIGS. 4A-4C illustrate various cross-sectional and a rear elevational view of the growing rod of FIG. 1.
Figure 4C:
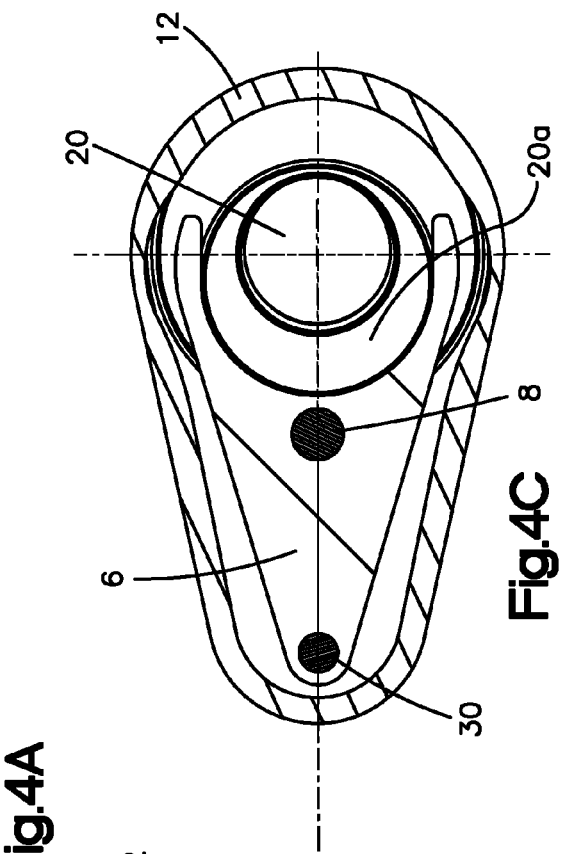
Figure 4B:
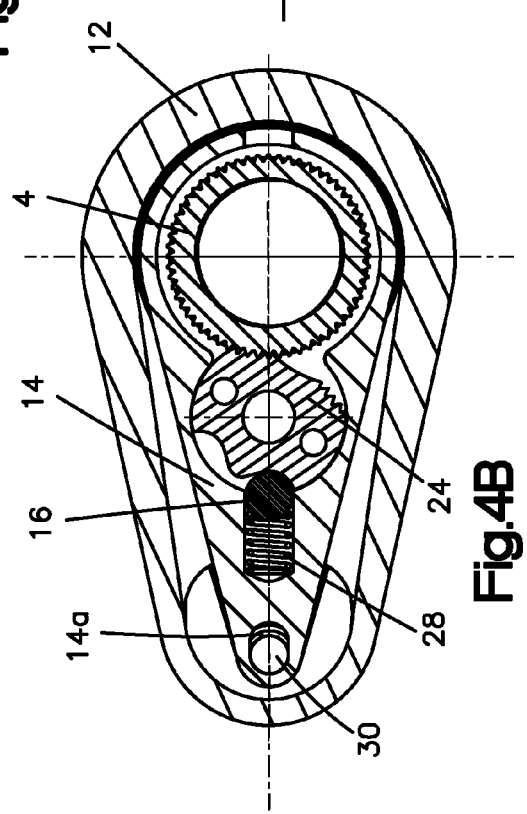
Figure 6A:
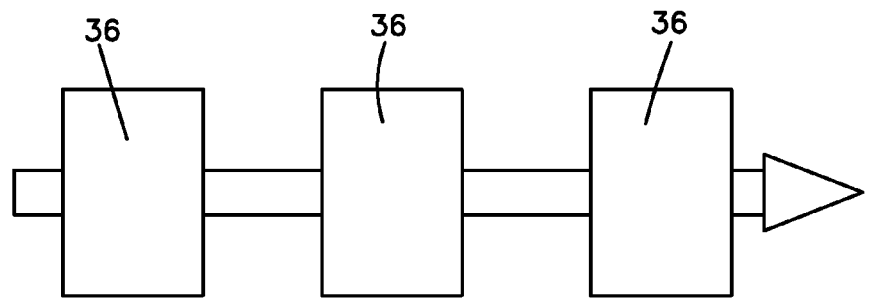
FIGS. 6A-6D illustrate several views of magnetic activation of a magnet of the growing rod of FIG. 1.
Figure 6B:
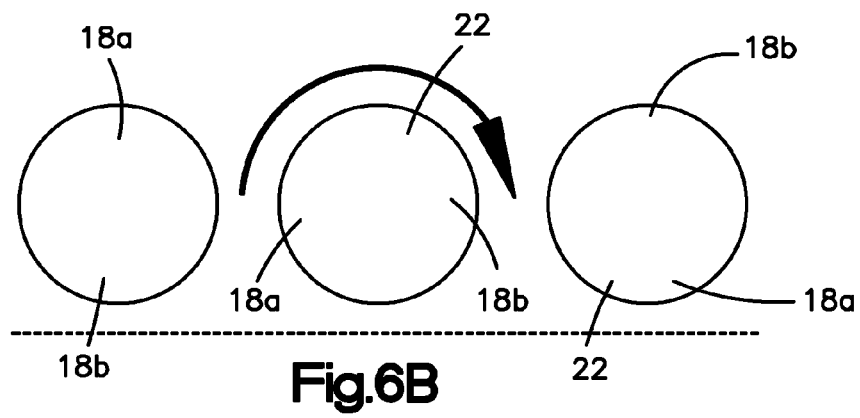
Figure 6C:
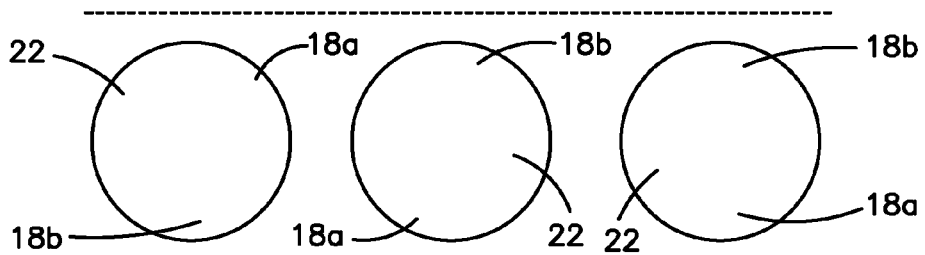
Figure 6D:
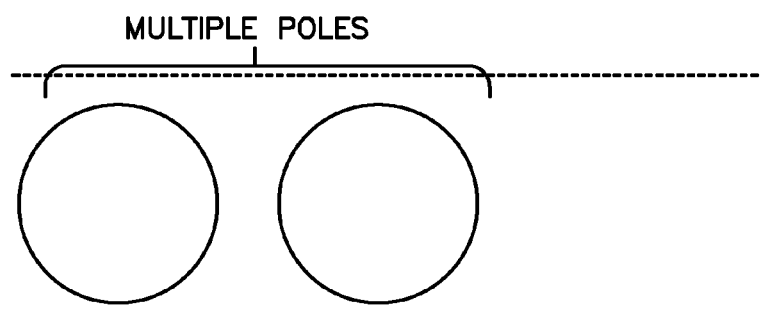
Figure 7A:
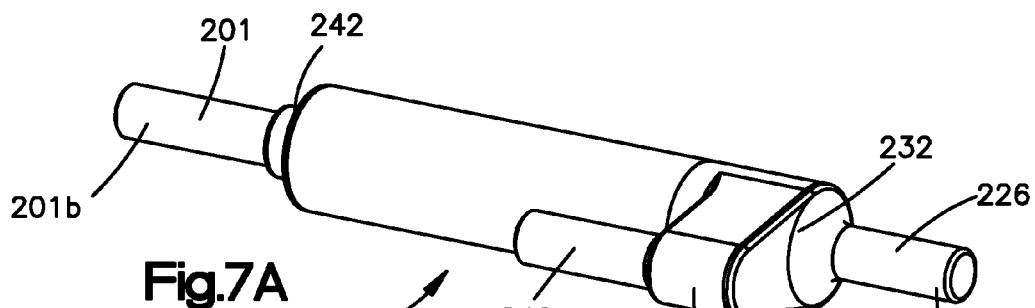
FIGS. 7A-7D illustrate a top perspective view of a growing rod in accordance with a second implementation of the present disclosure.
Figure 7B:
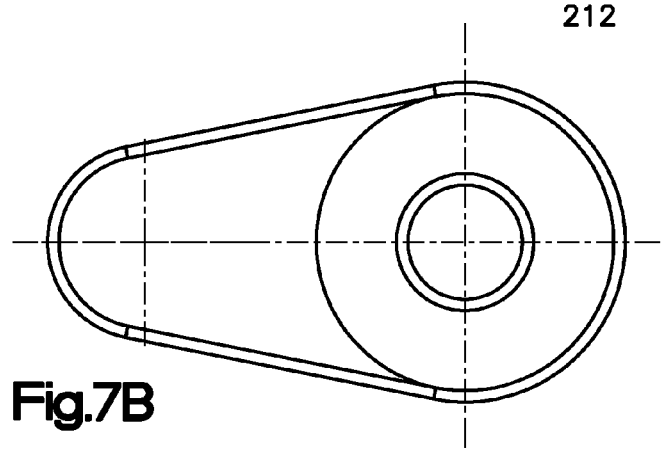
Figure 7C:
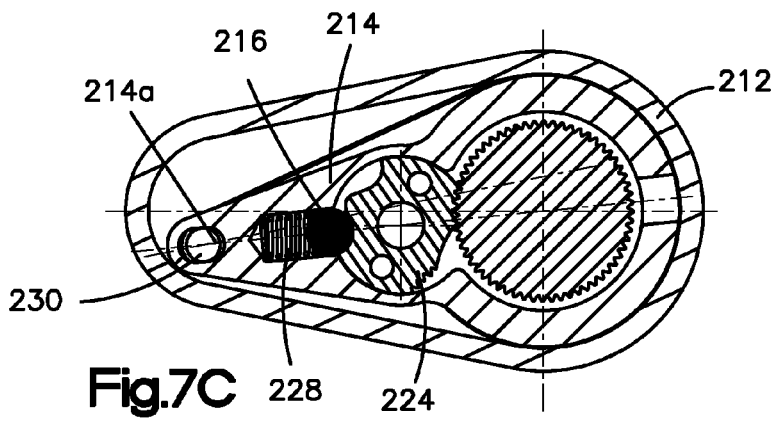
Figure 7D:
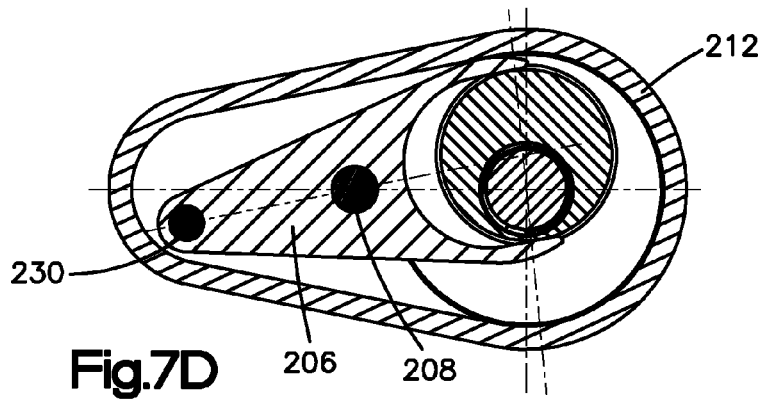

The base rod 1 and the rod 26 include attachment ends 1b, 26b that are utilized to attach the growing rod 10 to attachment points or mechanisms $A_1$-$A_8$ (FIG. 1A), such as a pedicle screw $A_1$-$A_6$, a hook, a cradle $A_7$-$A_8$ or other attachment mechanisms that permits the surgeon to mount the growing rod 10 to the patient's body. The attachment points or mechanisms $A_1$-$A_8$ are preferably mounted to bony structures of the patient's anatomy, such as vertebra V, ribs R, the sacrum S, long bones or other relatively strong, stiff structures of the patient's anatomy A gear reduction mechanism that drives the rod 26 to translate relative to the base rod 1 when the magnet 18 is actuated to rotate is generally positioned within the gear housing 12. The gear reduction mechanism of the first implementation includes a carrier gear 4, a fork 6, a fork pin 8 pivotally mounting the fork 6 to the gear housing 12, a ratchet arm 14 that is pivotal within the gear housing 12 about the fork pin 8 and a pawl 24 that is mounted within the ratchet arm 14. The carrier gear 4 includes external gear teeth 4a that interact with pawl teeth 24a of the pawl 24 and internal gear teeth 4b that interact with the threads 26a on the rod 26.

A majority of the components of the growing rod 10 of the first implementation, with the exception of the magnet 18 are constructed of a titanium or titanium alloy material. However, the components of the growing rod 10 are not limited to constructions utilizing titanium or titanium alloy material and may be constructed of a cobalt-chromium material, a polymeric material or nearly any material that is preferably non-magnetizable, is generally stiff and strong, is biocompatible, is able to take on the general size and shape of the respective components and is able to withstand the normal operating conditions of the growing rod. The magnet 18 is preferably constructed of a permanent magnet or a magnetized material that is able to hold the magnetization during normal operating conditions. The components and magnet of the remaining several implementations, which will be described in greater detail below, are also preferably constructed of similar materials, unless otherwise indicated.

In use, in the first implementation, the assembled growing rod 10 is positioned in a patient's body through a surgical incision. A surgeon mounts attachment points $A_1$-$A_8$ to the patient's body at positions that the surgeon intends to extend away from each other, such as vertebra V in a scoliotic spine, the sacrum S, ribs R or other relatively solid, boney structure that is appropriate for fixation. Once the attachment positions and mechanisms $A_1$-$A_8$ are selected, mounted and contoured to the patient's body/anatomy, the attachment mechanisms $A_1$-$A_8$ are engaged with the attachment ends 1b, 26b of the base rod 1 and rod 26, respectively. The incision is subsequently closed. Over a period of time, a magnetic field is passed over, via translation or rotation outside of the patient's body, in proximity to the growing rod 10, thereby causing the magnet 18 to rotate about the longitudinal axis. Rotation of the magnet 18 around the longitudinal axis causes the rod 26 to extend away from the base rod 1 and the attachments $A_1$-$A_8$ to the patient's anatomy to extend away from each other. The movement of the growing rod 10 for each application of the external magnet or magnetic field to the magnet 18 is preferably small such that the patient's anatomy is able to adapt to the gradual movement. Specifically, the patient's soft tissue and boney structure generally are able to adapt to the small movements to correct the anatomy. The extensions of the growing rod 10 are preferably applied over a period of months or years and preferably eliminate the need to invasively create an incision following an initial surgery to extend the growing rod 10, as the growing rod 10 of the first implementation is able to extend by applying the external magnet or magnetic field.

In use, each translational pass of an external magnet 36 proximate to the growing rod 10 or each application of an external magnetic field causes the magnet 18 to rotate about the longitudinal axis approximately one hundred eighty degrees (180°) (depending on they play in between mating parts, could vary ±40°). The growing rod 10 is not limited to being actuated by translational movement of the external magnet 36 and may be actuated by rotation of the external magnet 36 proximate to the growing rod 10 or by otherwise applying an external magnetic field to the growing rod 10.

When the magnet 18 of the growing rod 10 of the first implementation is actuated to rotate, the top and bottom magnet covers 22, 20 rotate with the magnet 18 about the longitudinal axis. The eccentric end 20a of the bottom magnet cover 20 is engaged with the fork 6 and causes the fork 6 to pivot about the fork pin 8. Pivoting of the fork 6 about the fork pin 8 drives an arcuate translation or pivoting movement of a tappet 30, which is fixed to an end of the fork 6 opposite the eccentric end 20a within the gear housing 12. The generally up and down arcuate translational movement of the tappet 30 drives a pivoting movement of the ratchet arm 14 about the fork pin 8. This pivoting movement is driven by engagement of the tappet 30 in an oblong hole 14a of the ratchet arm 14, within which the tappet 30 slides. This pivoting movement of the ratchet arm 14 drives the pawl 24 to pivot the carrier gear 4 about the longitudinal axis or the pawl 4 or to slip relative to the carrier gear 4 wherein the pawl teeth 24a jump over the external teeth 4a of the carrier gear 4. That is, the carrier gear 4 is rotatable in only one direction depending upon which pawl groove 24b a locking ball 16 is positioned. The locking ball 16 is urged into the selected pawl groove 24b by a biasing spring 28, which allows the pawl 24 to slip relative to the carrier gear 4 when attempting to urge the carrier gear 4 in a rotation direction that the carrier gear 4 is locked against rotating in. Accordingly, for every rotation of the magnet 18, the pawl 24 only urges the carrier gear 4 to rotate in any single one hundred eighty degree (180°) portion of the rotation and slips relative to the carrier gear 4 during the remainder of the one hundred eighty degree (180°) portion of the rotation. When the pawl 24 is urging the carrier gear 4 in the non-blocked rotation direction, the internal gear teeth 4b of the carrier gear 4 engage the threads 26a on the rod 26 to cause the rod 26 to translate relative to the base rod 1. Preferably, the rod 26 translates away from the base rod 1, but is not so limited. Specifically, the pawl 24 may be arranged such that the locking ball 16 is positioned in a pawl groove 24b that causes the pawl 24 to engage and drive the carrier gear 4 in a reversed direction. If the growing rod 10 is arranged to reverse, the actuation of the magnet 18 results in the rod 26 translating toward the base rod 1 when the magnet 18 is actuated or to reduce in length when actuated by the external magnet 36.

Referring to FIGS. 7-9, in a second implementation, the growing rod 210 operates in a similar manner to the above-described first implementation of the growing rod 10. Similar reference numerals are utilized to identify similar components of the second implementation and a prefix "2" is utilized to identify the specific components of the second implementation. Differences of the second implementation of the growing rod 210 are described below in comparison to the first implementation.

In the second implementation, the rod 226 is integrally formed with the top housing 232 and is fixed relative to the bottom housing 202 and the gear housing 212. In addition, the carrier gear 204 includes a longitudinally extending shaft 203 with external threads as opposed to the internal gear teeth 4b described in the first implementation of the growing rod 10. In addition, the growing rod 210 of the second implementation includes a top lid 242 with a slot 242a extending longitudinally along the longitudinal axis. The top lid 242 is preferably laser welded to the bottom housing 202 and the base rod 201 is slidably mounted within the top lid 242 along the longitudinal axis. Torque pins 234 are secured to the base rod 201 that engage the slot 242a of the top lid 242 to urge the base rod 201 to translate along the longitudinal axis without rotating relative thereto. The base rod 201 includes internal threads that engage the external threads of the shaft 203 of the carrier gear 204. Accordingly, when the pawl 224 drives rotation of the carrier gear 204, the external threads on the shaft 203 engage and drive the translational movement of the base rod 201 out of the top lid 242.

The growing rod 210 of the second implementation also includes a third attachment 240 extending from the gear housing 212. The third attachment 240 is generally offset and substantially parallel to the longitudinal axis and is utilized as an alternative attachment for mounting to attachment mechanisms $A_1$-$A_8$ that are attached to the patient's anatomy. The third attachment 240 is preferably utilized with attachment mechanisms $A_1$-$A_8$ that are attached to the patient's anatomy offset from a longitudinal axis of the growing rod 210 and is preferably utilized when the attachment end 226b of the rod 226 is not utilized. In use, it is preferred that the attachment end 226b of the rod 226 or the third attachment 240 that is not utilized is cut off of the growing rod 240.

In use, the growing rod 210 of the second implementation is utilized in a similar manner to the growing rod 10 of the first implementation. However, upon actuation of the magnet 218, when the pawl 224 engages and drives rotation of the carrier gear 204 about the longitudinal axis, the threaded shaft 203 engages and drives internal gears within the base rod 201. This driving of the base rod 201 urges the base rod 201 out of the top lid 242 such that the attachment end 201b of the base rod 201 extends away from the attachment 226b of the rod 226 to gradually move the associated attachment points or mechanisms $A_1$-$A_8$ in the patient's anatomy. Sealing of the base rod 201 relative to the top lid 224 occurs between an internal diameter of the top lid 224 and a generally smooth, circular surface of the base rod 201. Accordingly, such sealing may be advantageous as the surface of the base rod 201 is generally circular, smooth and continuous nearly from end to end. In contrast, the rod 26 of the first implementation includes external threads that will eventually extend out of the top housing and may create difficulty for sealing purposes.

Figure 10A:
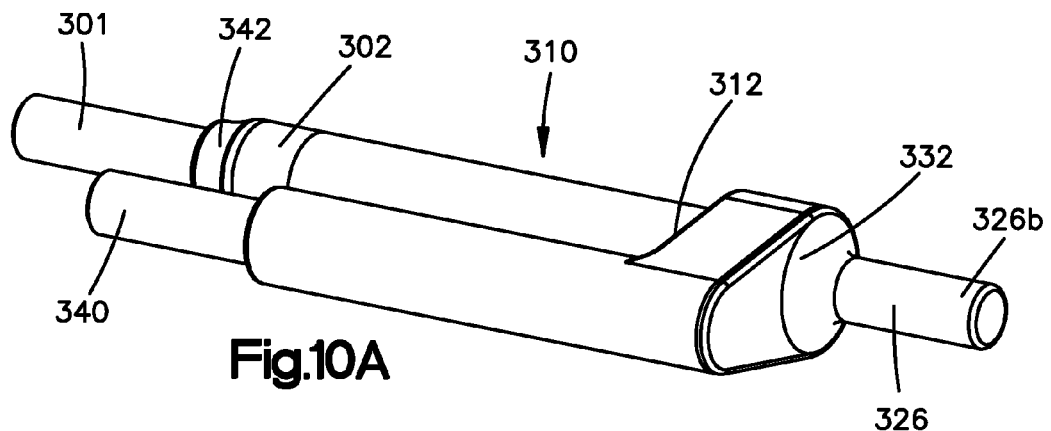
FIGS. 10A-10C illustrate a top perspective view of a growing rod in accordance with a third implementation of the present disclosure.
Figure 10B:
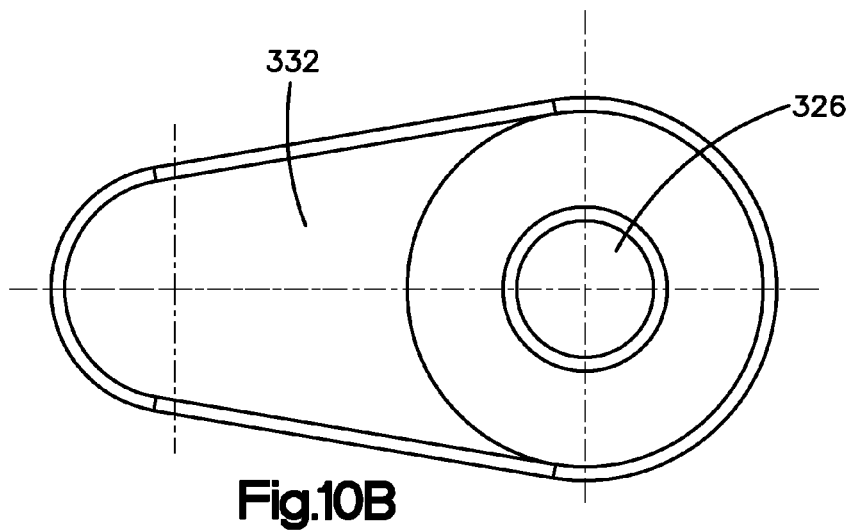
Figure 10C:
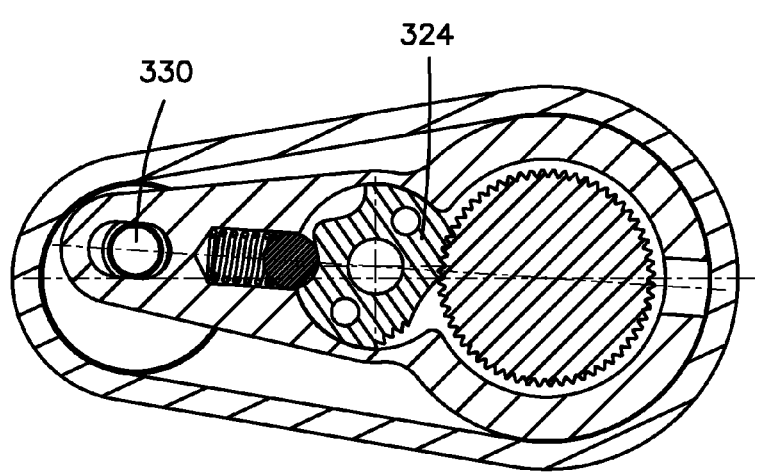

Referring to FIGS. 10-12, in a third implementation, a growing rod 310 operates in a similar manner to the above-described first and second implementation of the growing rod 10, 210. The similar reference numerals are utilized to identify similar components of the third implementation and a prefix "3" is utilized to identify the specific components of the third implementation. Differences of the third implementation of the growing rod 310 are described below in comparison to the first and second implementation. In the third implementation, the magnet 318 and top and bottom magnet covers 320, 322 are offset along a magnet axis that is generally parallel to the longitudinal axis of the growing rod 310. The magnet 318 and top and bottom magnet covers 322, 320 are housed within the gear housing 312 and the tappet 330 is mounted to the bottom magnet cover 320 to directly drive the ratchet arm 314. Accordingly, in the third implementation, the forks 6, 206 of the first and second implementations are eliminated from the assembly.

In operation, actuation of the magnet 318 by an external magnetic field causes the magnet 318 and associated top and bottom magnet covers 322, 320 to rotate about the offset magnet axis. This rotation causes the tappet 330 on the end of the bottom magnet cover 320 to actuate the pivoting movement of the ratchet arm 314 via engagement of the tappet 330 in the oblong hold 314a of the ratchet arm 314. This rotation subsequently causes the base rod 301 to move away from the rod 326 as a result of rotation of the shaft 303.

Figure 13A:
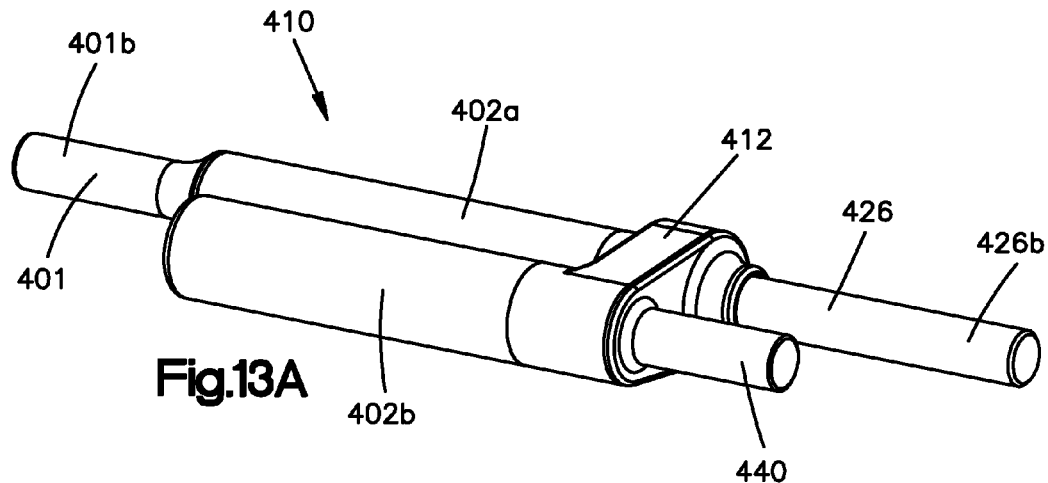
FIGS. 13A-13C illustrate a top perspective view of a growing rod in accordance with a fourth implementation of the present disclosure.
Figure 13B:
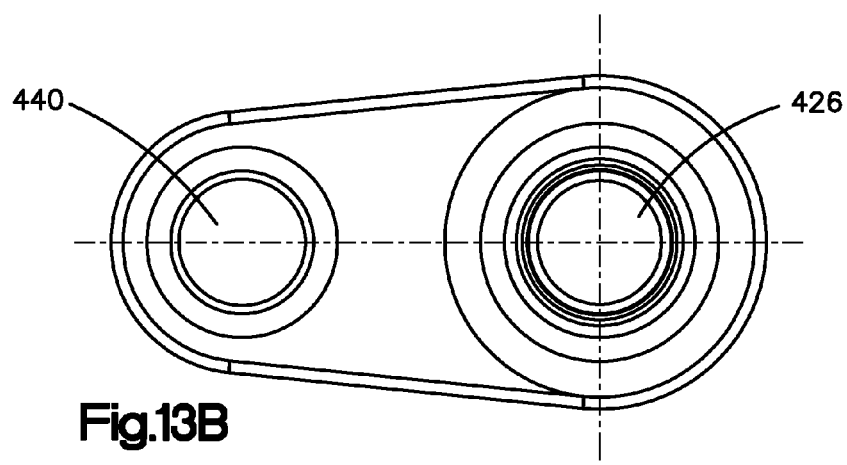
Figure 13C:
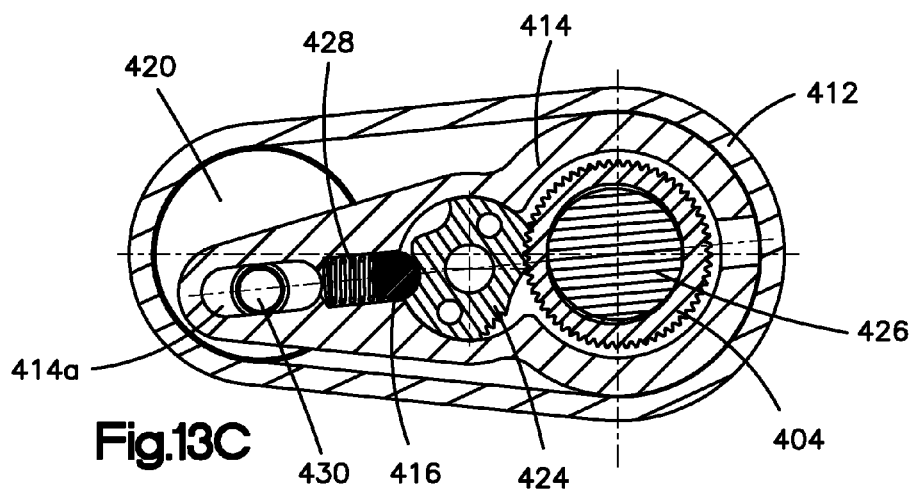

Referring to FIGS. 13-15, in a fourth implementation, a growing rod 410 is substantially similar and includes similar components to the above-described implementations of the growing rods 10, 210, 310 of the first, second and third implementations. The details of each of the components of the fourth implementation of the growing rod 410 are not described herein in detail but only the components that are different than the above-described components of the first, second and third implementations are detailed. Similar reference numerals are utilized to identify the same or similar components and a prefix "4" is utilized to specifically identify components and elements of the fourth implementation of the growing rod 410.

The growing rod of 410 of the fourth implementation is similar to the growing rod 310 of the third implementation with the exception that the rod 426 is translatable along the longitudinal axis with respect to the base rod 401, which is fixed to first and second components 402a, 402b of the bottom housing 402. In use, the growing rod 410 of the fourth implementation operates in a manner that would be apparent to one having ordinary skill in the art based upon the description of the first and third implementations of the growing rod 10, 310 and a review of attached FIGS. 13-15 showing the components of the growing rod 410 of the fourth implementation.

Figure 16A:
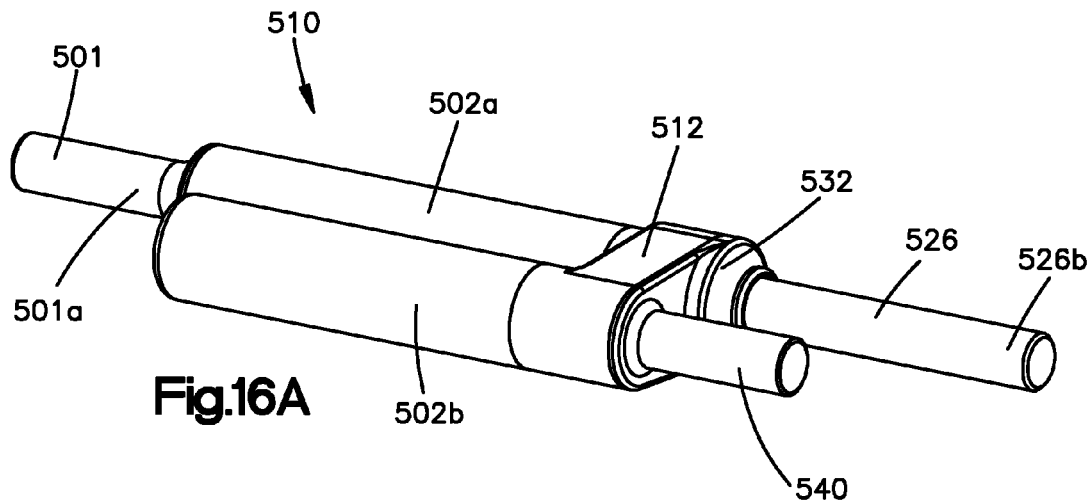
FIGS. 16A-16C illustrate a top perspective view of a growing rod in accordance with a fifth implementation of the present disclosure.
Figure 16B:
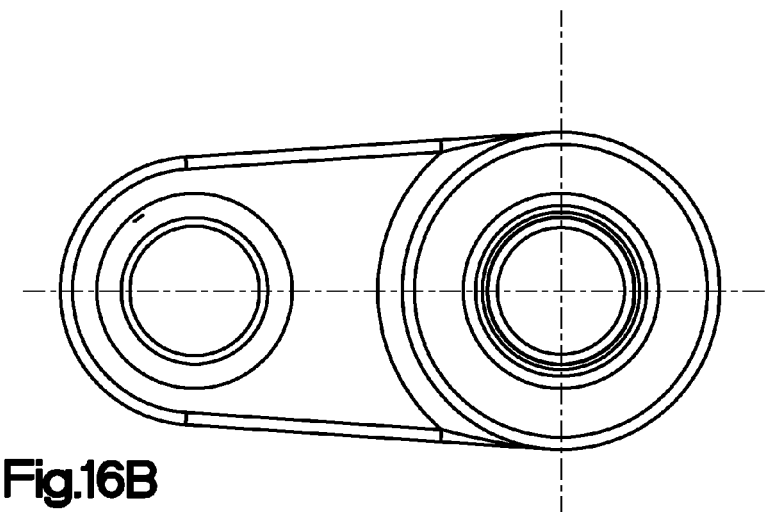
Figure 16C:
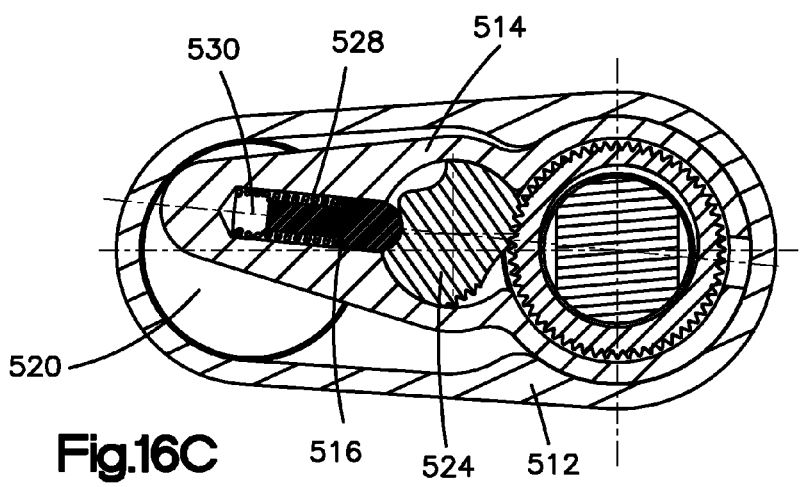
Figure 19:
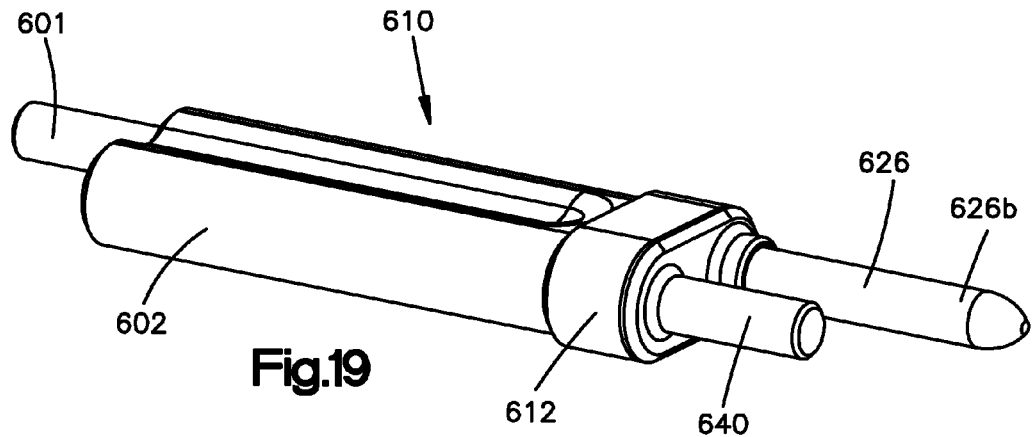
FIG. 19 illustrates a top perspective view of a growing rod in accordance with a sixth implementation of the present disclosure.
Figure 20A:
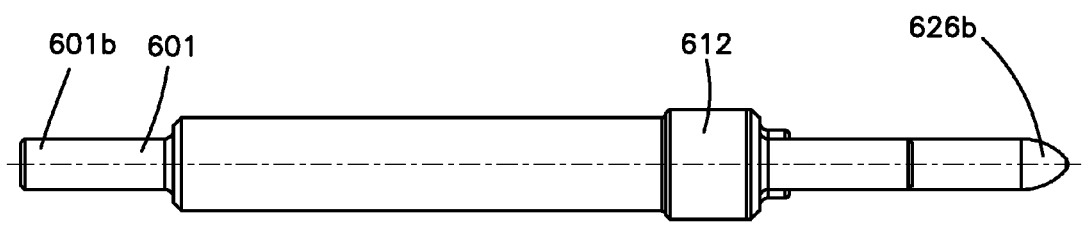
Figure 20B:
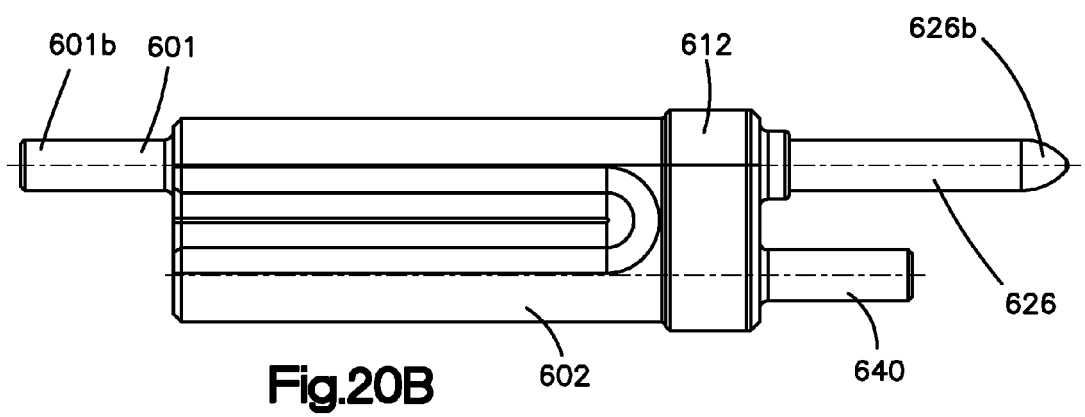
Figure 22A:
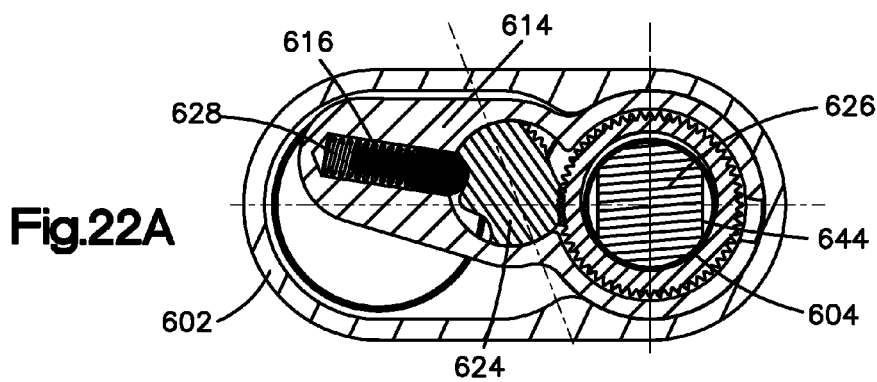
FIGS. 22A-22D illustrate several operational steps of a mechanism of the growing rod of FIG. 19, shown in a reverse bias position.
Figure 22B:
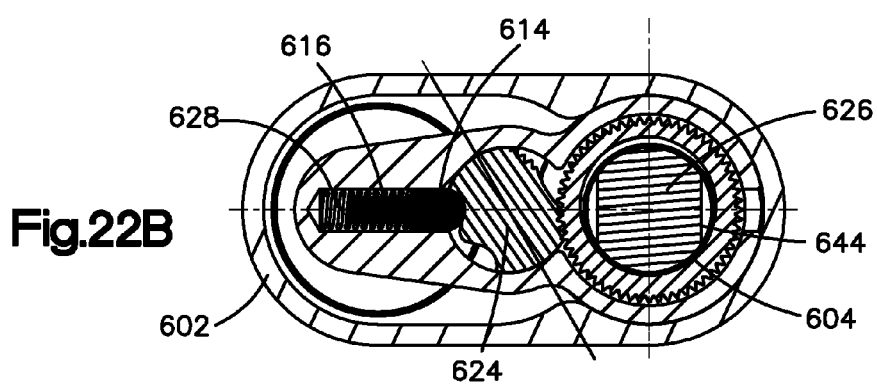
Figure 22C:
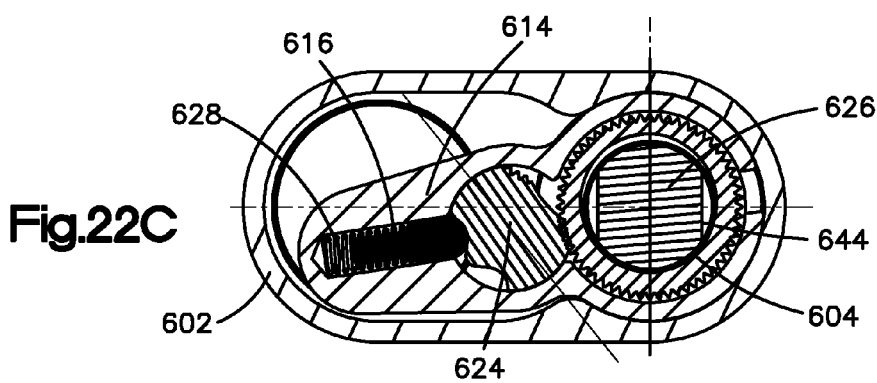
Figure 22D:
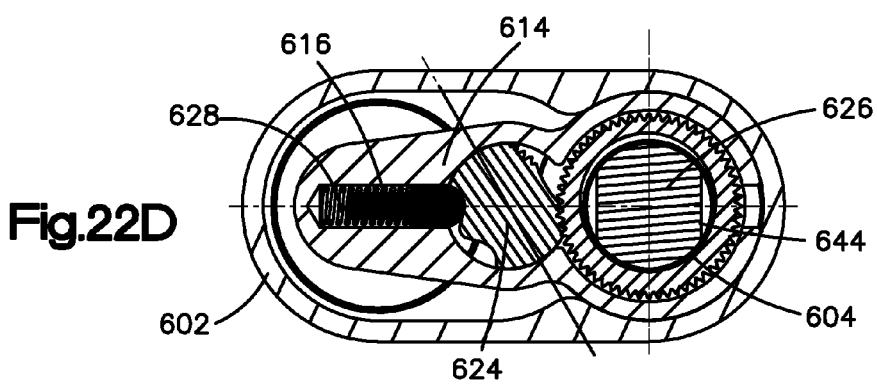
Figure 31A:
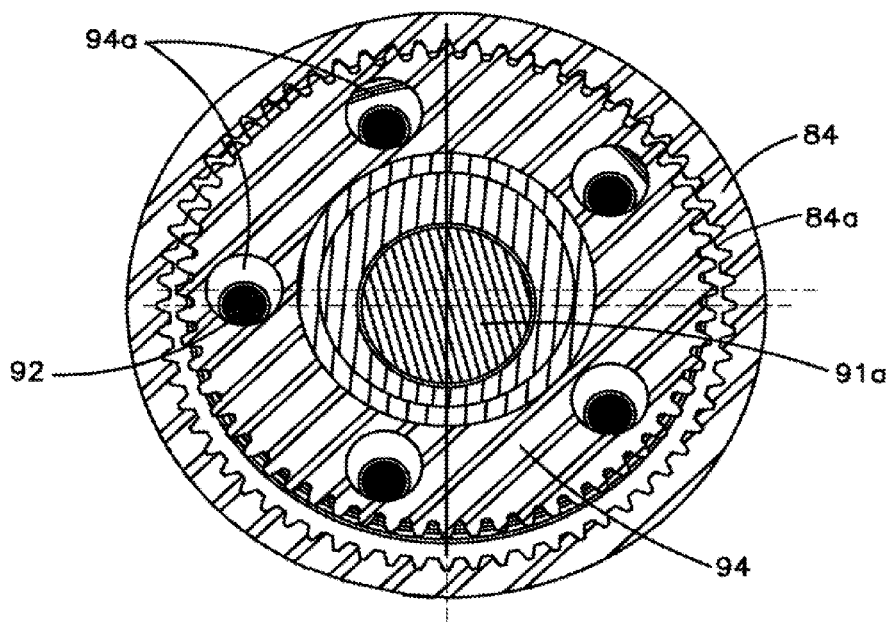
FIGS. 31A-31B illustrate magnified cross-sectional views of the growing rod of FIG. 28 taken from within circle Y of FIG. 29E and along line c-c of FIG. 29A, respectively.
Figure 31B:
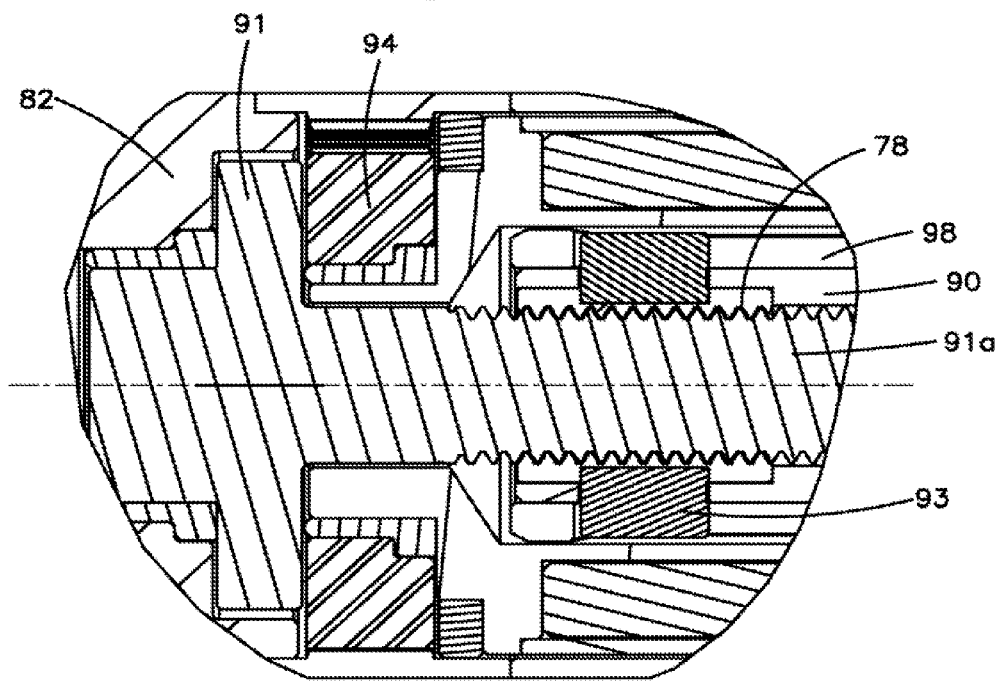

Referring to FIGS. 16-18, in a fifth implementation, a growing rod 510 operates and has substantially similar components to the above-described first through fourth implementations of the growing rod 10, 210, 310, 410. Like reference numerals are utilized to identify like components of the growing rod 510 of the fifth implementation with a prefix "5" utilized to specifically identify the components of the fifth implementation. Components of the growing rod 510 of the fifth implementation that are different than the above-described components of the other implementations are described below and similar or like components are excluded from the detailed description.

In the fifth implementation, the torque pins 534 are mounted to the top housing 532 proximate to a location where the rod 526 exits the top housing 534. The rod 526 includes flats 544 extending generally longitudinally along an external surface that interact with the torque pins 534 to generally prevent or limit pivoting or rotational movement of the rod 526 during operation. In addition, the shaft 503 of the carrier gear 504 is relatively long and includes the internal teeth 504b generally along an entire internal surface that engage threads 526a that are substantially located an end of the rod 526 opposite the attachment end 526b of the rod 526. Accordingly, when the rod 526 is extended from the top housing 532 and the attachment ends 526b, 501b of the rod 526 and base rod 1 are secured to the attachment mechanisms $A_1$-$A_8$ to correct the patient's anatomy, the base rod 501b and the rod 526b are generally placed under compression. In the fifth implementation, the shaft 503 is placed in tension when the rod 526 is placed in compression.

In use, the growing rod 510 of the fifth implementation operates in a substantially similar manner to the above-described preferred growing rods 10, 210, 310, 410 and its overall operation will not be described. However, in operation, the shaft 503 of the carrier gear 504 is typically placed in tension when positioned in the anatomy, which may be preferable for the shaft 503 to react tension load as opposed to a compression load. In addition, the torque pins 534 slide along the flats 544 on the rod 526 to limit rotation of the rod 526 when the growing rod 510 is in operation. Limiting or generally preventing rotation or pivoting of the rod 526 in operation permits the attachment mechanisms $A_1$-$A_8$ that are attached to the patient's anatomy to be fixed to the rod 526, thereby eliminating the need for a specific, potentially complicated grasping mechanism that is able to grasp the rod 526 and hold the rod as it rotates during use. However, the rod 526 and the base rod 501 are not limited to being free from rotation during use and may be mounted to the attachment mechanisms $A_1$-$A_8$ utilizing adaptors that permit rotation of the rod 526 and the base rod 501 and secure engagement with the attachment mechanisms $A_1$-$A_8$. For example, one of the attachment mechanisms $A_1$-$A_8$ may be comprised of a pedicle screw (not shown) with a bearing or bushing therein that permits rotation of the rod 526 or base rod 501 attached thereto while securing the rod 526 and base rod 501 to the pedicle screw such that the pedicle screw translates as the rod 526 or base rod 501 translates.

Referring to FIGS. 19-23, in a sixth implementation, a growing rod 610 has similar components and operates in a similar manner to the above-described implementations of the growing rods 10, 210, 310, 410, and 510. Like reference numerals are utilized to identify like components and a prefix "6" is utilized to specifically identify the components and elements of the growing rod 610 of the sixth implementation.

Components of the growing rod 610 of the sixth implementation that are different than the components of the above-described first through fifth implementations of the growing rod 10, 210, 310, 410, 510 are described below while repeat description of the similar or same components are omitted.

The growing rod of the sixth implementation integrally forms the gear housing 612, bottom housing 602 and base rod 601 in a single, integral component. Accordingly, the external housing components of the sixth implementation of the growing rod 610 are generally limited to the integral base rod 601, bottom housing 602 and gear housing 612, which is preferably laser welded to the top housing 632. The rod 626 is the only other component visible on the outside to the completely assembled growing rod 610 and extension of the rod 626 out of the top housing 632 is the only seal besides the laser-welding of the top housing 632 to the gear housing 612 that is sealed to the patient's anatomy or to other outside influences. Accordingly, the growing rod 610 of the sixth implementation has a relatively lowered part count and simplified sealing requirement when compared to the previously described implementations.

Referring specifically to FIGS. 21-22, operation of the pawl 624 to drive the carrier gear 604 in forward and reverse directions is shown in cross-section. Specifically, the locking ball 616 is positioned in a first of the pawl grooves 624b when the growing rod 610 is operating in the forward direction and the locking ball 616 is positioned in the other of the pawl grooves 624b when the growing rod 610 is operating in the reverse direction. This manipulation of the position of the locking ball 616 in one of the pawl grooves 624b blocks rotation of the carrier gear 604 in one direction and drives rotation of the carrier gear 604 in the opposite direction. Such a manipulation of the pawl 624 of the sixth implementation is identical to the manner in which the other implementations of the growing rods 10, 210, 310, 410, 510 may be manipulated to operate in forward and reverse directions. Accordingly, if a surgeon desires to draw the attachment ends 601b, 626b of the base rod 601 and the rod 626 toward each other, the growing rod 610 and any of the other preferred growing rods 10, 210, 310, 410, 510 may be configured in this manner. Accordingly, the preferred growing rods 10, 210, 310, 410, 510, 610 are able to grow or contract depending upon how the surgeon prefers to utilize the rods 10, 210, 310, 410, 510, 610. For example, referring to FIG. 1A, the growing rod 10 on the right lateral side of the scoliotic spine are preferably configured to contract to draw the ribs R on the open side of the scoliotic "C" curve together, while the growing rods 1° on the left lateral side of the scoliotic spine are preferably configured to expand to urge the ribs R and/or vertebra V on the closed side of the scoliotic "C" curve apart in an attempt to realign or move the spine toward a more anatomically correct curvature. In addition, the growing rod 1° mounted to the sacrum S and the lumbar vertebrae V may also be configured to contract to correct scoliotic curve of the lumbar section of the spine.

Referring to FIGS. 25-27 in a seventh implementation, a growing rod 50 is comprised of a spur gear-type mechanism. The growing rod 50 of the seventh implementation includes a top housing 52 with an attachment end 52a, a gear housing 54 preferably laser welded to the top housing 52, a bottom housing 56 preferably laser welded to the gear housing 54 and a rod 56 including an attachment end 58a that movably extends out of the bottom housing 56 along a longitudinal axis. The attachment ends 52a, 58a of the top housing 52 and rod 58, respectively, are utilized to attach the growing rod 50 to the attachment mechanisms $A_1$-$A_8$ that are fixed to boney structures of the patient's anatomy. The indications for the growing rod 50 of the seventh implementation are similar to the indications and manner of attaching the growing rods 10, 210, 310, 410, 510, 610 of the above-described implementations and are not described in further details with respect to the growing rod 50 of the seventh implementation.

The growing rod 50 of the seventh implementation also includes a magnet 64 having poles that is utilized to drive the operation of the growing rod 50 with an external magnet or magnetic field to permit the growing rod 50 to move without invasive surgical techniques. The magnet 64 is mounted within a top magnet cover 60 and a bottom magnet cover 62. The magnet 64, top magnet cover 60 and bottom magnet cover 62 are generally mounted within the top housing 52 along the longitudinal axis and are pivotal about the longitudinal axis. The top magnet cover 60 includes a pivot pin 60a that is secured in a bearing or bushing 74 within the top housing 52 and the bottom magnet cover 62 includes a pivot pin 62a extending away from the magnet 64.

The magnet 64 drives translation of the rod 58 via a gear reduction mechanism. The gear reduction mechanism includes a small central gear 66 mounted on the pivot pin 62a of the bottom magnet cover 62, a pair of relatively large offset gears 68, a pair of spindles 70 that are secured to the large offset gears 68 and a carrier 72 that is threadably secured to the spindles 70 and is fixed to an end of the rod 58. The rod 58 is isolated from rotation relative to the gear housing 54 by mounting the rod 58 to the carrier 72, which slides within a slot in the gear housing 54 and bottom housing 56.

In use, the growing rod 50 is mounted at the attachment ends 52a, 58a to attachment mechanisms $A_1$-$A_8$ that are secured to the patient and the surgical incision is closed. A surgeon, medical professional or other caregiver may extend or retract the rod 50 without additional incisions by passing a magnet proximate to the growing rod 50 or by applying a magnetic field to the growing rod 50 to cause the magnet 64 to rotate within the top housing 52. Rotation of the magnet 64 drives rotation of the small central gear 66, which also drives rotation of the large offset gears 68. Rotation of the large offset gears 68 causes the spindles 70 to rotate and urge the carrier 72 along the longitudinal axis, preferably toward a distal end of the bottom housing 56 when operating in a forward or expanding direction. As the carrier 72 translates along the longitudinal axis, the rod 52 is urged out of the bottom housing 56 and the distance between the fasteners or attachment mechanisms $A_1$-$A_8$ secured to the attachment ends 52a, 58a are driven apart. Consequently, the patient's anatomy is gradually shifted to urge the anatomy toward an anatomically correct orientation.

Similar to the above-described preferred growing rods 10, 210, 310, 410, 510, 610, the growing rod 50 and its components are preferably constructed of titanium or titanium alloys but are not so limited and may be constructed of cobalt chromium material, polymeric materials or nearly any bio-compatible material that is relatively strong and stiff, is able to take on the general size of the growing rod 50 and its components and able to withstand normal operating conditions of the growing rod 50. However, the bearings 74 are preferably constructed of a Polyether ether ketone (PEEK) material that is biocompatible and has a relatively low coefficient friction. The bearings 74 are not limited to constructions utilizing PEEK materials and may be constructed of nearly any material that permits the associated parts to slide relative thereto for pivoting.

Referring to FIGS. 28-31, in an eighth implementation, a growing rod 80 is comprised of an excenter-style growing rod 80. The external components of the growing rod 80 of the eighth implementation include a top housing 82 with an attachment end 82a, a gear housing 84 preferably laser welded to the top housing 82, a middle housing 86 preferably laser welded to the gear housing 84, a bottom housing 88 preferably laser welded to the middle housing 86 and a rod 90 that movably extends out of the bottom housing 88. The rod 90 includes an attachment end 90a that along with the attachment end 82a of the top housing 82 are used to secure the growing rod 80 to attachment mechanisms $A_1$-$A_8$ and the patient's anatomy. The growing rod 80 also includes a magnet 96 that is polarized and rotates when actuated by passing a magnet in close proximity thereto or a magnetic field. The magnet 96 is secured between a magnet bottom cover 95 and a magnet top cover 97, preferably within the middle housing 86.

The movement of the rod 90 is driven by the magnet 96 through a gear reduction mechanism of the eighth implementation of the growing rod 80. The gear reduction mechanism includes an eccentric end 95a on an end of the magnet bottom cover 95, a gear wheel 94 secured to the eccentric end 95a that includes eccentric holes 94a and mates with internal teeth 84a of the gear housing 84, driver pins 92 that loosely fit in the eccentric holes 94a of the gear wheel 94 and a driver wheel 91 to which the driver pins 92 are fix. The driver wheel 91 includes a threaded shaft 91a that mates with internal threads of the rod 90. A slider 98 is fixed to the bottom housing 88 and includes a pair of slots 98a therein that receive torque pins 93 fixed to the rod 90 to prevent or limit any pivotal or rotational movement of the rod 90 during operation of the growing rod 80. A carrier 78 having internal threads is mounted to the threaded shaft 91a of the driver wheel 91 and is secured to the torque pins 93 to urge the rod 90 out of the bottom housing 88.

In operation, the growing rod 80 is mounted to the attachment mechanisms $A_1$-$A_8$ within the patient and the magnet 96 is actuated to rotate. Rotation of the magnet 96 causes the magnet bottom cover 95 and the gear wheel 94 to rotate. The gear teeth on the external surface of the gear wheel 94 are mismatched with the internal gear teeth 84a of the gear housing 84 such that the eccentric rotation of the gear wheel 94 causes the gear teeth to mesh, but the internal bearing 99a permits the gear wheel 94 to rotate approximately one fifteenth (1/15) of a full rotation for every full rotation of the magnet 96. This reduced rotation of the gear wheel 94 is transmitted to the driver wheel 91 through the driver pins 92. Rotation of the driver wheel 91 causes rotation of the threaded shaft 91a and translational movement of the carrier 78 and rod 90 relative to the threaded shaft: 91 a. Engagement between the torque pins 93 and the slots 98a in the slider 98 permit the rod 90 to translate out of the bottom housing 88 to expand the growing rod 80.

Referring to FIGS. 32-34, in a ninth implementation, a growing rod 950 is substantially similar to and includes similar components to the growing rod 50 of the seventh implementation. Like reference numerals are utilized to identify like elements of the ninth implementation in comparison to the seventh implementation with a prefix "9" to specifically identify the components of the growing rod 950 of the ninth implementation. Detailed descriptions of each of the components of the growing rod 950 of the ninth implementation are omitted and differences between the growing rod 950 of the ninth implementation and the growing rod 50 of the seventh implementation are highlighted in the below description.

In the ninth implementation, the gear housing 954 of the growing rod 950 houses a majority of the magnet 964, bottom magnet cover 962 and top magnet cover 960. Accordingly, the length of the growing rod 950 in accordance with the ninth implementation having the spur gear-style is shortened in comparison to the spur gear-style growing rod 50 of the seventh implementation because the magnet 964, spindles 970 and rod 958 are concentrated in one section in parallel along the longitudinal axis of the growing rod 950 within the gear housing 954, as opposed to the seventh implementation of the growing rod 50 wherein the magnet 64 and spindles 70 are independently positioned in series along the longitudinal axis.

A maximum width of the gear housing 954 of the ninth implementation may also be slightly reduced in comparison to the gear housing 54 of the growing 50 of the seventh implementation because of an offset of the small central gear 966 relative to the longitudinal axis and the large offset gears 968. In contrast, the small central gear 66 of the growing rod 50 of the seventh implementation is generally coaxially located on the longitudinal axis, thereby requiring a slightly larger maximum width for the gear housing 54 to accommodate the positioning of the central gear 66 and the offset gears 68.

Figure 37F:
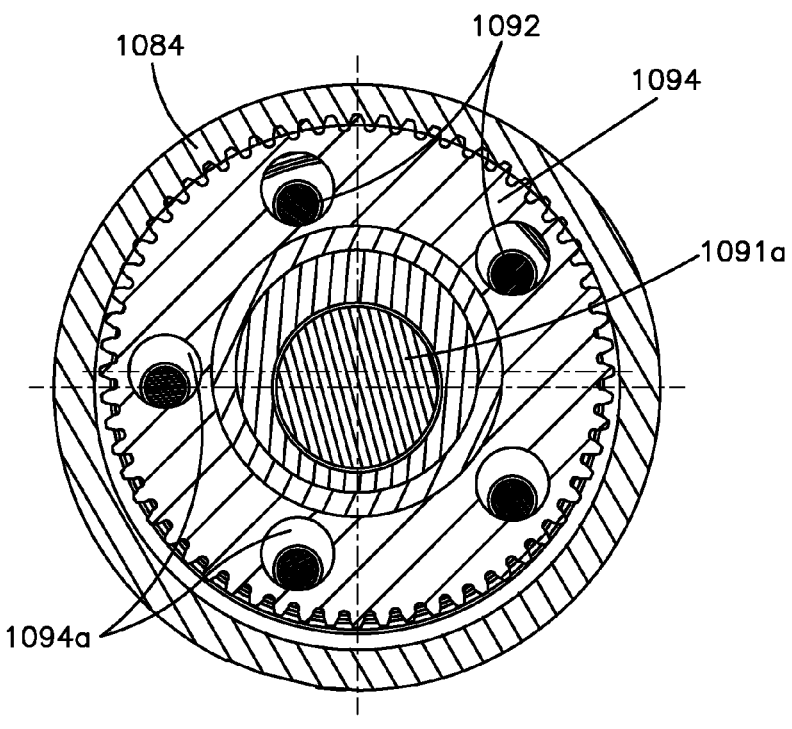
Figure 37G:
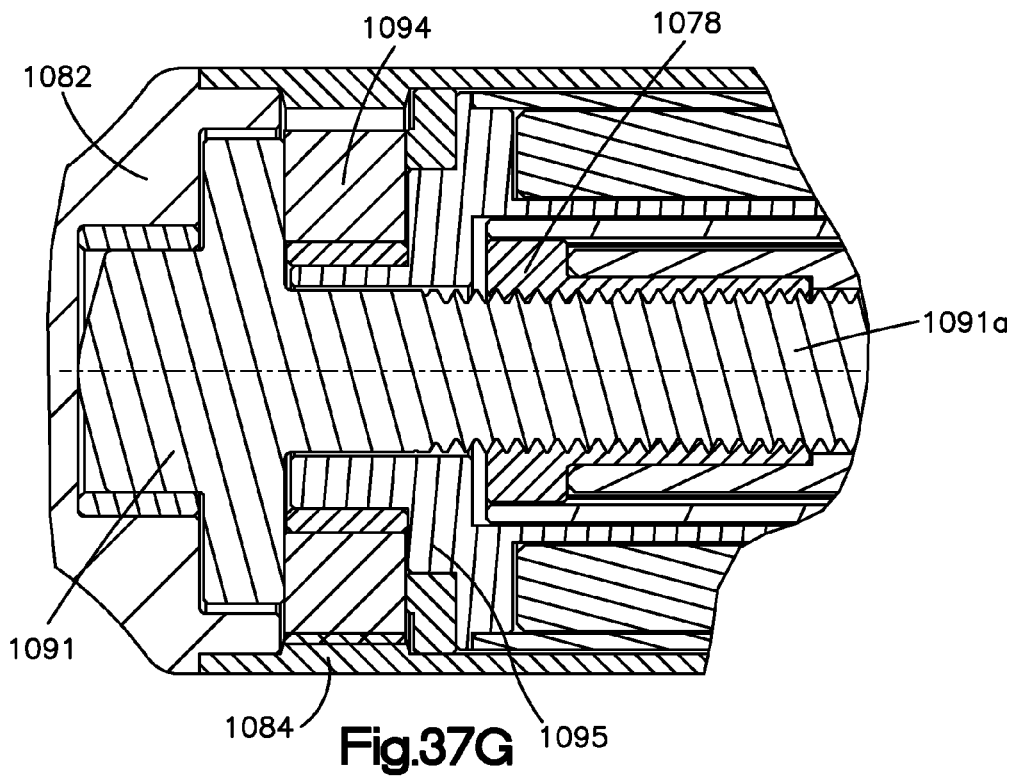

Referring to FIGS. 35-37, in a tenth implementation, a growing rod 1080 has an excenter-style design similar to the growing rod 80 of the eighth implementation. Like reference numerals are utilized to identify like components of the growing rod 1080 of the tenth implementation with a prefixed "10" utilized to identify the specific components of the tenth implementation in comparison to the growing rod 80 of the eighth implementation. The growing rod 1080 of the tenth implementation is substantially similar to the growing rod 80 of the eighth implementation and only components of the growing rod 1080 of the tenth implementation that are different than those of the eighth implementation are described below.

The gear housing 1084 of the tenth implementation is utilized as an integral component to comprise the separate gear housing 84 and middle housing 86 of the eighth implementation. Accordingly, the gear housing 1084 of the tenth implementation reduces part count and the number of seals required during the manufacturing process. The carrier 1078 of the growing rod 1080 of the tenth implementation is a keyed-design that is slidable within an internal surface of an internal extension 1088a of the bottom housing 1088. This configuration eliminates the slider 98 as well as the separate torque pins 93 described in the growing rod 80 of the eighth implementation.

Referring to FIGS. 38-40, in an eleventh implementation, a growing rod 1150 is substantially similar to the growing rod 950 of the ninth implementation. Like reference numerals are utilized to identify like elements and components that are different than the components of the growing rod 950 of the ninth implementation are highlighted below.

The growing rod 1150 of the eleventh implementation is constructed such that the magnet 1164 and a single spindle 1170 are positioned within the gear housing 1154 at a similar position in parallel along the longitudinal axis. In addition, the growing rod 1150 of the eleventh implementation includes a gear-reduction mechanism 1100 having four gears that reduce the rotational output of the spindle 1170 relative to an input rotation of the magnet 1164. The growing rod 1150 of the eleventh implementation further includes a carrier 1172 that is keyed to slide within the gear housing 1154 to prevent or limit pivoting or rotation of the rod 1158 during use. The carrier 1172 is keyed in a similar manner to the carrier 1078 of the growing rod 1080 of the tenth implementation.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the present description.

What is claimed is:

1. A growing rod, comprising:
   a base rod having an attachment end;
   an extendable rod being translatable relative to the base rod along a longitudinal axis;
   a housing enclosing at least a portion of the extendable rod therein;
   a magnet rotatably mounted within the housing and enclosed by a top magnet cover and a bottom magnet cover, the magnet including a first pole and a second pole; and
   a gear reduction mechanism associated with the magnet and the extendable rod, the gear reduction mechanism reducing an output rotation to the extendable rod in comparison to an input rotation from the magnet, the gear reduction mechanism comprising:
      a gear wheel located longitudinally adjacent to a driver wheel, the gear wheel eccentric with the driver wheel and having external gear teeth;
      a gear housing having internal gear teeth;
      the driver wheel having driver pins fixed thereto that extend from the driver wheel and that are fitted within the gear wheel, the driver wheel including a threaded shaft, and
      a carrier that mates with the threaded shaft and mates with the extendable rod by torque pins.

2. The growing rod of claim 1, wherein the extendable rod moves along the longitudinal axis substantially without rotation relative to the base rod.

3. The growing rod of claim 1, wherein the base rod and the extendable rod each include an attachment end that are attached to attachment points within a patient's body.

4. The growing rod of claim 3, wherein the attachment points are one of a pedicle screw, a hook or a cradle.

5. The growing rod of claim 1, wherein the growing rod, with an exception of the magnet, is constructed of a non-magnetizable material.

6. The growing rod of claim 5, wherein the non-magnetizable material comprises one of titanium, a titanium alloy material, a cobalt-chromium material or a polymeric material.

7. The growing rod of claim 1, wherein the extendable rod is moved relative to the base rod along the longitudinal axis by passing a magnetic field in proximity to the growing rod to cause the magnet to rotate about the longitudinal axis.

8. The growing rod of claim 1, wherein the external gear teeth are mismatched with the internal gear teeth such that the rotation of the gear wheel causes the external gear teeth and the internal gear teeth to mesh, and wherein the gear wheel rotates less than a full rotation for each full rotation of the magnet.

9. The growing rod of claim 8, wherein the gear wheel rotates approximately one-fifteenth of a rotation for each full rotation of the magnet.

10. The growing rod of claim 1, wherein rotation of gear wheel is transmitted to the driver wheel through the driver pins, and wherein rotation of the driver wheel causes rotation of the threaded shaft and the carrier to move the extendable rod out of the housing.

11. The growing rod of claim 1, further comprising a slider that is fixed to housing, the slider including a pair of slots that receive the torque pins to limit rotational movement of the extendable rod.

12. A growing rod, comprising:
   a housing;
   a fixed rod that is attached to the housing at a first end of the housing;
   an extendable rod that moves along a longitudinal axis of the growing rod and extending from a second end of the housing;
   a magnet mounted within the housing; and
   a gear reduction mechanism comprising:
      a gear wheel located longitudinally adjacent to a driver wheel, the gear wheel eccentric with the driver wheel and having external gear teeth;
      a gear housing having internal gear teeth;
      the driver wheel having driver pins fixed thereto that extend from the driver wheel and that are fitted within the gear wheel, the driver wheel including a threaded shaft; and
      a carrier that mates with the threaded shaft and to extendable rod by torque pins,
   wherein movement of the magnet caused by an external magnetic field is input to the gear reduction mechanism, and
   wherein the gear reduction mechanism reduces the input movement to produce an output that is translated into longitudinal movement of the extendable rod.

13. The growing rod of claim 12, wherein the magnet includes at least two poles, and wherein the extendable rod is moved relative to the fixed rod along the longitudinal axis by passing a magnetic field in proximity to the growing rod to cause the magnet to rotate about the longitudinal axis.

14. The growing rod of claim 12, wherein the external gear teeth are mismatched with the internal gear teeth such that the gear wheel rotates less than a full rotation for each full rotation of the magnet.

15. The growing rod of claim 12, further comprising a slider that is fixed to housing, the slider including a pair of slots that receive the torque pins to limit rotational movement of the extendable rod.

16. An expandable spinal growing rod, comprising:
a first rod that is fixedly attached to a housing at a first end of the housing;
a second rod that extends from a second end of the housing and that moves along a longitudinal axis; and
a magnet within the housing; and
a gear mechanism that is engaged by the magnet, wherein input rotational movement of magnet drives the gear mechanism, and wherein rotational movement of the gear mechanism is translated into longitudinal movement of the second rod relative to the housing,
the gear mechanism comprising a gear reduction mechanism that reduces the input rotational movement of the magnet with respect to an output of the gear mechanism, the gear reduction mechanism comprising:
a gear wheel located longitudinally adjacent to a driver wheel, the gear wheel eccentric with the driver wheel and having an external gear teeth,
a gear housing having internal gear teeth,
the driver wheel having driver pins fixed thereto that extend from the driver wheel and that are fitted within the gear wheel, the driver wheel including a threaded shaft, and
a carrier that mates with the threaded shaft and to the second rod by torque pins.

17. The spinal growing rod of claim 16, wherein the second rod moves along the longitudinal axis substantially without rotation relative to the first rod.

18. The spinal growing rod of claim 16, wherein the gear mechanism rotates bi-directionally such that second rod is moveable relative to the first rod along the longitudinal axis in a first direction away from the first rod or in a second direction toward the first rod.

19. The spinal growing rod of claim 16, wherein the input rotation movement of the gear mechanism is caused by passing a magnetic field in proximity to the magnet of the spinal growing rod.

* * * * *